United States Patent
Cruskie, Jr. et al.

(10) Patent No.: US 12,398,094 B2
(45) Date of Patent: Aug. 26, 2025

(54) POLYMORPHIC FORMS OF RAD1901-2HCL

(71) Applicant: Radius Pharmaceuticals, Inc., Boston, MA (US)

(72) Inventors: Michael Paul Cruskie, Jr., Florence, SC (US); Joshua Kyle Bolger, Florence, SC (US); Jonathan Blake Mckenzie, Latta, SC (US); Pratik Sheth, North Grafton, MA (US); Richard Edwards, Cambridge (GB); Alex Eberlin, Cambridge (GB); Michael Markey, Northborough, MA (US)

(73) Assignee: RADIUS PHARMACEUTICALS, INC., Boston, MA (US)

( * ) Notice: Subject to any disclaimer, the term of this patent is extended or adjusted under 35 U.S.C. 154(b) by 0 days.

(21) Appl. No.: 18/203,678

(22) Filed: May 31, 2023

(65) Prior Publication Data

US 2023/0373904 A1 Nov. 23, 2023

Related U.S. Application Data

(60) Continuation of application No. 17/475,018, filed on Sep. 14, 2021, now Pat. No. 11,708,318, which is a continuation of application No. 16/921,684, filed on Jul. 6, 2020, now Pat. No. 11,148,996, which is a division of application No. 16/456,314, filed on Sep. 13, 2019, now Pat. No. 10,745,343, which is a division of application No. 15/863,850, filed on Jan. 5, 2018, now Pat. No. 10,385,008.

(60) Provisional application No. 62/442,921, filed on Jan. 5, 2017.

(51) Int. Cl.
*C07C 217/84* (2006.01)
*A61P 35/00* (2006.01)
*C07C 213/10* (2006.01)

(52) U.S. Cl.
CPC ........... *C07C 217/84* (2013.01); *A61P 35/00* (2018.01); *C07C 213/10* (2013.01); *C07B 2200/13* (2013.01)

(58) Field of Classification Search
CPC ... A61P 35/00; C07B 2200/13; C07C 213/10; C07C 217/84
See application file for complete search history.

(56) References Cited

U.S. PATENT DOCUMENTS

| | | |
|---|---|---|
| 4,102,671 A | 7/1978 | Haddock et al. |
| 5,411,981 A | 5/1995 | Gaillard-Kelly et al. |
| 5,589,452 A | 12/1996 | Krstenansky et al. |
| 5,691,312 A | 11/1997 | Paques |
| 5,693,616 A | 12/1997 | Krstenansky et al. |
| 5,695,955 A | 12/1997 | Krstenansky et al. |
| 5,723,577 A | 3/1998 | Dong |
| 5,798,225 A | 8/1998 | Krstenansky et al. |
| 5,807,823 A | 9/1998 | Krstenansky et al. |
| 5,821,225 A | 10/1998 | Vickery |
| 5,840,837 A | 11/1998 | Krstenansky et al. |
| 5,874,086 A | 2/1999 | Krstenansky et al. |
| 5,886,225 A | 3/1999 | Jalett et al. |
| 5,955,574 A | 9/1999 | Dong |
| 5,969,095 A | 10/1999 | Dong |
| 5,977,070 A | 11/1999 | Piazza et al. |
| 6,017,924 A | 1/2000 | Edwards et al. |
| 6,050,988 A | 4/2000 | Zuck |
| 6,051,686 A | 4/2000 | Krstenansky et al. |
| 6,083,196 A | 7/2000 | Trautman et al. |
| 6,091,975 A | 7/2000 | Daddona et al. |
| 6,120,761 A | 9/2000 | Yamazaki et al. |
| 6,136,784 A | 10/2000 | L'Italien et al. |
| 6,156,899 A | 12/2000 | Galey et al. |
| 6,316,410 B1 | 11/2001 | Barbier et al. |
| 6,526,316 B2 | 2/2003 | Iga |
| 6,544,949 B1 | 4/2003 | Dong |
| 6,583,114 B2 | 6/2003 | Vickery |
| 6,670,386 B2 | 12/2003 | Sun et al. |
| 6,740,522 B2 | 5/2004 | Anderson |
| 6,740,650 B2 | 5/2004 | Lavoie et al. |
| 6,756,375 B2 | 6/2004 | Veeneman et al. |
| 6,756,480 B2 | 6/2004 | Kostenuik et al. |
| 6,770,623 B1 | 8/2004 | Chang et al. |
| 6,849,710 B1 | 2/2005 | Arzeno |
| 6,881,203 B2 | 4/2005 | Delmore et al. |
| 6,921,750 B2 | 7/2005 | Dong |

(Continued)

FOREIGN PATENT DOCUMENTS

| | | |
|---|---|---|
| CA | 2234724 | 10/1996 |
| EP | 1797038 B1 | 6/2012 |

(Continued)

OTHER PUBLICATIONS

"Deuterium." In http://www.britannica.com. Retrieved 18 Feb. 18, 2009 from <http://www.britannica.com/Ebchecked/topic/159684/deuterium>.
Acevedo et al., "Selective Androgen Receptor Modulators Antagonize ApolipoproteinE4-Induced Cognitive Impairments," Letters in Drug Design & Discovery, 2008, 5, 271-276.
Allan et al., "A selective androgen receptor modulator that reduces prostate tumor size and prevents orchidectomy-induced bone loss in rats," Journal of Steroid Biochemistry & Molecular Biology, 2007, 103, 76-83.
Allan et al., "A selective androgen receptor modulator with minimal prostate hypertrophic activity enhances lean body mass in male rats and stimulates sexual behavior in female rats," Endocr., 2007, 32:41-51.
Alluri, P.G., et al., Estrogen Receptor Mutations and Their Role in Breast Cancer Progression, Breast Cancer Research, 2014, 16:494.

(Continued)

*Primary Examiner* — Pancham Bakshi
(74) *Attorney, Agent, or Firm* — Honigman LLP; Christopher C. Forbes

(57) ABSTRACT

Various polymorphic forms of RAD1901-2HCl, including three crystalline and amorphous forms, are prepared and characterized. Uses of the various polymorphic forms of RAD1901-2HCl for cancer treatment are also disclosed.

16 Claims, 41 Drawing Sheets

(29 of 41 Drawing Sheet(s) Filed in Color)

(56) References Cited

U.S. PATENT DOCUMENTS

| | | | |
|---|---|---|---|
| 6,933,321 B2 | 8/2005 | Labrie et al. | |
| 7,056,886 B2 | 6/2006 | Isaacs | |
| 7,097,631 B2 | 8/2006 | Trautman | |
| 7,097,834 B1 | 8/2006 | Boyle | |
| 7,138,426 B2 | 11/2006 | Dininno et al. | |
| 7,141,544 B2 | 11/2006 | Somers et al. | |
| 7,172,999 B2 | 2/2007 | Mattern et al. | |
| 7,186,683 B2 | 3/2007 | Henriksen | |
| 7,214,381 B2 | 5/2007 | Carrara | |
| 7,244,709 B2 | 7/2007 | Quay et al. | |
| 7,256,208 B2 | 8/2007 | Bi et al. | |
| 7,282,507 B2 | 10/2007 | Lanter et al. | |
| 7,335,377 B2 | 2/2008 | Stern | |
| 7,363,075 B2 | 4/2008 | Stern | |
| 7,364,736 B2 | 4/2008 | Boyle et al. | |
| 7,365,202 B2 | 4/2008 | Tan et al. | |
| 7,371,721 B2 | 5/2008 | Henriksen et al. | |
| 7,383,084 B2 | 6/2008 | Stern | |
| 7,388,027 B2 | 6/2008 | Li et al. | |
| 7,390,923 B2 | 6/2008 | Ratilainen | |
| 7,405,234 B2 | 7/2008 | Sun et al. | |
| 7,410,948 B2 | 8/2008 | Dong | |
| 7,411,039 B2 | 8/2008 | Thim et al. | |
| 7,411,050 B2 | 8/2008 | Anderson | |
| 7,465,809 B2 | 12/2008 | Zhang et al. | |
| 7,514,470 B2 | 4/2009 | Turnbull et al. | |
| 7,537,795 B2 | 5/2009 | Cormier | |
| 7,556,821 B2 | 7/2009 | Ameri | |
| 7,558,625 B2 | 7/2009 | Levin | |
| 7,566,733 B2 | 7/2009 | Ng et al. | |
| 7,572,820 B2 | 8/2009 | Turnbull et al. | |
| 7,579,013 B2 | 8/2009 | Ameri | |
| 7,585,877 B2 | 9/2009 | Schlienger et al. | |
| 7,612,114 B2 * | 11/2009 | Hamaoka | C07D 213/64 564/307 |
| 7,622,592 B2 | 11/2009 | Kim et al. | |
| 7,625,923 B2 | 12/2009 | Nirschl et al. | |
| 7,632,858 B2 | 12/2009 | Hamann et al. | |
| 7,662,404 B2 | 2/2010 | Stern | |
| 7,696,227 B2 | 4/2010 | Diamond et al. | |
| 7,696,241 B2 | 4/2010 | Li et al. | |
| 7,741,352 B2 | 6/2010 | Brown et al. | |
| 7,795,280 B2 | 9/2010 | Hermkens et al. | |
| 7,799,757 B2 | 9/2010 | Chorev et al. | |
| 7,803,770 B2 | 9/2010 | Dey | |
| 7,807,691 B2 | 10/2010 | Gavardinas et al. | |
| 7,812,036 B2 | 10/2010 | Van Der Louw et al. | |
| 7,820,702 B2 | 10/2010 | Hamann et al. | |
| 7,829,589 B2 | 11/2010 | Saunders et al. | |
| 7,834,051 B2 | 11/2010 | Hasuoka | |
| 7,834,063 B2 | 11/2010 | Turnbull et al. | |
| 7,846,488 B2 | 12/2010 | Johnson et al. | |
| 7,906,137 B2 | 3/2011 | Byun et al. | |
| 7,932,399 B2 | 4/2011 | Alford et al. | |
| 7,935,722 B2 | 5/2011 | Fales et al. | |
| 7,968,587 B2 | 6/2011 | Boyd et al. | |
| 8,041,421 B2 | 10/2011 | Birchall | |
| 8,067,448 B2 | 11/2011 | Miller | |
| 8,110,562 B2 | 2/2012 | Dalton et al. | |
| 8,133,505 B2 | 3/2012 | Stern | |
| 8,143,425 B2 | 3/2012 | Ewing et al. | |
| 8,148,333 B2 | 4/2012 | Dey | |
| 8,217,032 B2 | 7/2012 | Dally et al. | |
| 8,329,649 B2 | 12/2012 | Asada et al. | |
| 8,399,520 B2 | 3/2013 | Hamaoka | |
| 8,450,481 B2 | 5/2013 | Masliah et al. | |
| 8,486,943 B2 | 7/2013 | Jadhav et al. | |
| 8,501,814 B2 | 8/2013 | Ratilainen et al. | |
| 8,519,158 B2 | 8/2013 | Zhi et al. | |
| 8,592,452 B2 | 11/2013 | Yamamoto | |
| 8,632,801 B2 | 1/2014 | Ameri et al. | |
| 8,748,382 B2 | 6/2014 | Dey | |
| 8,933,130 B2 | 1/2015 | Lytde | |
| 8,980,272 B2 | 3/2015 | Nomiyama | |
| 8,987,319 B2 | 3/2015 | Miller | |
| 9,133,182 B2 | 9/2015 | Miller | |
| 9,139,520 B2 | 9/2015 | Zhi | |
| 9,284,345 B2 | 3/2016 | Labrie et al. | |
| 9,421,264 B2 | 8/2016 | Wardell et al. | |
| 9,549,746 B2 | 1/2017 | Woolfson et al. | |
| 9,555,014 B2 | 1/2017 | O'Dea et al. | |
| 9,623,087 B2 | 4/2017 | Zhang et al. | |
| 9,687,641 B2 | 6/2017 | Singh et al. | |
| 9,693,950 B2 | 7/2017 | Determan et al. | |
| 10,010,706 B2 | 7/2018 | Gonzalez et al. | |
| 10,238,848 B2 | 3/2019 | Singh et al. | |
| 10,385,008 B2 * | 8/2019 | Cruskie, Jr. | C07C 217/84 |
| 10,745,343 B2 * | 8/2020 | Cruskie, Jr. | C07C 213/10 |
| 11,148,996 B2 * | 10/2021 | Cruskie, Jr. | C07C 213/10 |
| 11,708,318 B2 * | 7/2023 | Cruskie, Jr. | C07C 213/10 514/654 |
| 2002/0077281 A1 | 6/2002 | Vickery | |
| 2002/0107505 A1 | 8/2002 | Holladay | |
| 2002/0177839 A1 | 11/2002 | Cormier et al. | |
| 2003/0039654 A1 | 2/2003 | Kostenuik et al. | |
| 2003/0063859 A1 | 4/2003 | Hamanaka | |
| 2003/0135150 A1 | 7/2003 | Kuribayashi | |
| 2003/0143276 A1 | 7/2003 | Hsia | |
| 2003/0181936 A1 | 9/2003 | Trautman et al. | |
| 2004/0214996 A1 | 10/2004 | Kostenuik et al. | |
| 2004/0265354 A1 | 12/2004 | Ameri et al. | |
| 2004/0265365 A1 | 12/2004 | Daddona et al. | |
| 2005/0000309 A1 | 1/2005 | Perni et al. | |
| 2005/0009739 A1 | 1/2005 | Wang et al. | |
| 2005/0032698 A1 | 2/2005 | Day et al. | |
| 2005/0096586 A1 | 5/2005 | Trautman | |
| 2005/0106209 A1 | 5/2005 | Ameri et al. | |
| 2005/0106227 A1 | 5/2005 | Zalipsky et al. | |
| 2005/0112135 A1 | 5/2005 | Cormier et al. | |
| 2005/0124537 A1 | 6/2005 | Kostenuik et al. | |
| 2005/0124625 A1 | 6/2005 | Salvati et al. | |
| 2005/0209144 A1 | 9/2005 | Billger et al. | |
| 2005/0210080 A1 | 9/2005 | Saika | |
| 2005/0222100 A1 | 10/2005 | Kloosterboer et al. | |
| 2005/0250749 A1 | 11/2005 | Labrie | |
| 2005/0261631 A1 | 11/2005 | Clarke et al. | |
| 2005/0276823 A1 | 12/2005 | Cini et al. | |
| 2005/0282749 A1 | 12/2005 | Henriksen et al. | |
| 2006/0115472 A1 | 6/2006 | Li et al. | |
| 2006/0142387 A1 | 6/2006 | Cadilla et al. | |
| 2006/0148893 A1 | 7/2006 | Blanc et al. | |
| 2006/0188555 A1 | 8/2006 | Cormier et al. | |
| 2006/0211608 A1 | 9/2006 | Holick | |
| 2007/0021216 A1 | 1/2007 | Guruparan | |
| 2007/0034846 A1 | 2/2007 | Ratanasiriwillai | |
| 2007/0129409 A1 | 6/2007 | Hu et al. | |
| 2007/0155664 A1 | 7/2007 | Ranklove | |
| 2007/0184096 A1 | 8/2007 | Ameri | |
| 2007/0196395 A1 | 8/2007 | Mackerell et al. | |
| 2007/0213543 A1 | 9/2007 | Rodriguez | |
| 2007/0249520 A1 | 10/2007 | Gore et al. | |
| 2007/0256736 A1 | 11/2007 | Tonkovich et al. | |
| 2007/0287949 A1 | 12/2007 | Levin | |
| 2007/0299009 A1 | 12/2007 | Dong | |
| 2008/0008433 A1 | 1/2008 | Parker | |
| 2008/0024456 A1 | 1/2008 | Peng et al. | |
| 2008/0027096 A1 | 1/2008 | Garg et al. | |
| 2008/0039775 A1 | 2/2008 | Ameri | |
| 2008/0044033 A1 | 2/2008 | Ozawa | |
| 2008/0045504 A1 | 2/2008 | Gant et al. | |
| 2008/0051699 A1 | 2/2008 | Choi et al. | |
| 2008/0058383 A1 | 3/2008 | Jernstedt et al. | |
| 2008/0114048 A1 | 5/2008 | Sui | |
| 2008/0119401 A1 | 5/2008 | Dong | |
| 2008/0121602 A1 | 5/2008 | Zhang | |
| 2008/0124000 A1 | 5/2008 | Sato et al. | |
| 2008/0124402 A1 | 5/2008 | Kim et al. | |
| 2008/0125399 A1 | 5/2008 | Wang et al. | |
| 2008/0127717 A1 | 6/2008 | Lesieur | |
| 2008/0194536 A1 | 8/2008 | Hammond et al. | |
| 2008/0269685 A1 | 10/2008 | Singh et al. | |
| 2009/0069226 A1 | 3/2009 | Ong et al. | |
| 2009/0117158 A1 | 5/2009 | Ameri et al. | |
| 2009/0133861 A1 | 5/2009 | Kim | |

(56) References Cited

U.S. PATENT DOCUMENTS

| | | |
|---|---|---|
| 2009/0170907 A1 | 7/2009 | Turnbull et al. |
| 2009/0198189 A1 | 8/2009 | Simons |
| 2009/0227498 A1 | 9/2009 | Dey et al. |
| 2009/0227571 A1 | 9/2009 | Loren et al. |
| 2009/0305965 A1 | 12/2009 | Kang et al. |
| 2009/0325930 A1 | 12/2009 | Hamaoka |
| 2010/0016223 A1 | 1/2010 | Gimona et al. |
| 2010/0030100 A1 | 2/2010 | Tokumoto et al. |
| 2010/0092566 A1 | 4/2010 | Alessi et al. |
| 2010/0105733 A1 | 4/2010 | Lyttle |
| 2010/0118287 A1 | 5/2010 | Kikuchi et al. |
| 2010/0119568 A1 | 5/2010 | Ameri |
| 2010/0151247 A1 | 6/2010 | Moore et al. |
| 2010/0152649 A1 | 6/2010 | Ameri |
| 2010/0160895 A1 | 6/2010 | Ameri |
| 2010/0203014 A1 | 8/2010 | Maggio |
| 2010/0221305 A1 | 9/2010 | Ameri |
| 2010/0226966 A1 | 9/2010 | Daddona |
| 2011/0006458 A1 | 1/2011 | Sagi et al. |
| 2011/0009387 A1 | 1/2011 | Basso-Porcaro |
| 2011/0046052 A1 | 2/2011 | Yang |
| 2011/0092425 A1 | 4/2011 | Dey |
| 2011/0124617 A1 | 5/2011 | Lyttle et al. |
| 2011/0124817 A1 | 5/2011 | Dias |
| 2011/0172609 A1 | 7/2011 | Moga |
| 2011/0213335 A1 | 9/2011 | Burton et al. |
| 2011/0276028 A1 | 11/2011 | Singh et al. |
| 2011/0288485 A1 | 11/2011 | Tokumoto |
| 2012/0150023 A1 | 6/2012 | Kasper et al. |
| 2012/0219538 A1 | 8/2012 | Borchard et al. |
| 2013/0006217 A1 | 1/2013 | Hattersley |
| 2013/0085105 A1 | 4/2013 | Deasy |
| 2013/0116232 A1 | 5/2013 | Kahraman |
| 2013/0123707 A1 | 5/2013 | Determan et al. |
| 2013/0157955 A1 | 6/2013 | Dey |
| 2014/0024582 A1 | 1/2014 | Yang |
| 2014/0046292 A1 | 2/2014 | Hattersley |
| 2014/0046293 A1 | 2/2014 | Hattersley |
| 2014/0228293 A1 | 8/2014 | Danishefsky et al. |
| 2014/0330198 A1 | 11/2014 | Zhang et al. |
| 2014/0343499 A1 | 11/2014 | Zhang |
| 2015/0231134 A1 | 8/2015 | Erichsen |
| 2015/0274640 A1 | 10/2015 | Wardell et al. |
| 2016/0324808 A1 | 11/2016 | Wardell et al. |
| 2018/0153828 A1 | 6/2018 | Garner et al. |
| 2018/0169101 A1 | 6/2018 | Hattersley |
| 2018/0214393 A1 | 8/2018 | Hattersley |
| 2021/0052705 A1 | 2/2021 | Hattersley et al. |

FOREIGN PATENT DOCUMENTS

| | | |
|---|---|---|
| JP | 1261381 | 10/1989 |
| JP | 2003519698 A | 6/2003 |
| JP | 2018514593 A | 6/2018 |
| WO | 1996/035447 A1 | 11/1996 |
| WO | 2001/036039 A2 | 5/2001 |
| WO | 2003063859 A1 | 8/2003 |
| WO | 2004/060386 A1 | 7/2004 |
| WO | 2005000309 A2 | 1/2005 |
| WO | 2007034846 A1 | 3/2007 |
| WO | 2008008433 A2 | 1/2008 |
| WO | 2008024456 A2 | 2/2008 |
| WO | 2008044033 A1 | 4/2008 |
| WO | 2008121602 A1 | 10/2008 |
| WO | 2008124000 A2 | 10/2008 |
| WO | 2008127717 A1 | 10/2008 |
| WO | 2009/053106 A1 | 4/2009 |
| WO | 2009133861 A1 | 11/2009 |
| WO | 2010/022176 A1 | 2/2010 |
| WO | 2010118287 A1 | 10/2010 |
| WO | 2011143469 A1 | 11/2011 |
| WO | 2012/075375 A1 | 6/2012 |
| WO | 2014/203129 A1 | 12/2014 |
| WO | 2016-176665 A1 | 11/2016 |

OTHER PUBLICATIONS

Ameri, M., et al., (2010) "Parathyroid Hormone PTH(1-34) Formulation that Enables Uniform Coating on a Novel Transdermal Microprojection Delivery System," Pharmaceutical Res, 27(2):303-313; Feb. 2010 (published online Dec. 15, 2009).

Ameri, M., et al., "Demonstrated Solid-State Stability of Parathyroid Hormone PTH(1-34) Coated on a Novel Transdermal Microprojection Delivery System," Pharmaceutical Res, 26(11):2454-2463; Nov. 2009; (published online Sep. 3, 2009).

Amugongo, S. K., et al., (2014) "Effect of Sequential Treatments with Alendronate, Parathyroid Hormone (1-34) and Raloxifene on Cortical Bone Mass and Strength in Ovariectomized Rats," Bone 67:257-268.

Anderson, "The Process of Structure-Based Drug Design," Chemistry & Biology, 2003, vol. 10, 787-797.

Anonymous: Radius Announced today that It Has Acquired The License To Develop and Market RAD1901 in Japan, MPM Globe Newswire, Mar. 10, 2015, pp. 1-5, XP055683544; retrieved from: url:https://www.mpmcapital.com/press/radius-rdus-anounced-today-acquired-license-develop-market-rad1901-japan/; retrieved Apr. 7, 2020.

Arun, B., et al., "The Search for the Ideal SERM," *Expert. Opin. Pharmacother.*, 3(6):681-691 (2002).

Augustine, M et al., (2013) "Parathyroid Hormone and Parathyroid Hormone-related Protein Analogs as Therapies for Osteoporosis," Curr. Osteoporos. Rep. 11(4):400-406.

Australian Patent Office, Examination Report for SG20090240-1 mailed Nov. 18, 2010.

Australian Patent Office, International Search Report and Written Opinion for SG20090240-1 completed Apr. 1, 2010 and mailed Apr. 20, 2010.

Autoimmune disorders: MedlinePlus Medical Encyclopedia [online], [retrieved on Jun 3. 2011]. Retrieved from the Internet URL: http://www.nlm.nih.gov/medlineplus/ency/article/000816.htm.

Bellido, T. et al., (1999) "Estrogen Inhibit Apoptosis of Osteoblasts and Osteocytes through Rapid (Non-genomic) Activation of Extracellular Signal-Regulated Kinases (ERKs)," J Bone Mineral Res, 14(Supp 1)(Abstract SA135):S342.

Berge et al., "Pharmaceutical Salts," Journal of Pharmaceutical Sciences, 1977, 66(1):1-19.

Bodenner, D.L et al., (1999) "Essential Requirement of the Estrogen Receptor α or β for (Non-Genomic) Anti-Apoptotic Effects of Estrogen," J Bone and Mineral Res, 14(Supp 1)(Abstract F071):S227.

Bohl, C.E., et al., "Structural Basis for Accommodation of Nonsteroidal Ligands in the Androgen Receptors," J Biol Chem, 280(45):37747-37754 (Nov. 11, 2005).

Bohl et al., "Structural basis for antagonism and resistance of bicalutamide in prostate cancer," PNAS, 2005, vol. 102, No. 17, 6201-6206.

Bonnick, S. L., et al., (2001) "Importance of Precision in Bone Density Measurements," J. Clin. Densitometry 4(2):105-110.

Bonnick, S., et al., (2006) "Comparison of Weekly Treatment of Postmenopausal Osteoporosis with Alendronate Versus Risedronate Over Two Years," J. Clin. Endocrinol. Metab. 91(7):2631-2637.

Bostrom, M.P.G et al., (2000) "Parathyroid Hormone-Related Protein Analog RS-66271 is an Effective Therapy for Impaired Bone Healing in Rabbits on Corticosteroid Therapy," Bone, 26(5):437-442.

Brittain, Harry G., Polymorphism in Pharmaceutical Solids, Second Edition, Drugs and the Pharmaceutical Sciences, vol. 192, Informa Healthcare, 2009.

Browne, "Isotope Effect: Implications for Pharmaceutical Investigations," Stable Isotopes in Pharmaceutical Research, 1997, vol. 26, Chapter 2, pp. 13-18.

Burr, D. B., et al., (2001) "Intermittently Administered Human Parathyroid Hormone(1-34) Treatment Increases Intracortical Bone Turnover and Porosity Without Reducing Bone Strength in the Humerus of Ovariectomized Cynomolgus Monkeys," J. Bone Min. Res. 16(1):157-165.

Caira, Mino R., Crystalline Polymorphism of Organic Compounds, Topics in Current Chemistry vol. 198, 1998, pp. 163-208, Springer Verlag, Berlin DE.

(56) References Cited

OTHER PUBLICATIONS

Cantin et al., "Structural Characterization of the Human Androgen Receptor Ligand-biding Domain Complexed with EM5744, a Rationally Designed Steroidal Ligand Bearing a Bulky Chain Directed toward Helix 12," The Journal of Biological Chemistry, 2007, vol. 282, No. 42, pp. 30910-30919.

Cesnjaj et al., "In Vivo Models in the Study of Osteopenias," Eur. J. Clin Chem. Clin Biochem., 1991, vol. 29, pp. 211-219.

Chantasingh, D., et al., (2006) "Cloning, Expression, and Characterization of a Xylanase 10 from Aspergillus Terreus (BCC129) in Pichia Pastoris," Protein Expre Purif, 46(1):143-149 (Abstract Only).

Chinese Patent Office, Chinese Patent Search Report for 201110220104.X dated Feb. 26, 2013.

Chinese Patent Office, Chinese Patent Search Report for 201280030749X dated Feb. 16, 2015.

Chou, T.C., et al., (1984) "Quantitative Analysis of Dose-Effect Relationships: The Combined Effects of Multiple Drugs or Enzyme Inhibitors," Adv. Enzyme Regul. 22:27-55.

clinical trials.gov, "A Study for the Transdermal Application of Teriparatide," Retrieved from: http://www.clinicaltrials.gov/ct2/show/NCT01011556?term=pth+patch&rank=8, Date Retrieved: Sep. 18, 2012, 6 pages.

clinical trials.gov, "Dose Ranging Study—Macroflux PTH in Postmenopausal Women With Osteoporosis," Retrieved from: http://www.clinicaltrials.gov/ct2/show/NCT00489918?term=pth+patch&rank=1, Date Retrieved: Sep. 18, 2012, 1 page.

Cosman, F., (2008) "Parathyroid Hormone Treatment for Osteoporosis," Curr. Opin. Endocrinol. Diabetes Obes. 15:495-501.

Cosman, F., et al., (2009) "Effect of Transdermal Teriparatide Administration on Bone Mineral Density in Postmenopausal Women," J Clin Endocrinol Metab, 95(1):151-158 (published online Oct. 26, 2009).

Culler, M.D. et al., (2001) "BIM-44058, a Novel Analog of PTHrP with Enhanced Bone Building Activity, but Decreased Calcium-Mobilization Potential," Twenty-Third Annual Meeting of the American Society of Bone and Mineral Research, Phoenix, Arizona, USA, Oct. 12-16, 2001, J Bone Miner Res, (Abstract M460), 16(Suppl. 1):S540.

Culler, M.D. et al., (2002) "A Novel PTHRP Analog with Decreased Calcium-Mobilization Potential, but with Enhanced Bone Building Activity," S19, Abstract for the World Congress on Osteoporosis meeting held on May 10-14, 2002, Lisbon, Portugal (Abstract P51SU), Osteoporos Int 13(1) (Apr. 2002).

Daddona, Peter E., et al., (2011) "Parathyroid Hormone (1-34)-Coated Microneedle Patch System: Clinical Pharmacokinetics and Pharmacodynamics for Treatment of Osteoporosis," Pharm Res, 28:159-165 (published online Jun. 22, 2010).

Dean, T., et al., (2006) "Mechanisms of Ligand Binding to the Parathyroid Hormone (PTH)/PTH-Related Protein Receptor: Selectivity of a Modified PTH(1-15) Radioligand for Gαs-Coupled Receptor Conformations," Mol. Endocrinol. 20(4):931-943.

Dean, T., et al., (2008) "Altered Selectivity of Parathyroid Hormone (PTH) and PTH-Related Protein (PTHrP) for Distinct Conformations of the PTH/PTHrP Receptor", Molecular Endocrinology, 22(1):156-166.

Dempster, D. W., et al., (2012) "Skeletal Histomorphometry in Subjects on Teriparatide or Zoledronic Acid Therapy (SHOTZ) Study: A Randomized Controlled Trial," J. Clin. Endocrinol. Metab. 97(8):2799-2808.

Dempster, D.W. et al., (1993) "Anabolic Actions of Parathyroid Hormone on Bone," Endocr Rev, 14(6):690-709.

Dempster, D.W. et al., (2001) "Effects of Daily Treatment with Parathyroid Hormone on Bone Microarchitecture and Turnover in Patients with Osteoporosis: A Paired Biopsy Study," J Bone Miner Res, 16:1846-1853.

Deschamps, P., et al., (2005) "The Saga of Copper(II)-L-histidine," Coordination Chem Reviews, 249:895-909.

Dhainaut, A., et al., (2013) "Cortical Hand Bone Porosity and Its Association with Distal Radius Fracture in Middle Aged and Elderly Women," PLoS One 8(7):e68405.

Dong, J.Z. et al., (1998) "Development of Highly Potent Human Parathyroid Hormone Analogs," Peptides: Biology and Chemistry, Proceedings of the Chinese Peptide Symposium, 4th, Chengdu, Peop. Rep. China, Jul. 21-25, 1996, pp. 173-175.

Dong, J.Z. et al., (1999) "Highly Potent Human Parathyroid Hormone Analogs," Peptides: Frontiers of Peptide Science, Proceedings of the American Peptide Symposium, 15th, Nashville, Jun. 14-19, 1997, pp. 541-542.

Dong, J.Z. et al., (2001) "Highly Potent Analogs of Human Parathyroid Hormone and Human Parathyroid Hormone-Related Protein," Peptides: The Wave of the Future, Proceedings of the Second International and the Seventeenth American Peptide Symposium, San Diego, CA USA, Jun. 9-14, 2001, pp. 668-669.

Doyle, N., et al., (2013) "BA058, A Novel Human PTHrP Analog: Reverses Overiectomy-Induced Bone Lloss and Strength at the Lumbar Spine in Aged Cynomolgus Monkeys," J. Bone Miner. Res. 28(Suppl 1) Abstract.

Doyle, N., et al., (2013) "Long Term Effect of BA058, a Novel Human PTHrP Analog, Restores Bone Mass in the Aged Osteopenic Ovariectomized Cynomolgus Monkey," J. Bone Miner. Res. 28(Suppl 1):Abstract.

European Patent Office, Extended Search Report and Written Opinion for PCT/US2011/023768 (EP11740437, WO2011097496) complted Apr. 22, 2013 and mailed Apr. 26, 2013.

European Patent Office, Extended Search Report and Written Opinion for PCT/US2011/036311 (EP11781299, WO2011036311) complted Aug. 5, 2013 and mailed Aug. 13, 2014.

European Patent Office, Extended Search Report for PCT/US2011/023768 (EP11740437, W02011097496) mailed Apr. 26, 2013.

European Patent Office, International Search Report and Written Opinion completed Sep. 17, 2008 and mailed Jun. 4, 2009 for PCT/US2007/021216.

European Patent Office, International Search Report and Written Opinion completed Jul. 27, 2009 and mailed Aug. 3, 2009 for PCT/US2009/002868.

European Patent Office, International Search Report and Written Opinion completed Aug. 14, 2009 and mailed Sep. 10, 2010 for PCT/US2009/002885.

European Patent Office, International Search Report and Written Opinion completed Dec. 19, 2011 and mailed Jan. 16, 2012 for PCT/US2011/053375.

European Patent Office, International Search Report and Written Opinion for PCT/US2009/001035 mailed Aug. 7, 2009.

European Patent Office, International Search Report for EP15176548 completed Sep. 30, 2015 and mailed Oct. 7, 2015.

European Patent Office, International Search Report for PCT/EP1996/01962 mailed Sep. 16, 1996.

European Patent Office, International Search Report for PCT/US1997/22498 mailed Dec. 23, 1998.

European Pharmacopoeia 5.0 (EP), Chapter 5.1.3 "Efficacy of Antimicrobial Preservation," 447-4493; 2005.

Everhart-Caye, M. et al., (1996) "Parathyroid Hormone (PTH)-Related Protein(1-36) is Equipotent to PTH(1-34) in Humans," J Clin Endocrinol Metab, 81(1):199-208.

FDA Guidance for Industry (2003) "Q1A(R2) Stability Testing of New Drug Substances and Products.".

FDA, Full Prescribing Information for FORTEO (teriparatide) injection (2002).

Ferrandon, S., et al., "Sustained cyclic AMP production by parathyroid hormone receptor endocytosis", Nature Chemical Biology, 5(10):734-742 (Oct. 2009).

Fox, J., (2002) "Developments in Parathyroid Hormone and Related Peptides as Bone-Formation Agents," Curr Opin Pharmacology, 2:338-344.

Fraher, L.J. et al., (1992) "A Comparison of the in Vivo Biochemical Responses to Exogenous Parathyroid Hormone-(1-34) [PTH-(1-34)] and PTH-Related Peptide-(1-34) in Man," J Clin Endocrinol Metab, 75(2):417-423.

Fraher, L.J. et al., (1995) "Comparison of the Pharmacokinetics of Parenteral Parathyroid Hormone-(1-34) [PTH-(1-34)] and PTH-Related Peptide-(1-34) in Healthy Young Humans," J Clin Endocrinol Metab, 80(1):60-64 (1995).

(56) References Cited

OTHER PUBLICATIONS

Frolik, C.A. et al., (1999) "Comparison of Recombinant Human PTH(1-34) (LY333334) with a C-Terminally Substituted Analog of Human PTH-Related Protein (1-34) (RS-66271): In Vitro Activity and In Vivo Pharmacological Effects in Rats," J Bone Miner Res, 14(2):163-172.

Frolik, C.A. et al., (2000) "Reply: Further Data are Required to Assure that the Discrepant Binding Affinity is Explained by Different Receptor Conformations," J Bone Miner Res, 15(3):608.

Gallagher, J.C. et al., (1999) "PTHrP(1-34) Analog, Semparatide Acetate (RS-66271), Causes Sustained Increases in Spine in Postmanopausal Osteoporotic Women: Two Randomized Placebo-Controlled Trials," J Bone Mineral Res, 14(Supp 1)(Abstract 1018):S137.

Gallagher, J.C., et al., (2006) "Response Rate of Bone Mineral Density to Teriparatide in Postmenopausal Women with Osteoporosis," Bone 39:1268-1275.

Gao et al., "Expanding the therapeutic use of androgens via selective androgen receptor modulators (SARMs)" Drug Discovery Today, 2007, vol. 12, No. 5/6, pp. 241-248.

Gao, W., et al., "Comparison of the Pharmacological Effects of a Novel Selective Androgen Receptor Modulator, the 5a-Reductase Inhibitor Finasteride, and the Antiandrogen Hydroxyflutamide in Intact Rats: New Approach for Benign Prostate Hyperplasia," Endocrinology, 145(12):5420-5428 (2004).

Gao, W., et al., "Ockham's Razor and Selective Androgen Receptor Modulators (SARMs): Are we Overlooking the Role of 5a-Reductase?", Molecular Interventions, 7:1013 (2007).

Gao, W., et al., "Selective Androgen Receptor Modulator Treatment Improves Muscle Strength and Body Composition and Prevents Bone Loss in Orchidectomized Rats," Endocrinology, 146(11):4887-4897 (Nov. 2005).

Garland, M.J., et al., (2011) "Microneedle arrays as medical devices for enhanced transdermal drug delivery," Expert Rev Med Devices, 8(4):459-482.

Garner et al., "RAD1901: a novel, orally bioavailable selective estrogen receptor degrader that demonstrates antitumor activity in breast cancer xenograft models," Anti-Cancer Drugs, vol. 26, No. 9, Oct. 31, 2015, 9 pages.

Gill, H.S. and Prausnitz, M.R., (2007) "Coating Formulations for Microneedles," Pharmaceutical Res, 24(7):1369-1380.

Hamann, L.G., et al., "Tandem Optimization of Target Activity and Elimination of Mutagenic Potential in a Potent Series of N-aryl Bicyclic Hydantoin-Based Selective Androgen Receptor Modulators," Bioorganic & Medicinal Chemistry Letters, 17:1860-1864 (2007).

Han, S.L., et al., (2012) "Effect of Teriparatide on Bone Mineral Density and Fracture in Postmenopausal Osteoporosis: Meta-Analysis of Randomized Controlled Trials," Int. J. Clin. Pract. 66(2):199-209.

Hanada et al., "Bone Anabolic Effects of S-40503, a Novel Nonsteroidal Selective Androgen Receptor Modulator (SARM), in Rat Models of Osteoporosis," Biol. Pharm. Bull., 2003, 26(11):1563-1569.

Hansen, S., et al., (2013) "Differing Effects of PTH 1-34, PTH 1-84, and Zoledronic Acid on Bone Microarchitecture and Estimated Strength in Postmenopausal Women with Osteoporosis: An 18-Month Open-Labeled Observational Study Using HR-pQCT," J. Bone Min. Res. 28(4):736-745.

Hattersley, G., et al. "OR31-5: Differential Binding Selectivity of Abaloparatide (BA058) Compared to PTH and PTHrP for PTH Type 1 Receptor Conformations," Endocrine Society's 96th Annual Meeting and Expo, Jun. 21-24, 2014, Chicago, IL.

Hattersley, G., et al., (2013), "SUN-200: BA058, A Novel Human PTHrP Analog, Restores Bone Density and Increases Bone Strength at the Spine and Femur in Osteopenic Rats," Endocr. Soc. 95th Annual Meeting and Expo, San Francisco, CA, Jun. 15-18, 2013.

Henderson, "Estrogen Replacement Therapy for the Prevention and Treatment of Alzheimer's Disease," CNS Drugs, 1997, 8(5):343-351.

Henry, J.G. et al., (1997) "Parathyroid Hormone-Related Protein-(1-36) is Biologically Active When Administered Subcutaneously to Humans," J Clin Endocrinol Metab, 82(3):900-906.

Higuchi et al., "Novel Series of Potent, Nonsteroidal, Selective Androgen Receptor Modulators Based on 7H-[1,4]Oxazino[3,2-g]quinolin-7-ones," J. Med. Chem., 2007, 50, 2486-2496.

Hildebrand, T. et al., (1999) "Direct Three-Dimensional Morphometric Analysis of Human Cancellous Bone: Microstructural Data from Spine, Femur, Iliac Crest, and Calcaneus," J Bone Miner Res, 14(7):1167-1174.

Hilfiker, Rolf, et al., Relevance of Solid-State Properties for Pharmaceutical Products, Polymorphism: in the Pharmaceutical Industry, Wiley-VCH Verlag GmbH & Co., pp. 1-19, 2006.

Hirayama, R., editor; "Crystals Production Handbook—Principles and Know-how)", Maruzen Publishing, Jul. 25, 2008, 57-84.

Hoare, S.R.J. and Usdin, T.B., (1999) "Quantitative Cell Membrane-Based Radioligand Binding Assays for Parathyroid Hormone Receptors," J Pharmacol Toxicol, 41:83-90.

Hoare, S.R.J. and Usdin, T.B., (2000) "Letter to the Editor: The Discrepancy Between the Binding Affinity of PTH (1-34) and RS 66271 is Explained by Interaction of the PTH/PTHrP Receptor with G-Protein," J Bone Miner Res, 15(3):605-607.

Hochberg, M. C., et al., (1999) "Larger Increases in Bone Mineral Density During Allendronate Therapy are Associated with a Lower Risk of New Vertebral Fractures in Women with Postmenopausal Osteoporosis," Arthritis & Rheumatism, 42(6):1246-1254.

Holford, N. H., et al., (1981) "Understanding the Dose-Effect Relationship: Clinical Application of Pharmacokinetic-Pharmacodynamic Models," Clin. Parmacokinet. 6:429-453.

Horig, H. and Pullman, W., "From Bench to Clinic and Back: Perspective on the 1st IQPC Translational Research Conference," J Translational Medicine 2(44):1-8 (2004).

Horwitz, M. J., et al., (2010) "Parathyroid Hormone-Related Protein for the Treatment of Postmenopausal Osteoporosis: Defining the Maximal Tolerable Dose," J. Clin. Endocrinol. Metab. 95:1279-1287.

Horwitz, M. J., et al., (2013) "A Comparison of Parathyroid Hormone-Related Protein (1-36) and Parathyroid Hormone (1-34) on Markers of Bone Turnover and Bone Density in Postmenopausal Women: The PrOP Study," J. Bone Min. Res. 28(11):2266-2276.

Horwitz, M.J. et al., (2003) "Direct Comparison of Sustained Infusion of Human Parathyroid Hormone-Related Protein-(1-36) [hPTHrP-(1-36)] Versus hPTH-(1-34) on Serum Calcium, Plasma 1,25-Dihydroxyvitamin D Concentrations, and Fractional Calcium Excretion in Healthy Human Volunteers," J Clin Endocrinol Metab, 88(4):1603-1609.

Horwitz, M.J. et al., (2003) "Short-Term, High-Dose Parathyroid Hormone-Related Protein as a Skeletal Anabolic Agent for the Treatment of Postmenopausal Osteoporosis," J Clin Endocrinol Metab, 88(2):569-575.

Horwitz, M.J. et al., (2005) "Continuous PTH and PTHrP Infusion Causes Suppression of Bone Formation and Discordant Effects on 1,25(OH)2 Vitamin D," J Bone Miner Res, 20(10):1792-1803.

Horwitz, M.J. et al., (2006) "Safety and Tolerability of Subcutaneous PTHrP(1-36) in Healthy Human Volunteers: a Dose Escalation Study," Osteoporos Int, 17:225-230.

International Union of Pure and Applied Chemistry (1984) "Nomenclature and Symbolism for Amino Acids and Peptides," Pure Appl Chem 56:595-624.

Jeselsohn, R., et al., (2015) "ESR1 Mutations as A Mechanism for Acquired Endocrine Resistance in Breast Cancer," Nat. Rev. Clin. Oncol. 12:573-583.

Jorgensen, L., et al., (2009) "Recent trends in stabilising peptides and proteins in pharmaceutical formulation—consideration in the choice of excipients," Expert Opin Drug Delivery, 6(11):1219-1230.

Kalluri, H. and Banga, A. K., "Transdermal Delivery of Proteins," AAPS PharmSciTech, 12(1) 431-441 (published online Mar. 3, 2011).

Kamberi, M., (2005) The effects of sucrose on stability of human brain natriuretic peptide [hBNP(1-32)] and human parathyroid hormone (hPTH(1-34)], J Peptide Res, 66:348-356.

(56) References Cited

OTHER PUBLICATIONS

Katikaneni, S., et al., (2010) "Transdermal delivery of ~13 kDa protein—an in vivo comparison of physical enhancement methods", J Drug Targeting, 18(2):141-147.
Keaveny, T.M., et al., (2012) "Femoral Strength in Osteoporotic women Treated With Teriparatide or Alendronate," Bone 50:165-170.
Kemppainen et al., "Distinguishing Androgen Receptor Agonists and Antagonists: Distinct Mechanisms of Activationby Medroxyprogesterone Acetate and Dihydrotestosterone," Molecular Endocrinology, 1999, vol. 13, No. 3, 440-454.
Kenan, Y., et al., "Comparison of Transdermal and Subcutaneous Teriparatide Pharmacokinetics and Pharmacodynamics of Bone Markers in Postmenopausal Women," Poster Session, Presentation No. FR0376 of the ASBMR 2010 Annual Meeting, (Oct. 15-16, 2010).
Kharkevich, D.A., Pharmacotherapeutic effect as a function of properties . . . ; Pharmacology, Tenth Edition, 2008, pp. 66-67 and English Translation.
Kim et al., "The 4-Para Substituent of S-3-(phenoxy)-2-hydroxy-2-methyl-N(4-nitro-3-trifluoromethyl-phenyl)-propionamides is a Major Structural Determinant of In Vivo Disposition and Activity of Selective Androgen Receptor Modulators," American Society for Pharmacology and Experimental Therapeutics, 2005, 42 pages.
Kinoyama et al., "(+)-(2R,5S)-4-[4-Cyano-3-(trifluotomethyl)phenyl]-2,5-dimethyl-N46-(trifluoromethyppyridin-3-yl]piperazine-a-carboxamide (YM580) as an Orally Potent and Peripherally Selective Nonsteroidal Androgen Receptor Antagonist," J. Med. Chem., 2006, 49, 716-726.
Korean Intellectual Property Office, International Search Report for PCT/US2006/044921 mailed Mar. 15, 2007.
Kronenberg, H. M., (2006) "PTHrP and Skeletal Development," Ann. N.Y. Acad. Sci. 1068:1-13.
Krstenansky, J.L. et al., (1995) "RS-66271: Molecular Design and in vivo Bone Anabolic Activity," Peptides 1994, Proceedings of the European Peptide Symposium, 23rd, Braga, Port., Sep. 4-10, 1994:133-134.
Lamb, R., et al., (2013) "Cell Cycle Regulators Cyclin D1 and CDk4/6 Have Estrogen Receptor-Dependent Divergent Functions in Breast Cancer Migration and Stem Cell-Like Activity," Cell Cycle 12(15):2384-2394.
Lange, U., et al., (2005) "Increase in Bone Mineral Density of Patients with Rheumatoid Arthritis Treated with Anti-TNF-Alpha Antibody: A Prospective Open-Label Pilot Study," Rheumatol. 44:1546-1548.
Lanter, J.C., et al., (2007) "The Discovery of a Potent Orally Efficacious Indole Androgen Receptor Antagonist Through in vivo Screening," Bioorganic & Medicinal Chem Letters, 17:123-126.
Leder, B. Z., et al., (2013) "Two Years of Denosumab and Teriparatide Administration n Postmenopausal Women with Osteoporosis (The DATA Extension Study): A Randomized Controlled Trial," Lancet 382(9886):50-56.
Legrand, J.J. et al., (2001) "BIM-44058, a Novel PTHrP Analog, Does Not Increase Total Plasma Calcium in Cynomolgus Monkeys at an Effective Pharmacological Dose," Twenty-Third Annual Meeting of the American Society of Bone and Mineral Research, Phoenix, Arizona, USA, Oct. 12-16, 2001, J Bone Miner Res, (Abstract M454) 16 (Suppl. 1):S539.
Legrand, J.J. et al., (2002) "BIM-44058, A Novel PTHrP Analog, Restores BMD by Selectively Increasing Bone Formation in Old Ovariectomized, Osteopenic Cynomolgus Monkeys," S20, Abstract for the World Congress on Osteoporosis meeting held on May 10-14, 2002, Lisbon, Portugal (Abstract P53SA), Osteoporos Int 13(1).
Legrand, J.J., et al., (2003) "Use of Biochemical Markers to Monitor Changes in Bone Turnover in Cynomolgus Monkeys," Biomarkers, 8(1):63-77.
Lloyd, M.E., et al., (1996) "Relation Between Insulin-Like Growth Factor-I Concentrations, Osteoarthritis, Bone Density, and Fractures in the General Population: the Chingford Study," Ann Rheum Dis, 55:870-874.
Loprinzi, C.L., et al., "Management of Hot Flashes in Breast-Cancer Survivors," The Lancet Oncology, 2(4):199-204 (Apr. 2001).
Ma et al., "Raloxifene and teriparatide (hPTH 1-34) have complementary effects on the osteopenic skeleton of ovariectomized rats," J Bone Miner Metab, 2005, 23[Suppl]:62-68.
Ma, Y. L., et al., (2011) "Comparative Effects of Teriparatide and Strontium Ranelate in the Periosteum of Iliac Crest Biopsies in Postmenopausal Women with Osteoporosis," Bone 48:972-978.
Ma, Y.L., et al., (2014) Effects of Teriparatide on Cortical Histomorphometric Variables in Postmenopausal Women With or Without Prior Alendronate Treatment. Bone 59:139-147.
Maclean, C., et al., (2008) "Systematic Review: Comparative Effectiveness of Treatments to Prevent Fractures n Men and Women with Low Bone Density or Osteoporosis," Ann. Intern. Med. 148:197-213.
Mannstadt, M. et al., (1999) "Receptors for PTH and PTHrP: Their Biological Importance and Functional Properties," American Physiological Society: Invited Review:F665-F675.
Manolagas, S.C. et al., (1999) "Opposite Effects of Estrogen on the Life Span of Osteoblasts/Osteocytes Versus Osteoclasts In Vitro: An Explanation of the Imbalance between Formation and Resorption in Estrogen Deficiency," J Bone Mineral Res, 14(Supp 1)(Abstract 1147):S169.
Manolagas, S.C., (1999) "Activators of Non-Genomic Estrogen-Like Signalling (ANGELS): a Novel Class of Small Molecules with Bone Anabolic Properties," J Bone Mineral Res, 14(Supp 1)(Abstract 1191):S180.
Marino, M. et al., "Estrogen Signaling Multiple Pathways to Impact Gene Transcription," Current Genomics, 2006, 7, 497-508.
Martin, T.J., (2005) "Osteoblast-derived PTHrP is a Physiological Regulator of Bone Formation," J Clin Invest, 115(9):2322-2324.
Martinborough et al., "Substituted 6-(1-Pyrrolidine)quinolin-2(1H)-ones as Novel Selective Androgen Receptor Modulators," Journal of Medicinal Chemistry, 2007, vol. 50, No. 21, 5049-5052.
McGinley et al., "Circumventing Anti-Androgen Resistance by Molecular Design," J. Am. Chem. Soc., 2007, 129, 3822-3823.
Medi, B.M. and Singh, J., (2003) "Electronically Facilitated Transdermal Delivery of Human Parathyroid Hormone (1-34)," International J Pharmaceutics, 263:25-33.
Mesu, J. G., et al., (2005) "Infrared and Raman Spectroscopic Study of pH-induced Structural Changes of L-histidine in Aqueous Environment," Vibrational Spectroscopy, 39:114-125.
Miao, D., et al., (2004) "Skeletal Abnormalities in Pth-Null Mice are Influenced by Dietary Calcium," Endocrinology 145:2046-2053.
Miao, D., et al., (2005) "Osteoblast-derived PTHrP is a Potent Endogenous Bone Anabolic Agent that Modifies the Therapeutic Efficacy of Administered PTH 1-34," J Clin Invest, 115(9):2402-2411.
Miller et al., "Synthesis of potent, substitute carbazoles as selective androgen receptor modulators (SARMs)" Bioorganic & Medicinal Chemistry Letters, 2010, 20, 7516-7520.
Miller, C.P., et al., "Design, Synthesis, and Preclinical Characterization of the Selective Androgen Receptor Modulator (SARM) RAD140," ACS Med Chem Lett, 2(2):124-129, DOI: 10.1021/ml1002508 (Dec. 2, 2010).
Miller, P. D., et al., (2005) "Monthyl Oral Ibandronate Therapy in Postmenopausal Osteoporosis: 1-Year Results from the MOBILE Study," J. Bone Min. Res. 20(8):1315-1322.
Mitchell, H.J., et al., Design, Synthesis, and Biological Evaluation of 16-Substituted 4-Azasteroids as Tissue-Selective Androgen Receptor Modulators (SARMs), J Med Chem, 52(15):4578-81 (2009).
Mohler, M.L., et al., "Nonsteroidal Selective Androgen Receptor Modulators (SARMs): Dissociating the Anabolic and Androgenic Activities of the Androgen Receptor for Therapeutic Benefit," J Med Chem, 52(12):3597-617 (Jun. 25, 2009).
Morris, J.J., et al., (1991) "Non-steroidal Antiandrogens. Design of Novel Compounds Based on an Infrared Study of the Dominant

(56) References Cited

OTHER PUBLICATIONS

Conformation and Hydrogen-Bonding Properties of a Series of Anilide Antiandrogens," J Med Chem, 34:447-455.
Moser, C.L., and Meyer, B.K., (2011) "Comparison of Compendial Antimicrobial Effectiveness Tests: A Review," AAPS PharmaSciTech, 12:222-226.
Murrills, R.J. et al., (2004) "In vitro and in vivo Activities of C-Terminally Truncated PTH Peptides Reveal a Disconnect Between cAMP Signaling and Functional Activity," Bone, 35:1263-1272.
Narayanan, R., et al., (2008) "Selective Androgen Receptor Modulators in Preclinical and Clinical Development," Nuclear Receptor Signaling, 6:e010.
Neer, R.M. et al., (2001) "Effect of Parathyroid Hormone (1-34) on Fractures and Bone Mineral Density in Postmenopausal Women with Osteoporosis," N Engl J Med, 344(19):1434-1441.
Ng et al., "Synthesis and SAR of potent and selective androgen receptor antagonist: 5,6-Dichloro-benzimidazole derivatives," Bioorganic & Medicinal Chemistry Letters 17, 2007, 17, 784-788.
Ng, R.A., "Synthesis of Potent and Tissue-Selective Androgen Receptor Modulators (SARMs): 2-(2,2,2)-Trifluoroethylbenzimidazole Scaffold," Bioorganic & Medicinal Chemistry Letters, 17:1784-1787 (2007).
Nishiyama, K. K., et al., (2014) "Teriparatide Increases Strength of the Peripheral Skeleton in Premenopausal Women with Idiopathic Osteoporosis: A Pilot HR-pQCT Study," J. Clin. Endocronol. Metab. 99:2418-2425.
O'Dea, L.S., et al., "BA058, a Novel Analog of Human Parathyroid Hormone-Related Peptide (PTHrP), Induces Evidence of Bone Formation without Evidence of Bone Resorption over 7 Days of Exposure," The Endocrine Society's 89th Annual Meeting held on Jun. 2-5, 2007, (Abstract) P2-137:361 (published on May 11, 2007).
Obaidi, M., et al., (2010) "Pharmacokinetics and Pharmacodynamic of Subcutaneously (SC) Administered Doses of BA058, A Bone Mass Density Restoring Agent in Healthy Postmenopausal Women," AAPS(abstract): W5385.
Odgaard, A. and Gundersen, H.J.G., (1993) "Quantification of Connectivity in Cancellous Bone, with Special Emphasis on 3-D Reconstructions," Bone, 14:173-182.
Odgaard, A., (1997) "Three-Dimensional Methods for Quantification of Cancellous Bone Arhitecture," Bone, 20(4):315-328.
Oei, L., et al. (2013) "High Bone Mineral Density and Fracture Risk in Type 2 Diabetes as Skeletal Complications of Inadequate Glucose Control," Diabetes Care 36:1619-1628.
Okazaki, M., et al., (2008) "Prolonged signaling at the parathyroid hormone receptor by peptide ligands targeted to a specific receptor conformation," PNAS, 105(43):16525-16530.
Ornoy et al., "Osteoporosis: Animal Models for the Human Disease," Animal Models of Human Related Calcium Metabolic Disorders, 1995, Chapter 5, 105-126.
Ostrowski et al., "Pharmacological and X-Ray Structural Characterization of a Novel Selective Androgen Receptor Modulator: Potent Hyperanabolic Stimulation of Skeletal Muscle with Hypostimulation of Prostate in Rats," Endocrinology, 2007, 148(1):4-12.
Pandya, K.J., et al., "Pilot Study Using Gabapentin for Tamoxifen-Induced Hot Flashes in Women with Breast Cancer," *Breast Cancer Research and Treatment*, 83:87-89 (2004).
Papapoulos, S. E., (2011) "Use of Biophosphonates in the management of postmenopausal osteoporosis," Ann. N.Y. Acad. Sci. 1218:15-32.
Patel, R.M., (2010) "Parenteral Suspension: An Overview," Int J Curr Pharm Res, 2(3):4-13.
Patsch, J. M., et al., (2013) "Increased Cortical Porosity in Type-2 Diabetic Postmenopausal Women with Fragility Fractures," J. Bone Miner. Res. 28(2):313-324.
Paudel, K.S., et al., (2010) "Challenges and opportunities in dermal/transdermal delivery," Ther Deliv, 1(1):109-131.
PCT/US2007/014598 Notification Concerning Transmittal of International Preliminary Report on Patentability (Chapter I of the Patent Cooperation Treaty) from International Application No. PCT/US2007/014598 dated Jan. 15, 2009.

Pellegrini, M. et al., (1997) "Conformational Studies of RS-66271, an Analog of Parathyroid Hormone-Related Protein with Pronounced Bone Anabolic Activity," J Med Chem, 40(19):3025-3031.
Pellegrini, M. et al., (1998) "Addressing the Tertiary Structure of Human Parathyroid Hormone-(1-34)," J Biol Chem, 273(17):10420-10427.
Pellegrini, M. et al., (1999) "RS-66271, a Clinical Candidate Derived from Parathyroid Hormone Related Protein: the Role of Enhanced Amphiphilic Helicity," Peptipes: Frontiers of Peptide Science, Proceedings of the American Peptide Symposium, 15th, Nashville, Jun. 14-19, 1997, 392-393.
Perumal, O., et al., (2013) "Turning Theory into Practice: The Development of Modern Transdermal Drug Delivery systems and Future Trends," Skin Pharmacol Physiol, 26:331-342.
Pioszak, A. A., et al., (2009) "Structural Basis for Parathyroid Hormone-Related Protein Binding to the Parathyroid Hormone Receptor and Design of Conformation-Selective Peptides," J. Biol. Chem. 284(41):28382-28391.
Piu et al., "Pharmacological characterization of AC-262536, a novel selective androgen receptor modulator," Journal of Steroid Biochemistry & Molecular Biology, 2008, 109, 129-137.
Plotkin, H. et al., (1998) "Dissociation of Bone Formation from Resorption during 2-Week Treatment with Human Parathyroid Hormone-Related Peptide-(1-36) in Humans: Potential as an Anabolic Therapy for Osteoporosis," J Clin Endocrinol Metab, 83(8):2786-2791.
Recker, R. R., et al., (2009) "Comparative Effects of Teriparatide and Strontium Ranelate on Bone Biopsies and Biochemical Markers of Bone Turnover in Postmenopausal Women with Osteoporosis," J. Bone Min. Res. 24(8):1358-1368.
Riedmaier et al., "Influence of testosterone and a novel SARM on gene expression in whole blood of *Alacaca fascicularis*," Journal of Steroid Biochemistry and Molecular Biology, 2009, 114, 167-173.
Rochira, V., et al., (2006) "Osteoporosis and Male Age-Related Hypogonadism: Role of Sex Steroids on Bone (patho)Physiology," Eur J Endocrinol, 154:175-185.
Roe, E.B. et al., (1999) "Parathyroid Hormone 1-34 (hPTH 1-34) and Estrogen Produce Dramatic Bone Density Increases in Postmenopausal Osteoporosis—Results from a Placebo-Controlled Randomized Trial," J Bone and Mineral Res, 14(Supp 1)(Abstract 1019):S137.
Rogol, A. D., "Causes of Short Stature," UptoDate, pp. 1-15, accessed May 2, 2016 at http://www.uptodate.com/contents/causes-of-short-stature?topicKey=PEDS%2F5832&elaps . . . .
Rosen, C.J., (2005) "Clinical Practice. Postmenopausal Osteoporosis," N. Engl. J. Med. 353(6):595-603.
Rosenblatt, M., (2009) "When Two Keys Fit One Lock, Surprises Follow", Nature Chem. Biol. 5(10):707-708.
Salvatii et al., "Identification and optimization of a novel series of [2.2.1]-oxabicyclo imide-based androgen receptor antagonist," Bioorganic & Medicinal Chemistry Letters, 2008, 1910-1915.
Schafer et al., "Failure is an option learning from unsuccessful proof-of-concept trials," Drug Discovery Today, 2008, vol. 13, No. 21/22, 913-916.
Sebba, A. I., (2008) "Significance of a Decline in Bone Mineral Density While Receiving Oral Biphosphonate Treatment," Clin. Ther. 30(3):443-452.
Sebba, A. I., et al., (2004) "Response to Therapy with Once-Weekly Alendronate 70 mg Compared to Once-Weekly Risedronate 35 mg in the Treatment of Postmenopausal Osteoporosis," Curr. Med. Res. Opin. 20(12):2031-2041.
Sharon Laboratories data Sheet "Parabens.".
Silva, B. C., et al., (2014) "Trabecular Bone Score: A Noninvasive Analytical Method Based Upon the DXA Image," J. Bone Min. Res. 29(3):518-530.
Silverman, S.L., et al., (2008) "Recommendations for the Clinical Evaluation of Agents for Treatment of Osteoporosis: Conscensus of an Expert Panel Representing the American Society for Bone and Mineral Research (ASBMR), the International Society for Clinical Densitometry (ISCD), and the National Osteoporosis Foundation (NOF)," J. Bone Miner. Res. 23(1):159-165.

(56) References Cited

OTHER PUBLICATIONS

Singapore Intellectual Property Office, Search Report and Written Opinion for 2013078324 completed Jul. 15, 2015.
Singapore Intellectual Property Office, Written Opinion for 2013078324 completed Mar. 5, 2016.
Smith, S. Y., et al., (2013) "Eldecalcitol, a Vitamin D Analog, Reduces Bone Turnover and Increases Tabecular and Cortical Bone Mass, Density, and Strength in Ovariectomized Cynomolgus Monkeys," Bone 57:116-122.
Stearns, V., et al., "A Pilot Trial Assessing the Efficacy of Paroxetine Hydrochloride (Paxil ) in Controlling Hot Flashes in Breast Cancer Survivors," *Annals of Oncology*, 11:17-22 (2000).
Stellman, J.T., (2009) "Development, Production and Characterization of Plastic Hypodermic Needles," MS Thesis, Georgia Institute of Technology, pp. 1-150.
Storage Conditions—Peptides International, pepnet.com/ShoppingUsers/StorageStability.aspx; Aug. 20, 2012.
Sundar et al., "Spironolactone, a possible selective androgen receptor modulator, should be used with caution in patients with metastatic carcinoma of the prostate," BJM Case Rep, 2012, Abstract.
Suzuki, Y., et al., (2001) "Iontophoretic Pulsatile Transdermal Delivery of Human Parathyroid Hormone (1-34)," J Pharmacy and Pharmacology, 53(9):1227-1234.
Thiel, "Structure-aided drug design's next generation," Nature Biotechnology, 2004, vol. 22, No. 5, 513-519.
Toniolo, C., (1993) "Cα,α-Symmetrically Disubstituted Glycines: Useful Building Blocks in the Design of Conformationally Restricted Peptides", Janssen Chim. Acta, 11:10-16.
Tsai, J.N., et al., (2013) "Comparative Effects of Teriparatide, Denosumab, and Combination Therapy on Peripheral Compartmental Bone Density, Microarchitecture: the DATA-HRpQCT Study," Annual Meeting of the American Society of Bone and Mineral Research, Baltimore, MD.
Tsai, J.N., et al., (2015) "Comparative Effects of Teriparatide, Denosumab, and Combination Therapy on Peripheral Compartmental Bone Density, Microarchitecture, and Estimated Strength: the DATA-HRpQCT Study," J. Bone Miner. Res. 30(1):39-45.
Tucker, H., et al., (1988) "Nonsterodial Antiandrogens, Synthesis and Structure-Activity Relationships of 3-Substituted Derivatives of 2-Hydroxypropionanilides," J Med Chem, 31:954-959.
U.S. Department of Health and Human Services, Bone Health and Oseoporosis: A Report of the Surgeon General, Rockville, MD (2004).
United States Patent and Trademark Office, International Preliminary Report on Patentability (Ch I) for PCT/US2010/030480 issued Oct. 11, 2011.
United States Patent and Trademark Office, International Preliminary Report on Patentability (Ch I) for PCT/US2011/023768 issued Aug. 7, 2012.
United States Patent and Trademark Office, International Preliminary Report on Patentability (Ch I) for PCT/US2012/034510 issued Mar. 18, 2014.
United States Patent and Trademark Office, International Search Report and Written Opinion for PCT/US16/20787 mailed Jul. 22, 2016.
United States Patent and Trademark Office, International Search Report and Written Opinion for PCT/US2012/34510 completed Aug. 11, 2012 and mailed Aug. 31, 2012.
United States Patent and Trademark Office, International Search Report and Written Opinion for PCT/US17/26462 completed Jun. 6, 2017 and mailed Jul. 3, 2017.
United States Patent and Trademark Office, International Search Report and Written Opinion for PCT/US2009/054348 mailed Dec. 9, 2009.
Unnanumtana, A., et al., (2010) "Current Concepts Review: The Assessment of Fracture Risk," J. Bone Joint Surg. Am. 92:743-753.
Vajda et al., "Pharmacokinetics and Pharmacodynamics of LGD-3303 [9-Chloro-2-ethyl-1-methyl-3-(2,2,2-trifluoroethyl)-3H-pyrrolo-[3,2-f]quinolin-7(6H)-one], an Orally Available Nonsteroidal-Selective Androgen Receptor Modulator," The Journal of Pharmacology and Experimental Therapeutics, 2009, vol. 328, No. 2, 663670.
Van Der Maaden, K., et al., (2012) "Microneedle technologies for (trans)dermal drug and vaccine delivery", J Controlled Release, 161:645-655.
Van Oeveren et al., "Novel selective androgen receptor modulators: SAR studies on 6-bisalkylamino-2-quinolinones," Bioorganic & Medicinal Chemistry Letters, 2007, 17:1527-1531.
Vickery, B.H. et al., (1996) "RS-66271, a C-Terminally Substituted Analog of Human Parathyroid Hormone-Related Protein (1-34), Increases Trabecular and Cortical Bone in Ovariectomized, Osteopenic Rats," J Bone Miner Res, 11(12):1943-1951.
Wermuth, C. G. editor; "The Practice of Medicinal Chemistry", book two of two, 347-365, Kabushiki Kaisha Technomics, 1999.
Wright, P., "Transdermal Drug Delivery Looks for New Frontiers," Pharmaceutical Commerce, Feb. 26, 2013.
Yates, J. et al., (2014) "OR22-4: A Transdermal Patch Delivering the PTHrP1-34 Analog, Abaloparatide (BA058), Dose-Dependently Increases Spine and hip BMD Compared to Placebo," Endocrine Society's 96th Annual Meeting and Expo, Chicago, IL Jun. 21-24, 2014.
Zeng, C., et al., "Efficient Synthesis of (2R,3S)-2-amino-3-(benzyloxy)-4,4,4-trifluorobutanoic acid (4,4,4-trifluoro-OBn-D-allothreonine)," Tetrahedron Letters, 51:53615363 (2010).
Zhang et al., "Synthesis and SAR of novel hydantoin derivatives as selective androgen receptor modulators," Bioorganic & Medicinal Chemistry Letters, 2006, vol. 16, Issue 22, 5763-5766.
Zhang, X., et al., "Design, Synthesis, and in Vivo SAR of a Novel Series of Pyrazolines as Potent Selective Androgen Receptor Modulators," J Med Chem, 50(16):3857-3869 (2007).
Zhang, Y., et al., (2009) "Inhibition of Peptide Acylation in PLGA Microspheres with Water-Soluble Divalent Cationic Salts," Pharm. Res. 26(8):1986-1994.
Zizic, T.M., et al., (2004) "Pharmacologic Prevention of Osteoporotic Fractures," Am Fam Physician, 70:1293-1300.
Bryn, S, et al., Pharmaceutical Solids: A Strategic Approach to Rgulatory Considerations, Pharmaceutical Research, vol. 12, No. 7, pp. 945-954, Plenum Publishing Corporation 1995.
Kawaguchi, et a., Drug and Crystal Polymorphism, Journal of Human Environmental Engineering, vol. 4, No. 2, 2002.
Lee, E.H., A practical guide to pharmaceutical polymorph screening & selection, Asian Journal of Pharmaceutical Sciences, ScienceDirect, Elsevier B.V.,2014.
Pharmaceutical Affairs Bureau Notification No. 568, Setting of Standard and Test Method of New Drugs, May 1, 2013.
Takata, N., API Form Screening and Selection in Drug Discovery Stage, Pharm Stage, vol. 6, No. 10, 2007.
Yamano, M., Approach to Crystal Polymorph in Process Research of New Drug, vol. 65, No. 9, The Society of Synethetic Organic Chemistry, 2007.
European 24161402.3 Search Report dated Dec. 16, 2024.
Bavin, Polymorphism in Process Development; Chemistry & Industry, vol. 21, pp. 527-529, Aug. 21, 1989.
Grunenberg, A., Polymorphie and Thermische Analyse Pharmazeutisher Wirkstoffe; Pharmazie in unserer Zeit, No. 5, pp. 224-231, 1997.
Masum, Z.U., et al., Stability & Polymorphic Characterization of Elacestrant Dihydrochloride; Preprint (Version 1), Jun. 16-17, 2024.
T-0041/17 3.3.02 Board of Appeals of the European Patent Office, Jan. 14, 2020.
T-0777/08 3.3.01 Board of Appeals of the European Patent Office, May 24, 2011.

\* cited by examiner

POLYMORPHIC FORMS OF RAD1901-2HCL

PRIORITY CLAIM

Cross Reference to Related Application

This application is a Continuation Application of U.S. patent application Ser. No. 17/475,018, filed Sep. 14, 2021, which is a Continuation Application of U.S. patent application Ser. No. 16/921,684, filed Jul. 6, 2020, now U.S. Pat. No. 11,148,996, which is a Divisional Application of U.S. patent application Ser. No. 16/456,314, filed Sep. 13, 2019, now U.S. Pat. No. 10,745,343, which is a Divisional Application of U.S. patent application Ser. No. 15/863,850, filed Jan. 5, 2018, now U.S. Pat. No. 10,385,008, which claims the benefit under 35 U.S.C. § 119 of U.S. Provisional Patent Application No. 62/442,921, filed Jan. 5, 2017. The entire contents of the aforementioned applications are hereby incorporated by reference herein in their entirety, including drawings.

BACKGROUND

RAD1901 is a selective estrogen receptor down-regulator/degrader, or SERD, that crosses the blood-brain barrier and is particularly useful for the treatment of metastatic breast cancer. RAD1901 has been shown to bind with good selectivity to the estrogen receptor (ER) and to have both estrogen-like and estrogen-antagonistic effect in different tissues. In many cancers, hormones, like estrogen, stimulate tumor growth, and thus a desired therapeutic goal is to block this estrogen-dependent growth while inducing apoptosis of the cancer cells. SERDs have the potential to be an emerging class of endocrine therapies that could directly induce ER degradation, thus potentially enabling them to remove the estrogen growth signal in ER-dependent tumors without allowing ligand-independent resistance to develop.

SUMMARY OF THE INVENTION

Various polymorphic forms of RAD1901-2HCl are disclosed herein, along with pharmaceutical compositions thereof, preparation methods thereof, and uses thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

I. Polymorphic Forms of RAD1901-2HCl

Figure 1:
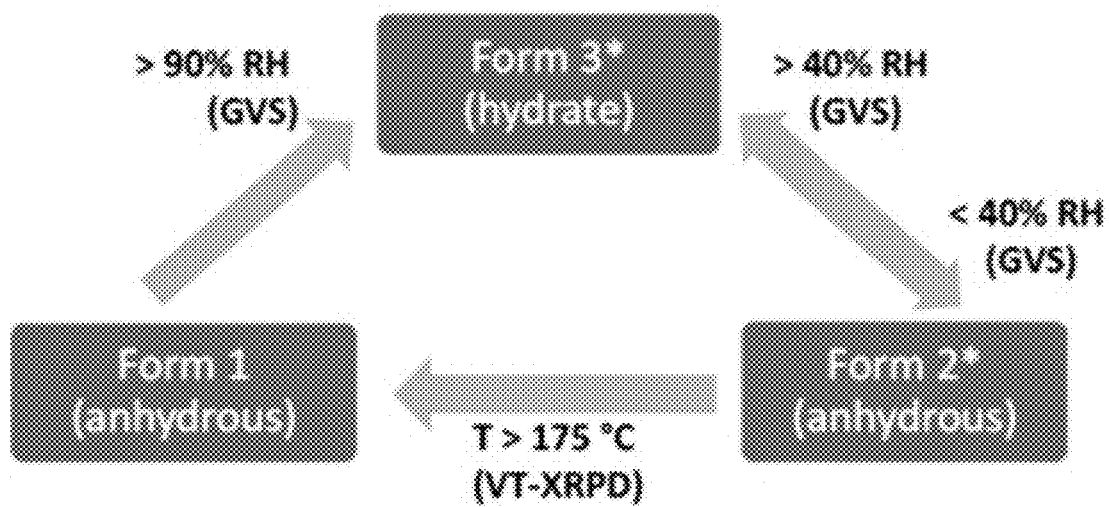
FIG. 1: Conversion among Forms 1, 2, and 3 of RAD1901-2HCl.

As set forth in the Examples section below, three crystalline and amorphous forms of RAD1901-2HCl were prepared and characterized.

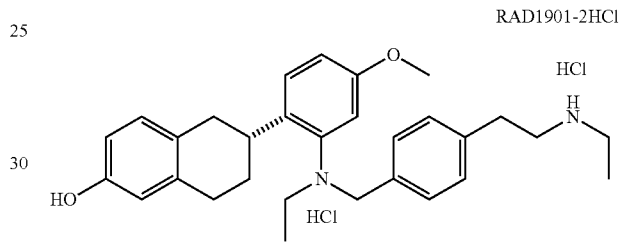

The definitions provided herein are meant to clarify, but not limit, the terms defined. If a term used herein is not specifically defined, such term should not be considered indefinite. Rather, terms are used within their accepted meanings.

As used herein, RAD1901-2HCl refers to a salt form wherein the molar ratio of RAD1901 and HCl is approximately 2, e.g., from about 1.7 to about 2.1, or from 1.8 to about 2.0. Small changes in the amount of assayed HCl can be attributed to, without limitation, measurement variability and loss of small amounts of HCl through storage and/or processing.

As used herein, "crystalline" refers to a solid having a highly regular chemical structure. In particular, a crystalline free base or salt form may be produced as one or more single crystalline forms. For the purposes of this application, the terms "crystalline form", "single crystalline form" and "polymorph" are synonymous; the terms distinguish between crystals that have different properties (e.g., different XRPD patterns and/or different DSC scan results). The term "polymorph" includes pseudopolymorphs, which are typically different solvates of a material, and thus their properties differ from one another. Thus, each distinct polymorph and pseudopolymorph of a free base or salt form is considered to be a distinct single crystalline form herein.

The term "substantially crystalline" refers to forms that may be at least a particular weight percent crystalline. Particular weight percentages are 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, substantially crystalline refers to a free base or salt form that is at least 70% crystalline. In other embodiments, substantially crystalline refers to a free base or salt form that is at least 90% crystalline.

As used herein, "amorphous" refers to a solid material comprising non-crystalline materials. In certain embodiments, an amorphous sample of a material may be prepared by lyophilization of a mixture of the material with a solvent, wherein the mixture may be homogeneous (e.g., solution) or heterogeneous (e.g., a slurry).

The term "substantially free" refers to forms and compositions that may be at least a particular weight percent free of impurities and/or crystalline compound. Particular weight percentages are 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 60% and 100% free of impurities and/or crystalline compound. In some embodiments, substantially free refers to a free base or salt form that is at least 70% pure. In other embodiments, substantially crystalline refers to a free base or salt form that is at least 90% pure. In other embodiments, substantially free of crystalline compound refers to a composition having less than about 30%, less than about 20%, less than about 15%, less than about 10%, less than about 5%, less than about 1% of crystalline compound.

The term "hydrate" is a solvate wherein the solvent molecule is $H_2O$ that is present in a defined stoichiometric or non-stoichiometric amount. Stoichiometric solvates may, for example, include hemihydrate, monohydrate, dihydrate, or trihydrate forms, among others. Non-stoichiometric solvates may include, for example, channel hydrates, including where water content may change depending on humidity of the environment.

The term "solvate or solvated" means a physical association of a compound, including a crystalline form thereof, of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, a hydrate, ethanolates or a methanolate.

The term "stable" in the context of a polymorphic form disclosed herein refers to the stability of the polymorphic form relative to heat and/or humidity.

The relationship among the three crystalline forms of RAD1901 is provided in FIG. 1.

As used herein, crystalline forms of RAD1901-2HCl are referred to as Forms 1, 2, and 3, respectively. Forms 1 and 2 are anhydrous forms of RAD1901-2HCl, and Form 3 is a hydrated form of RAD1901-2HCl. Forms 1, 2, and 3 showed different X-ray powder diffraction (XRPD) patterns.

Sample 1 refers to an initially uncharacterized batch of RAD1901-2HCl that was subsequently determined to be predominately Form 1. Sample 2 refers to an initially uncharacterized batch of RAD1901-2HCl that was subsequently determined to be a mixture of Form 2 and Form 3

GVS experiments showed that Form 2 was hygroscopic with a mass uptake from 0-40% RH, and the mass uptake plateaued above 40% RH. Thus, an equilibrium existed between the anhydrous Form 2 and hydrate Form 3 at near ambient RH. Anhydrous Form 1 demonstrated low hygroscopicity between 0-90% RH, and started converting to the hydrate Form 3 at above 90% RH.

In many embodiments disclosed herein, RAD1901-2HCl is disclosed as having a crystalline structure.

In certain embodiments, crystalline structures in this disclosure can be identified by having one or more characteristics peaks in an XRPD spectrum, as disclosed herein.

In some embodiments, crystalline structures in this disclosure have one or more characteristics endothermic peaks in differential scanning calorimetry, as disclosed herein.

In certain embodiments, methods of preparing and/or interconverting one or more crystalline forms of RAD1901-2HCl are provided. Further embodiments describe the conversion to, and preservation of a crystalline form of RAD1901-2HCl that has desired stability under expected storage conditions.

Certain embodiments disclosed herein provide a solid form of RAD1901-2HCl, having an X-ray powder diffraction pattern comprising a peak, in terms of 2θ, at 7.1 degrees 2θ±0.2 degrees 2θ at about relative humidity 0%, e.g., Form 1.

Certain embodiments disclosed herein provide a solid form of RAD1901-2HCl, having an X-ray powder diffraction pattern comprising a peak, in terms of 2θ, at 7.1 degrees 2θ±0.2 degrees 2θ, and/or 14.3 degrees 2θ±0.2 degree 2θ at about relative humidity 0%, e.g., Form 1.

Certain embodiments disclosed herein provide a solid form of RAD1901-2HCl, having an X-Ray powder diffraction pattern comprising at least two peaks, in terms of 2-theta, selected from the group consisting of 7.1 degrees 2θ±0.2 degree 2θ, 14.3 degrees 2θ±0.2 degree 2θ and 18.3 degrees 2θ±0.2 degree 2θ at about relative humidity 0%, e.g., Form 1.

Certain embodiments disclosed herein provide a solid form of RAD1901-2HCl, having an X-Ray powder diffraction pattern comprising at least three peaks, in terms of 2-theta, selected from the group consisting of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ and 12.0 degrees 2θ±0.2 degree 2θ, at about relative humidity 0%, e.g., Form 1.

Certain embodiments disclosed herein provide a solid form of RAD1901-2HCl, having an X-Ray powder diffraction pattern comprising at least four peaks, in terms of 2-theta, selected from the group consisting of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ, 12.0 degrees 2θ±0.2 degree 2θ, 25.1 degrees 2θ±0.2 degree 2θ and 18.9 degrees 2θ±0.2 degree 2θ, at about relative humidity 0%, e.g., Form 1.

Certain embodiments disclosed herein provide a solid form of RAD1901-2HCl, having an X-Ray powder diffraction pattern comprising at least five peaks, in terms of 2-theta, selected from the group consisting of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ, 12.0 degrees 2θ±0.2 degree 2θ, 25.1 degrees 2θ±0.2 degree 2θ, 18.9 degrees 2θ±0.2 degree 2θ, 27.2 degrees 2θ±0.2 degree 2θ and 11.0 degrees 2θ±0.2 degree 2θ, at about relative humidity 0%, e.g., Form 1.

Certain embodiments disclosed herein provide a solid form of RAD1901-2HCl, having an X-Ray powder diffraction pattern comprising at least seven peaks, in terms of 2-theta, selected from the group consisting of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ, 12.0 degrees 2θ±0.2 degree 2θ, 25.1 degrees 2θ±0.2 degree 2θ, 18.9 degrees 2θ±0.2 degree 2θ, 27.2 degrees 2θ±0.2 degree 2θ, 11.0 degrees 2θ±0.2 degree 2θ, and 16.2 degrees 2θ±0.2 degree 2θ, at about relative humidity 0%, e.g., Form 1.

Certain embodiments disclosed herein provide a solid form of RAD1901-2HCl, having an X-Ray powder diffraction pattern comprising at least eight peaks, in terms of 2-theta, selected from the group consisting of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ, 12.0 degrees 2θ±0.2 degree 2θ, 25.1 degrees 2θ±0.2 degree 2θ, 18.9 degrees 2θ±0.2 degree 2θ, 27.2 degrees 2θ±0.2 degree 2θ, 11.0 degrees 2θ±0.2 degree 2θ, and 16.2 degrees 2θ±0.2 degree 2θ, at about relative humidity 0%, e.g., Form 1.

Certain embodiments disclosed herein provide a solid form of RAD1901-2HCl, having an X-Ray powder diffraction pattern comprising at least nine peaks, in terms of 2-theta, selected from the group consisting of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ, 12.0 degrees 2θ±0.2 degree 2θ, 25.1 degrees 2θ±0.2 degree 2θ, 18.9 degrees 2θ±0.2 degree 2θ, 27.2 degrees 2θ±0.2 degree 2θ, 11.0 degrees 2θ±0.2 degree 2θ, and 16.2 degrees 2θ±0.2 degree 2θ, at about relative humidity 0%, e.g., Form 1.

Certain embodiments disclosed herein provide a solid form of RAD1901-2HCl, having an X-ray powder diffraction pattern comprising the peaks, in terms of 2-theta, of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ, 12.0 degrees 2θ±0.2 degree 2θ, 25.1 degrees 2θ±0.2 degree 2θ, 18.9 degrees 2θ±0.2 degree 2θ, 27.2 degrees 2θ±0.2 degree 2θ, 11.0 degrees 2θ±0.2 degree 2θ, and 16.2 degrees 2θ±0.2 degree 2θ, at about relative humidity 0%, e.g., Form 1.

Figure 4A:
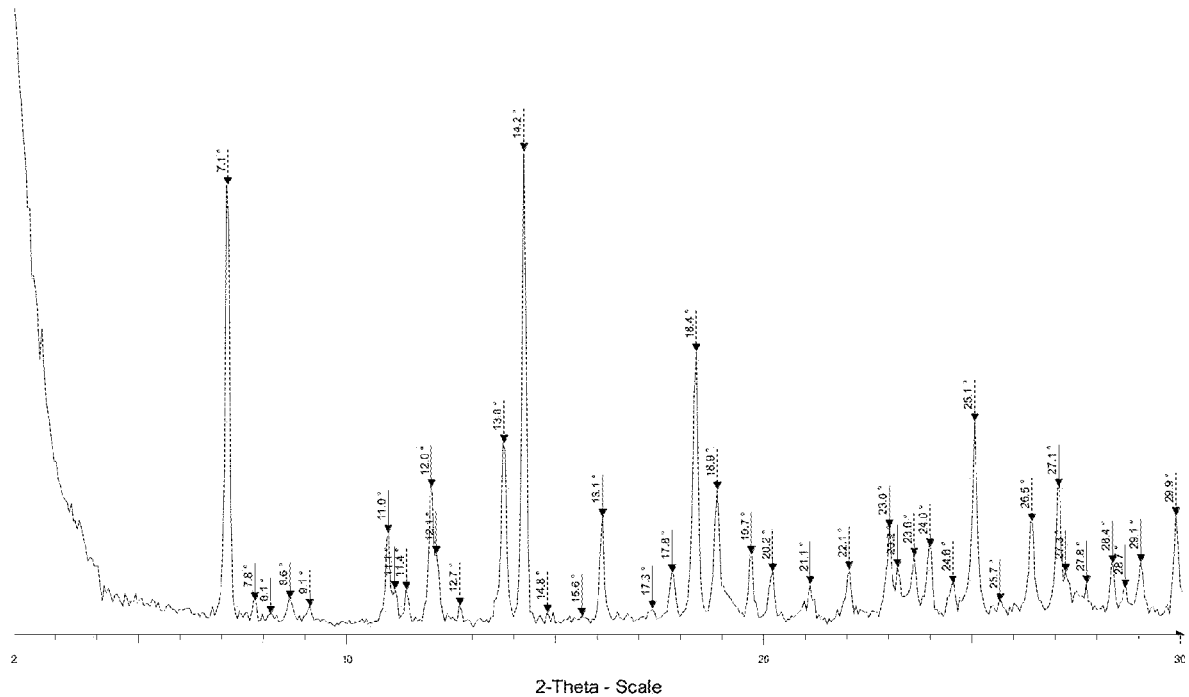
FIG. 4A: XRPD diffraction pattern of Sample 1 at ambient RH (e.g., 40-65% RH).
Figure 4B:
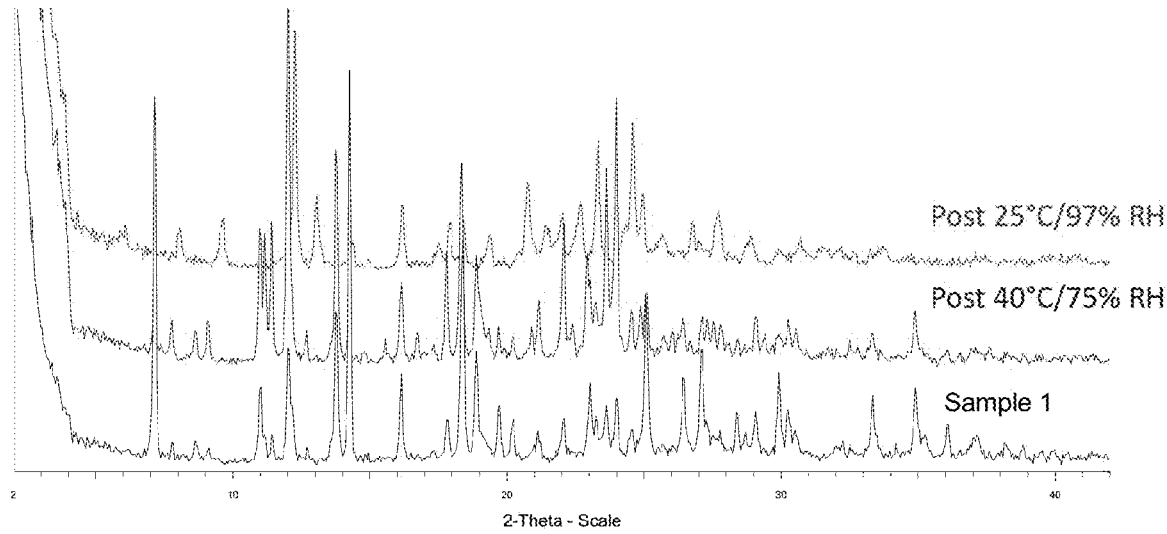
FIG. 4B: Overlay of XRPD patterns obtained for Sample 1 pre-(bottom) and post-storage (top) at elevated condition analysis.
Figure 4C:
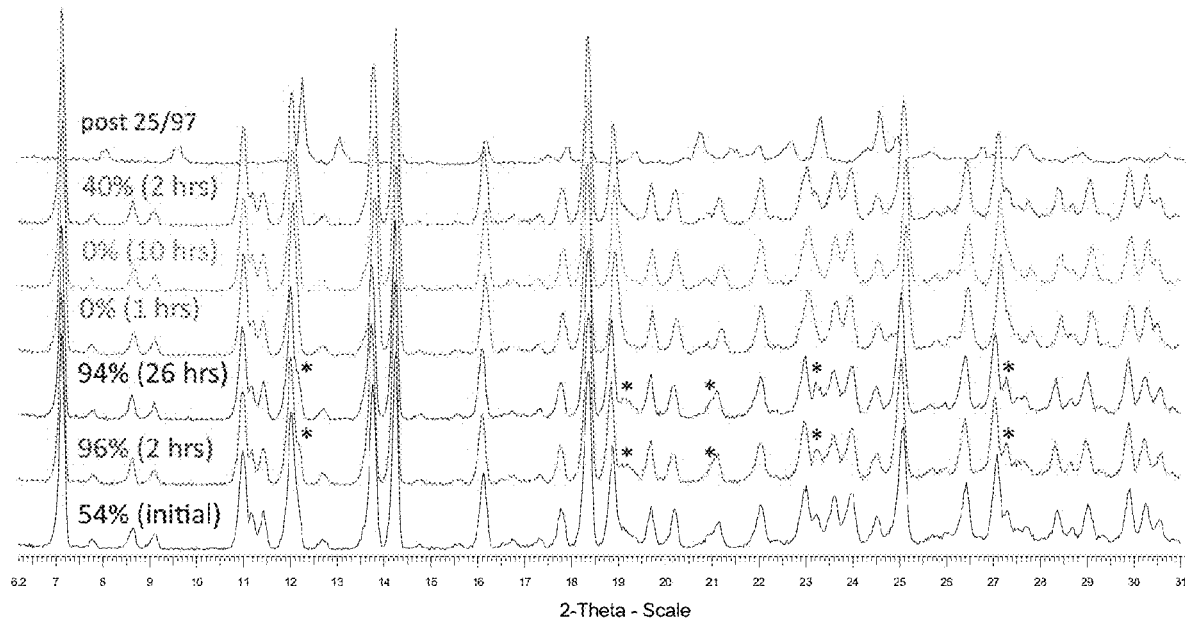
FIG. 4C: Overlay of VH-XRPD patterns of Sample 1 collected at varied RH.
Figure 4D:
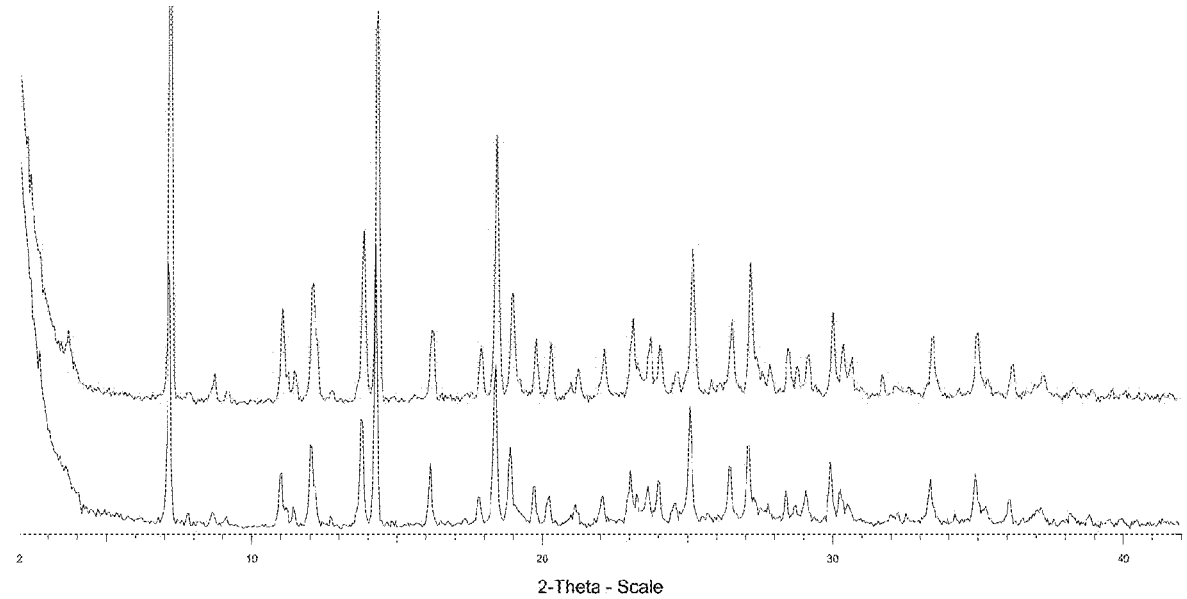
FIG. 4D: Overlay of XRPD patterns obtained for Sample 1 pre-(bottom) and post-(top) GVS (uptake 0-90% RH) analysis.
Figure 4E:
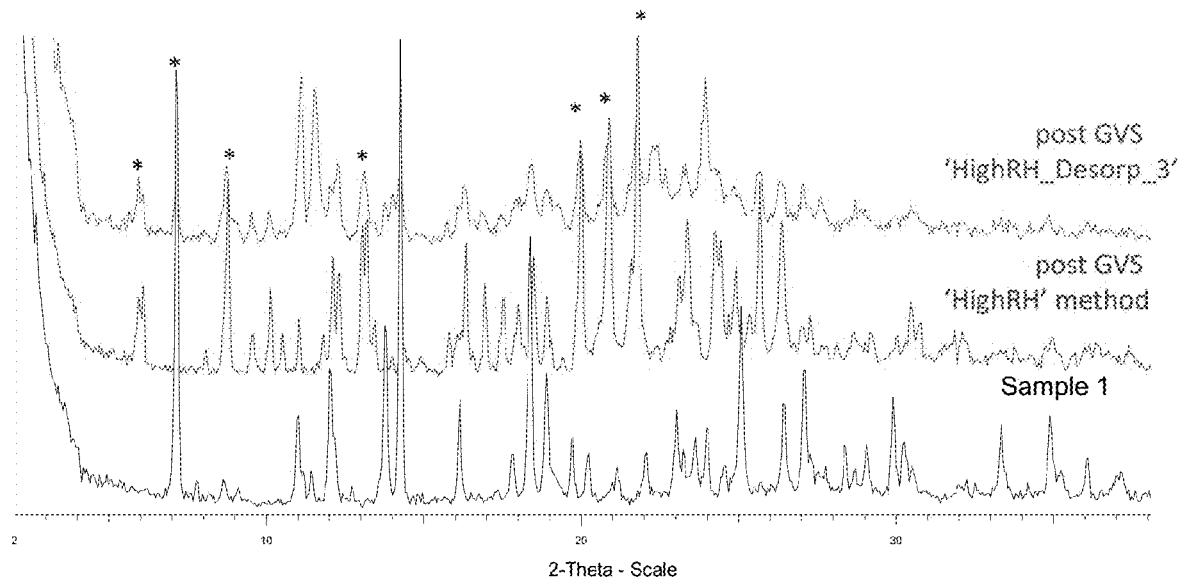
FIG. 4E: Overlay of XRPD patterns obtained for Sample 1 pre-(Sample 1) and post-GVS (HighRH_Desorp_3 and HighRH methods).
Figure 4F:
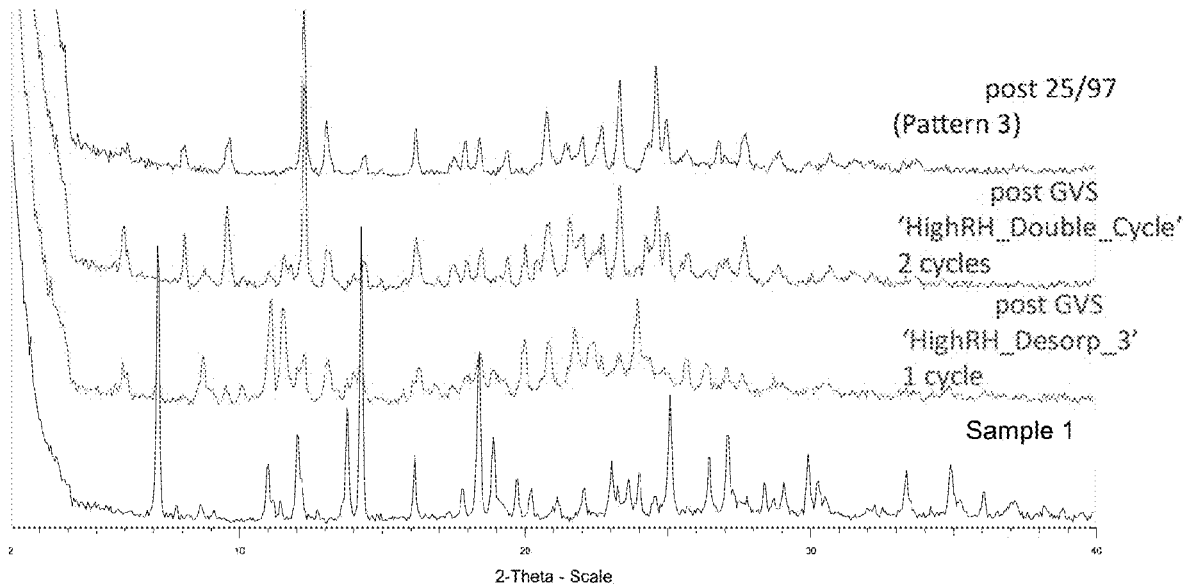
FIG. 4F: Overlay of XRPD patterns obtained for Sample 1 pre- and post-GVS (HighRH_Desorp_3's 1 cycle and HighRH Double Cycle's 2 cycles), and post storage at 25° C./97% RH.
Figure 4G:
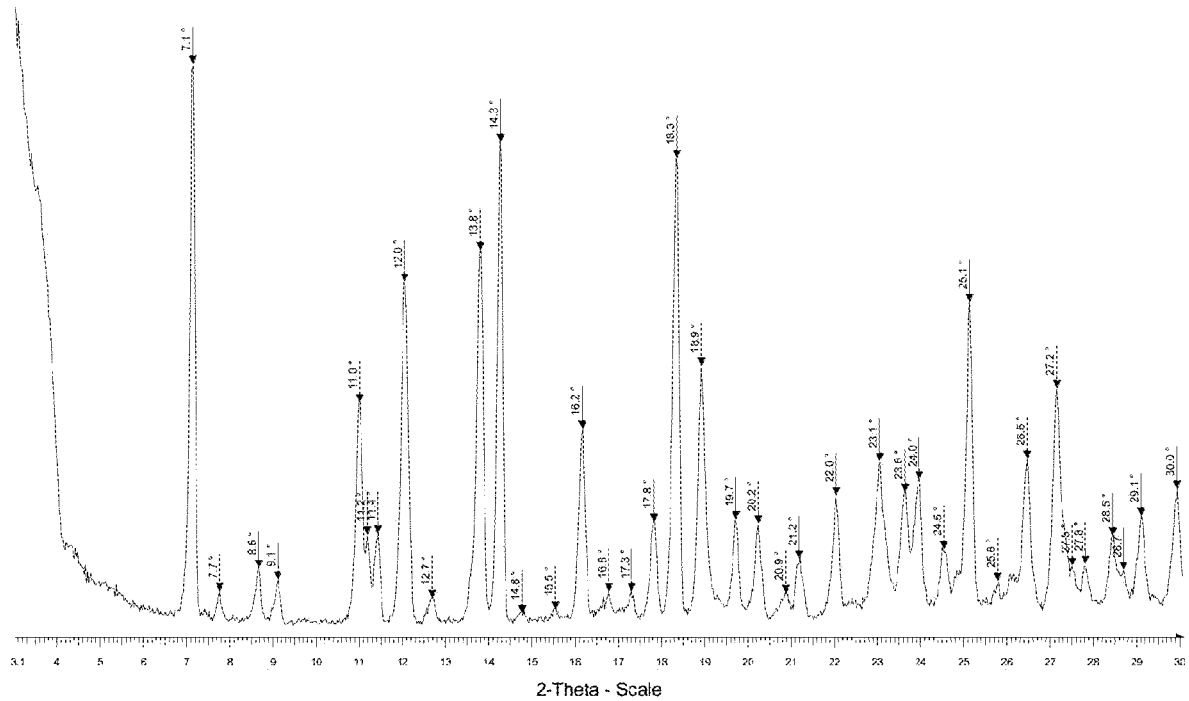
FIG. 4G: XRPD diffraction pattern of Sample 1 at 0% RH.

Certain embodiments disclosed herein provide a solid form (Form 1) having an X-ray powder diffraction pattern substantially as shown in FIG. 4G at about relative humidity 0%.

Certain embodiments disclosed herein provide a solid form of RAD1901-2HCl, having a differential scanning calorimetry (DSC) thermogram displaying a melting onset at 218.2° C. and an endothermic peak at 232.1° C., e.g., Form 1.

Figure 8:
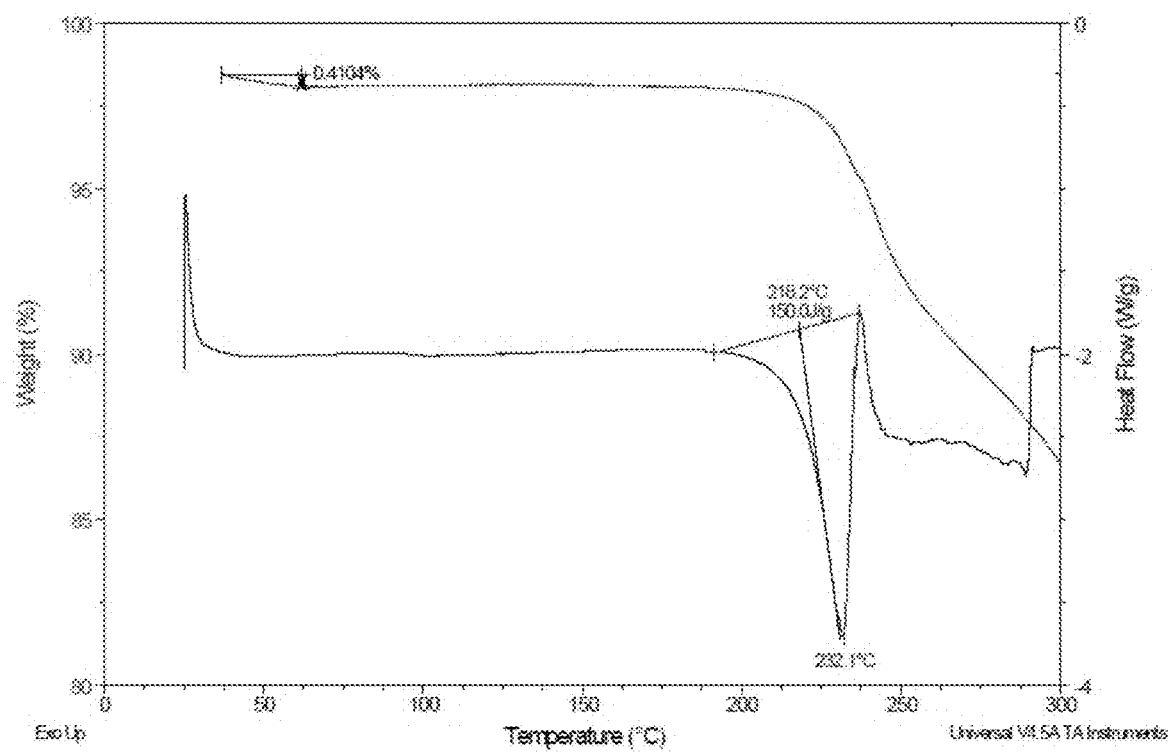
FIG. 8: Thermal analysis of Sample 1 by TGA (top) and DSC (bottom).

Certain embodiments disclosed herein provide a solid form of RAD1901-2HCl, having a differential scanning calorimetry (DSC) thermogram substantially as shown in the bottom graph of FIG. 8, e.g., Form 1.

Certain embodiments disclosed herein provide a solid form of RAD1901-2HCl, having a thermogravimetric analysis (TGA) substantially as shown in the top graph of FIG. 8, e.g., Form 1.

Certain embodiments disclosed herein provide a solid form of RAD1901 as disclosed herein (e.g., Form 1) wherein said solid form comprises at least 1% w/w of a total sample of RAD1901-2HCl.

Certain embodiments disclosed herein provide a composition comprising RAD1901 wherein at least 5% w/w of the total amount of RAD1901 is a solid form of RAD1901 as disclosed herein (e.g., Form 1).

Certain embodiments disclosed herein provide a composition comprising RAD1901 wherein at least 10% w/w of the total amount of RAD1901 is a solid form of RAD1901 as disclosed herein (e.g., Form 1).

Certain embodiments disclosed herein provide a composition comprising RAD1901 wherein at least 25% w/w of the total amount of RAD1901 is a solid form of RAD1901 as disclosed herein (e.g., Form 1).

Certain embodiments disclosed herein provide a composition comprising RAD1901 wherein at least 50% w/w of the total amount of RAD1901 is a solid form of RAD1901 as disclosed herein (e.g., Form 1).

Certain embodiments disclosed herein provide a composition comprising RAD1901 wherein at least 90% w/w of the total amount of RAD1901 is a solid form of RAD1901 as disclosed herein (e.g., Form 1).

Certain embodiments disclosed herein provide a composition comprising RAD1901 wherein at least 95% w/w of the total amount of RAD1901 is a solid form of RAD1901 as disclosed herein (e.g., Form 1).

Certain embodiments disclosed herein provide a composition comprising RAD1901 wherein at least 98% w/w of the total amount of RAD1901 is a solid form of RAD1901 as disclosed herein (e.g., Form 1).

Certain embodiments disclosed herein provide a composition comprising RAD1901 wherein at least 99% w/w of the total amount of RAD1901 is a solid form of RAD1901 as disclosed herein (e.g., Form 1).

Certain embodiments disclosed herein provide a pharmaceutical composition comprising Form 1 in any of its specified embodiments and one or more pharmaceutically acceptable excipients.

Certain embodiments disclosed herein provide a solid form of RAD1901-2HCl having an X-Ray powder diffraction pattern comprising a peak, in terms of 2-theta, at 6.3 degrees 2θ±0.2 degree 2θ at about relative humidity 0%, e.g., Form 2.

Certain embodiments disclosed herein provide a solid form of RAD1901-2HCl, having an X-ray powder diffraction pattern comprising a peak, in terms of 2-theta, at 6.3 degrees 2θ±0.2 degree 2θ, and/or 12.5 degrees 2θ±0.2 degree 2θ at about relative humidity 0%, e.g., Form 2.

Certain embodiments disclosed herein provide a solid form of RAD1901-2HCl, having an X-ray powder diffraction pattern comprising at least two peaks, in terms of 2-theta, selected from the group consisting of 6.3 degrees 2θ±0.2 degree 2θ, 12.5 degrees 2θ±0.2 degree 2θ, and 15.4 degrees 2θ±0.2 degree 2θ, at about relative humidity 0%, e.g., Form 2.

Certain embodiments disclosed herein provide a solid form of RAD1901-2HCl, having an X-ray powder diffraction pattern comprising at least two peaks, in terms of 2-theta, selected from the group consisting of 6.3 degrees 2θ±0.2 degree 2θ, 12.5 degrees 2θ±0.2 degree 2θ, and 15.4 degrees 2θ±0.2 degree 2θ, at about relative humidity 0%, e.g., Form 2.

Certain embodiments disclosed herein provide a solid form of RAD1901-2HCl, having an X-ray powder diffraction pattern comprising at least three peaks, in terms of 2-theta, selected from the group consisting of 6.3 degrees 2θ±0.2 degree 2θ, 12.5 degrees 2θ±0.2 degree 2θ, 15.4 degrees 2θ±0.2 degree 2θ, 18.3 degrees 2θ±0.2 degree 2θ, and 13.4 degrees 2θ±0.2 degree 2θ, at about relative humidity 0%, e.g., Form 2.

Figure 5A:
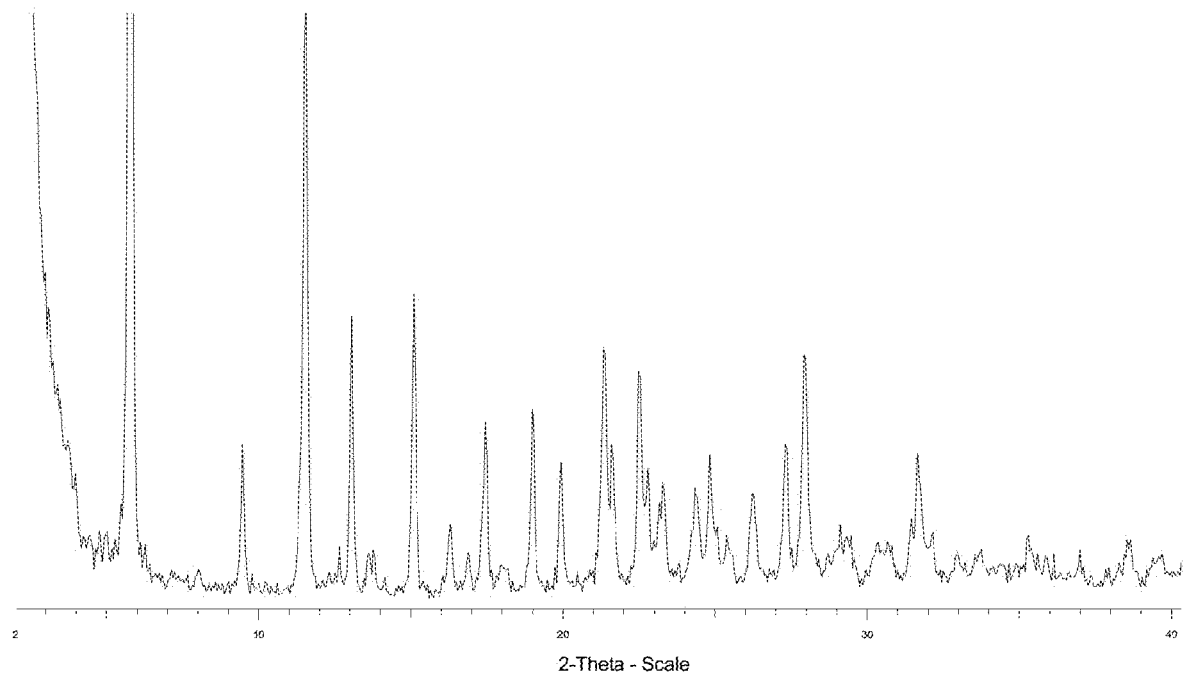
FIG. 5A: XRPD patterns obtained for Sample 2.
Figure 5B:
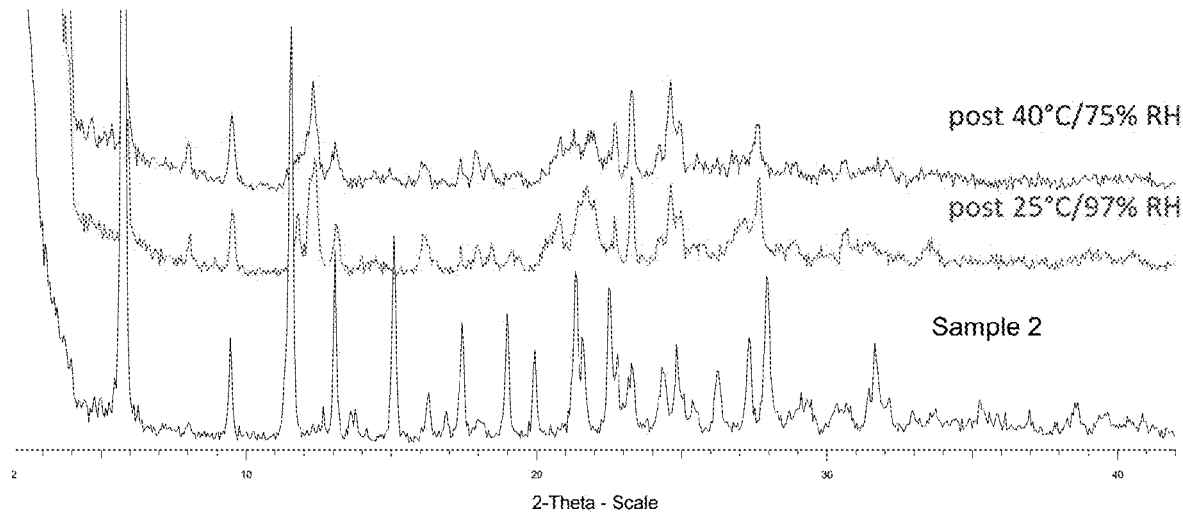
FIG. 5B: Overlay of XRPD patterns obtained for Sample 2 and post-storage at elevated condition analysis.
Figure 5C:
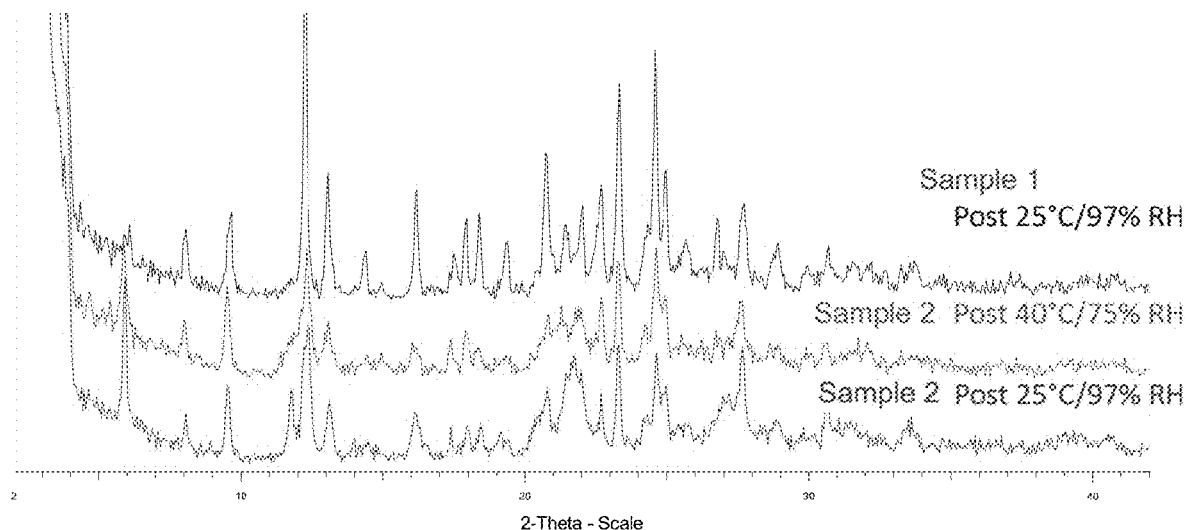
FIG. 5C: Overlay of XRPD patterns obtained for Sample 1 (top) and Sample 2 (bottom 2 plots) post-storage at elevated condition analysis.
Figure 5D:
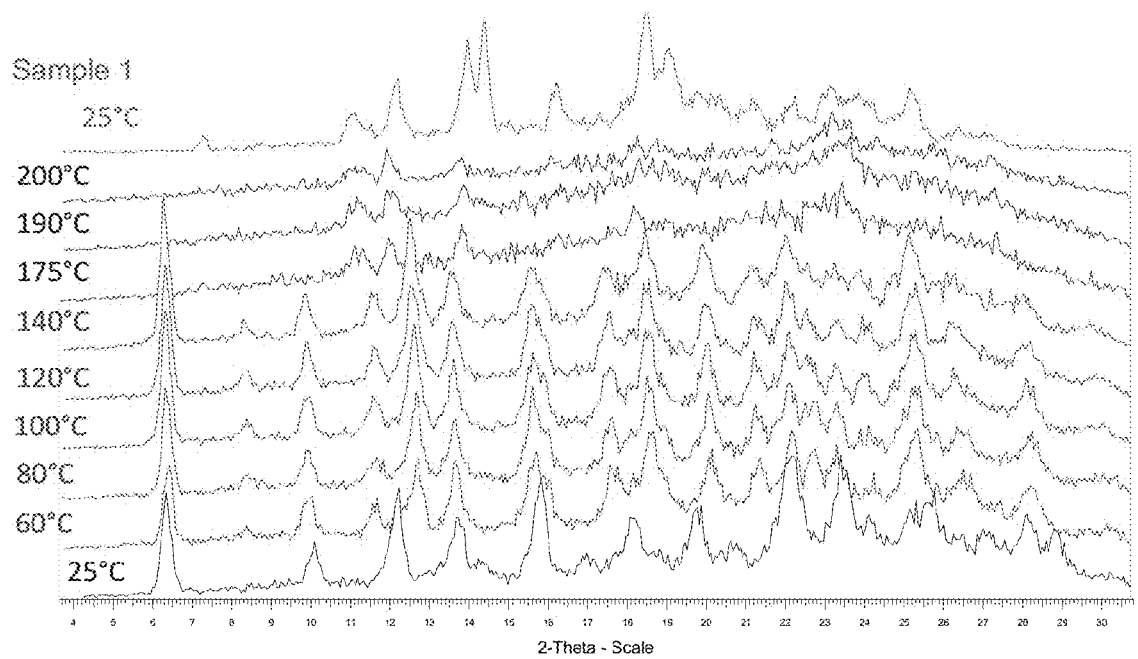
FIG. 5D: Overlay of VT-XRPD patterns of Sample 2 collected upon heating to 200° C. and Sample 1.
Figure 5E:
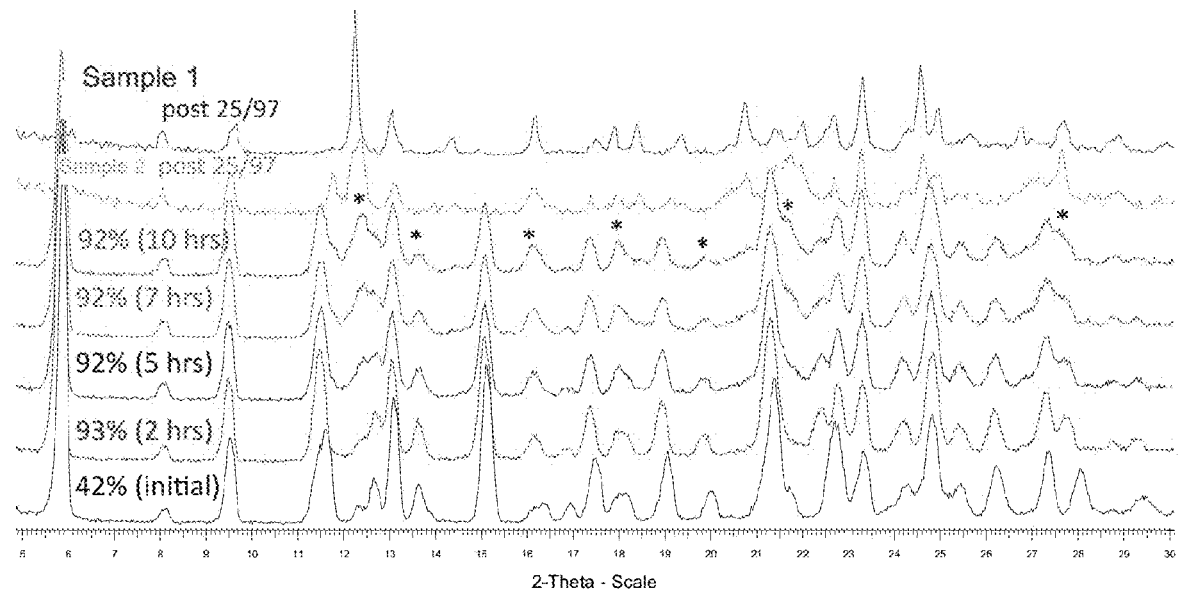
FIG. 5E: Overlay of VH-XRPD patterns of Sample 2 collected at high RH (>90%) and Sample 1 post storage at high RH.
Figure 5F:
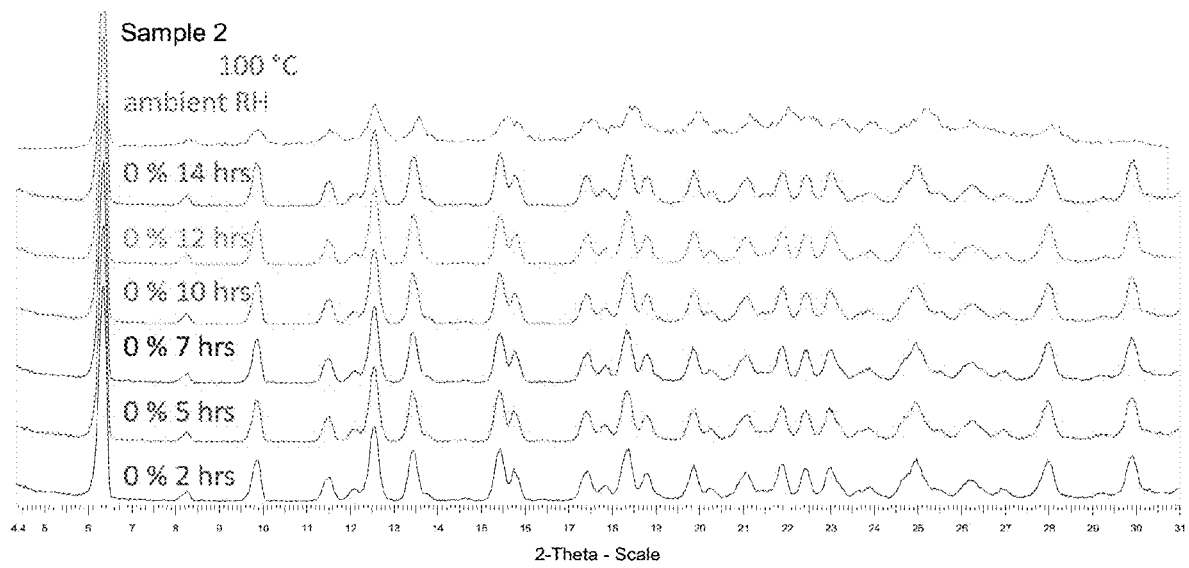
FIG. 5F: Overlay of VH-XRPD patterns of Sample 2 collected at dry condition (0% RH).
Figure 5G:
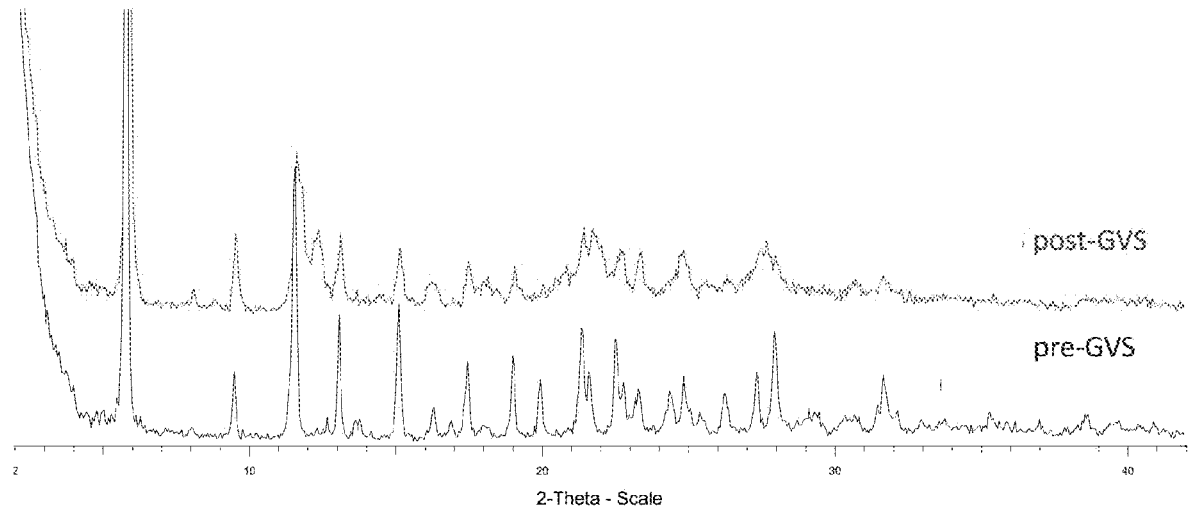
FIG. 5G: Overlay of XRPD patterns obtained for Sample 2 pre- and post-GVS (uptake 0-90% RH).
Figure 5H:
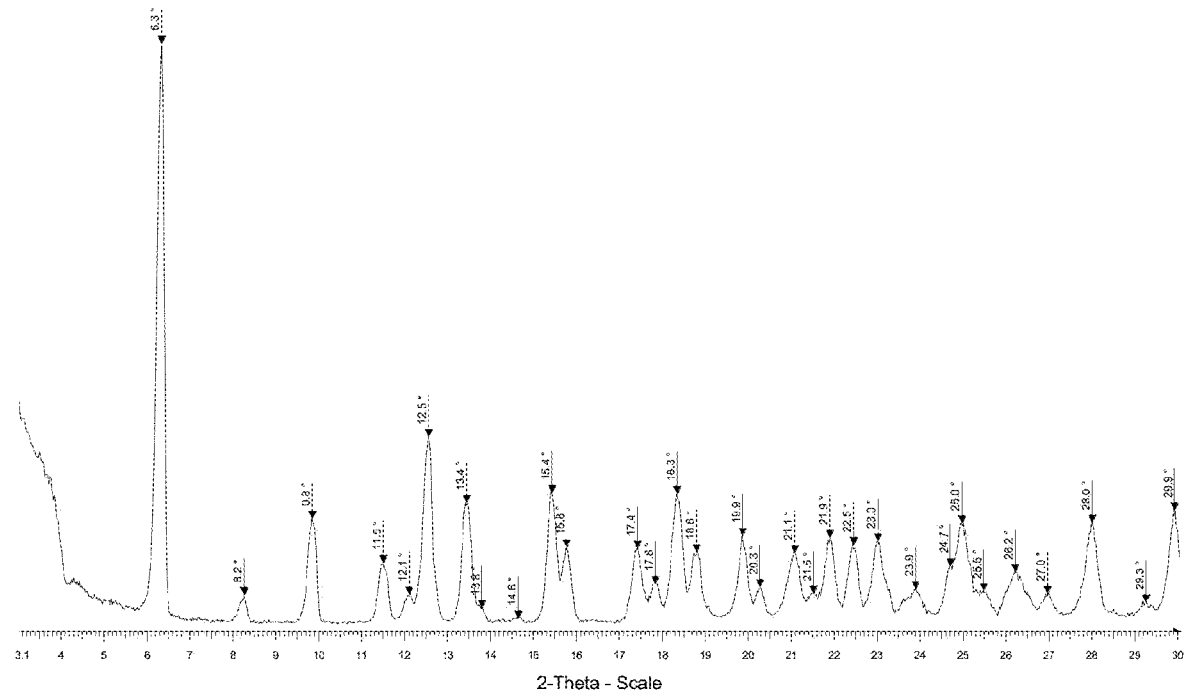
FIG. 5H: XRPD patterns obtained for Sample 2 at 0% RH (Form 2).

Certain embodiments disclosed herein provide a solid form of RAD1901-2HCl, having an X-ray powder diffraction pattern substantially as shown in FIG. 5H at about relative humidity 0%, e.g., Form 2.

Certain embodiments disclosed herein provide a pharmaceutical composition comprising a solid form of RAD1901-2HCl disclosed herein (e.g., Form 2), and one or more pharmaceutically acceptable excipients.

In some embodiments, a solid form RAD1901-2HCl is a crystalline mixture comprising less than 1% Form 2.

In certain embodiments, a solid form RAD1901-2HCl is a crystalline mixture comprising more than 0.1% of Form 2 but less than 2%.

In some embodiments, a solid form RAD1901-2HCl comprises at least 10% Form 2.

In some embodiments, a solid form RAD1901-2HCl comprises at least 25% Form 2.

In some embodiments, a solid form RAD1901-2HCl comprises at least 50% Form 2.

In some embodiments, a solid form RAD1901-2HCl comprises at least 75% Form 2.

In some embodiments, a solid form RAD1901-2HCl comprises at least 95% Form 2.

In some embodiments, a solid form RAD1901-2HCl comprises at least 97% Form 2.

In some embodiments, a solid form RAD1901-2HCl comprises at least 99% Form 2.

Certain embodiments disclosed herein provide a solid, hydrated form of RAD1901-2HCl, e.g., Form 3. In some embodiments the solid hydrated form of RAD1901-2HCl is a dihydrate.

Certain embodiments disclosed herein provide a solid, hydrated form of RAD1901-2HCl having an X-Ray powder diffraction comprising a peak, in terms of 2-theta, at 5.8 degrees 2θ±0.2 degree 2θ at about relative 92%, e.g., Form 3.

Certain embodiments disclosed herein provide a solid hydrated form of RAD901-2HCl having an X-ray powder diffraction pattern comprising a peak, in terms of 2-theta, at 5.8 degrees 2θ±0.2 degree 2θ, and/or 21.3 degrees 2θ±0.2 degree 2θ, at about relative humidity 92%, e.g., Form 3.

Certain embodiments disclosed herein provide a solid hydrated form of RAD1901-2HCl having an X-ray powder diffraction pattern comprising at least two peaks, in terms of 2-theta, selected from the group consisting of 5.8 degrees 2θ±0.2 degree 2θ, 21.3 degrees 2θ±0.2 degree 2θ, and 24.8 degrees 2θ±0.2 degree 2θ, at about relative humidity 92%, e.g., Form 3.

Certain embodiments disclosed herein provide a solid hydrated form of RAD1901-2HCl having an X-Ray powder diffraction pattern comprising at least three peaks, in terms of 2-theta, selected from the group consisting of 5.8 degrees 2θ±0.2 degree 2θ, 21.3 degrees 2θ±0.2 degree 2θ, 24.8 degrees 2θ±0.2 degree 2θ, 23.3 degrees 2θ±0.2 degree 2θ, and 9.5 degrees 2θ±0.2 degree 2θ, at about relative humidity 92%, e.g., Form 3.

Certain embodiments disclosed herein provide a solid hydrated form of RAD1901-2HCl having an X-Ray powder diffraction pattern comprising at least four peaks, in terms of 2-theta, selected from the group consisting of 5.8 degrees 2θ±0.2 degree 2θ, 21.3 degrees 2θ±0.2 degree 2θ, 24.8 degrees 2θ±0.2 degree 2θ, 23.3 degrees 2θ±0.2 degree 2θ, and 9.5 degrees 2θ±0.2 degree 2θ, at about relative humidity 92%, e.g., Form 3.

Certain embodiments disclosed herein provide a solid form of RAD1901-2HCl that is amorphous.

Certain embodiments disclosed herein provide one or more crystalline and/or amorphous form of RAD1901-2HCl dispersed into a matrix.

Certain embodiments are disclosed comprising a dosage form of RAD1901-2HCl comprising 50 gm, 100 mg, 200 mg, 300 mg, 400 mg, 500 mg, or 600 mg of RAD1901-2HCl in one or more crystalline and/or amorphous forms, wherein said one or more crystalline and/or amorphous forms are dispersed in a solid or liquid matrix.

II. Pharmaceutical Compositions and/or Formulas of Polymorphic Forms of RAD1901-2HCl Provided herein are pharmaceutical compositions comprising one or more polymorphous and/or amorphous forms of RAD1901-2HCl disclosed herein, and a physiologically acceptable carrier (also referred to as a pharmaceutically acceptable carrier or solution or diluent). Such carriers and solutions include pharmaceutically acceptable salts and solvates of compounds used in the methods of the instant invention, and mixtures comprising two or more of such compounds, pharmaceutically acceptable salts of the compounds and pharmaceutically acceptable solvates of the compounds. Such compositions are prepared in accordance with acceptable pharmaceutical procedures such as described in Remington's Pharmaceutical Sciences, 17th edition, ed. Alfonso R. Gennaro, Mack Publishing Company, Eaton, Pa. (1985), which is incorporated herein by reference.

The term "pharmaceutically acceptable carrier" refers to a carrier that does not cause an allergic reaction or other untoward effect in a subject to whom it is administered and are compatible with the other ingredients in the formulation. Pharmaceutically acceptable carriers include, for example, pharmaceutical diluents, excipients or carriers suitably selected with respect to the intended form of administration, and consistent with conventional pharmaceutical practices. For example, solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof. Pharmaceutically acceptable carriers may further comprise minor amounts of auxiliary substances such as wetting or emulsifying agents, preservatives or buffers, which enhance the shelf life or effectiveness of the therapeutic agent.

The term "patient" refers to a human subject.

The one or more polymorphous and/or amorphous forms of RAD1901-2HCl disclosed herein and pharmaceutical composition thereof may be formulated into unit dosage forms, meaning physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose. In certain embodiments, the compounds may be formulated for controlled release.

The one or more polymorphous and/or amorphous forms of RAD1901-2HCl disclosed herein and pharmaceutical composition thereof may be formulated according to any available conventional method. Examples of preferred dosage forms include a tablet, a powder, a subtle granule, a granule, a coated tablet, a capsule, a syrup, a troche, and the like. In the formulation, generally used additives such as a diluent, a binder, an disintegrant, a lubricant, a colorant, a flavoring agent, and if necessary, a stabilizer, an emulsifier, an absorption enhancer, a surfactant, a pH adjuster, an antiseptic, an antioxidant and the like can be used. In addition, the formulation is also carried out by combining compositions that are generally used as a raw material for pharmaceutical formulation, according to the conventional methods. Examples of these compositions include, for example, (1) an oil such as a soybean oil, a beef tallow and synthetic glyceride; (2) hydrocarbon such as liquid paraffin, squalane and solid paraffin; (3) ester oil such as octyldodecyl myristic acid and isopropyl myristic acid; (4) higher alcohol such as cetostearyl alcohol and behenyl alcohol; (5) a silicon resin; (6) a silicon oil; (7) a surfactant such as polyoxyethylene fatty acid ester, sorbitan fatty acid ester, glycerin fatty acid ester, polyoxyethylene sorbitan fatty acid ester, a solid polyoxyethylene castor oil and polyoxyethylene polyoxypropylene block co-polymer; (8) water soluble macromolecule such as hydroxyethyl cellulose, polyacrylic acid, carboxyvinyl polymer, polyethyleneglycol, polyvinylpyrrolidone and methylcellulose; (9) lower alcohol such as ethanol and isopropanol; (10) multivalent alcohol such as glycerin, propyleneglycol, dipropyleneglycol and sorbitol; (11) a sugar such as glucose and cane sugar; (12) an inorganic powder such as anhydrous silicic acid, aluminum magnesium silicicate and aluminum silicate; (13) purified water, and the like. Additives for use in the above formulations may include, for example, 1) lactose, corn starch, sucrose, glucose, mannitol, sorbitol, crystalline cellulose and silicon dioxide as the diluent; 2) polyvinyl alcohol, polyvinyl ether, methyl cellulose, ethyl cellulose, gum arabic, tragacanth, gelatin, shellac, hydroxypropyl cellulose, hydroxypropylmethyl cellulose, polyvinylpyrrolidone, polypropylene glycol-poly oxyethylene-block co-polymer, meglumine, calcium citrate, dextrin, pectin and the like as the binder; 3) starch, agar, gelatin powder, crystalline cellulose, calcium carbonate, sodium bicarbonate, calcium citrate, dextrin, pectic, carboxymethylcellulose/calcium and the like as the disintegrant; 4) magnesium stearate, talc, polyethyleneglycol, silica, condensed plant oil and the like as the lubricant; 5) any colorants whose addition is pharmaceutically acceptable is adequate as the colorant; 6) cocoa powder, menthol, aromatizer, peppermint oil, cinnamon powder as the flavoring agent; 7) antioxidants whose addition is pharmaceutically accepted such as ascorbic acid or alpha-tophenol.

Some embodiments disclosed herein provide a pharmaceutical dosage form comprising RAD1901-2HCl Form 1 in an amount of 50 gm, 100 mg, 200 mg, 300 mg, 400 mg, 500 mg, or 600 mg.

Certain embodiments disclosed herein provide a drug dosage form as a tablet comprising 50 gm, 100 mg, 200 mg, 300 mg, 400 mg, 500 mg, or 600 mg RAD1901-2HCl crystalline Form 1. In certain embodiments, at least 80%, at least 85%, at least 90%, at least 95%, at least 98%, or at least 99.5% of RAD1901 in the table is RAD1901-2HCl crystalline Form 1.

Certain embodiments disclosed herein provide a pharmaceutical composition comprising 50 gm, 100 mg, 200 mg, 300 mg, 400 mg, 500 mg, or 600 mg of a solid form of RAD1901-2HCl disclosed herein (e.g., comprising Form 2 and/or Form 3), and one or more pharmaceutically acceptable excipients.

In certain embodiments, a pharmaceutical dosage form comprises Form 2 as disclosed herein.

III. Use of the Polymorphic Forms of RAD1901-2HCl

Provided herein are methods of treating and/or preventing one or more conditions of a subject that can benefit from administration of RAD1901, the methods comprise administering to the subject with therapeutically effective amount of one or more polymorphic forms of RAD1901-2HCl disclosed herein, or a pharmaceutical composition thereof.

In certain embodiments, the one or more conditions treated/prevented by the methods disclosed herein are breast, uterus, and ovary tumors and/or cancers having overexpression of estrogen receptors, and metastatic cancer and/or tumor. In certain embodiments, the cancer and/or tumor treated in the methods disclosed herein are resistant ER-driven cancers or tumors, (e.g. having mutant ER binding domains (e.g. ERα comprising one or more mutations including, but not limited to, Y537$X_1$ wherein $X_1$ is S, N, or C, D538G, L536$X_2$ wherein $X_2$ is R or Q, P535H, V534E, S463P, V392I, E380Q and combinations thereof), overexpressors of the ERs or tumor and/or cancer proliferation becomes ligand independent, or tumors and/or cancers that progress after endocrinological treatment, such as with treatment of SERD (e.g., fulvestrant, TAS-108 (SR16234), ZK191703, RU58668, GDC-0810 (ARN-810), GW5638/DPC974, SRN-927, and AZD9496), aromatase inhibitor (e.g., anastrozole, exemestane, and letrozole), selective estrogen receptor modulators (e.g., tamoxifen, raloxifene, lasofoxifene, and/or toremifene), Her2 inhibitors (e.g., trastuzumab, lapatinib, ado-trastuzumab emtansine, and/or pertuzumab), chemo therapy (e.g., abraxane, adriamycin, carboplatin, cytoxan, daunorubicin, doxil, ellence, fluorouracil, gemzar, helaven, lxempra, methotrexate, mitomycin, micoxantrone, navelbine, taxol, taxotere, thiotepa, vincristine, and xeloda), angiogenesis inhibitor (e.g., bevacizumab), cdk4/6 inhibitors, m-TOR inhibitors and/or rituximab.

Provided herein are methods of modulating estrogen receptors of a subject, the methods comprise administering to the subject with therapeutically effective amount of one or more polymorphic forms of RAD1901-2HCl disclosed herein, or a pharmaceutical composition thereof; and the one or more polymorphic forms of RAD1901-2HCl disclosed herein demonstrate an estrogen-like action in the central nervous system, bone tissue and lipid metabolism, and/or estrogen antagonism in a reproductive organ and a mammary gland.

A therapeutically effective amount of the one of more polymorphic forms of RAD1901-2HCl for use in the methods disclosed herein is an amount that, when administered over a particular time interval, results in achievement of one or more therapeutic benchmarks (e.g., slowing or halting of tumor growth, cessation of symptoms, etc.). The skilled artisan can readily determine this amount, on either an individual subject basis (e.g., the amount of the one of more polymorphic forms of RAD1901-2HCl necessary to achieve a particular therapeutic benchmark in the subject being treated) or a population basis (e.g., the amount of the one of more polymorphic forms of RAD1901-2HCl necessary to achieve a particular therapeutic benchmark in the average subject from a given population). Ideally, the therapeutically effective amount does not exceed the maximum tolerated dosage at which 50% or more of treated subjects experience nausea or other toxicity reactions that prevent further drug administrations. A therapeutically effective amount may vary for a subject depending on a variety of factors, including variety and extent of the symptoms, sex, age, body weight, or general health of the subject, administration mode and salt or solvate type, variation in susceptibility to the drug, the specific type of the disease, and the like.

The one of more polymorphic forms of RAD1901-2HCl or the pharmaceutical composition thereof for use in the presently disclosed methods may be administered to a subject one time or multiple times. In those embodiments wherein the compounds are administered multiple times, they may be administered at a set interval, e.g., daily, every other day, weekly, or monthly. Alternatively, they can be administered at an irregular interval, for example on an as-needed basis based on symptoms, patient health, and the like.

Some embodiments disclosed herein provide a method of treating ER+ breast cancer comprising a daily administration of 400 mg of RAD1901-2HCl crystalline Form 1 in a dosage form wherein said dosage form is a tablet or capsule and said administration is oral.

Some embodiments disclosed herein provide a method of treating ER+ breast cancer in a subject, wherein: the ER+ breast cancer is resistant to one or more endocrinological therapies or the subject has progressed after prior treatment with one or more endocrinological therapies; the treatment comprises a daily administration of 400 mg of RAD1901-2HCl crystalline Form 1 in a dosage form; and the dosage form is a tablet or capsule and said administration is oral.

Some embodiments disclosed herein provide a method of treating ER+ breast cancer in a subject wherein: the ER+ breast cancer is resistant to one or more endocrinological therapies or the subject has progressed after prior treatment with one or more endocrinological therapies; the treatment comprises a first administration of 400 mg daily of RAD1901-2HCl crystalline Form 1 in a dosage form; the dosage form is a tablet or capsule; the administration is oral; the administration of RAD1901-2HCl crystalline Form 1 is in combination with a second administration of a cdk4/6 inhibitor and/or an m-TOR inhibitor; and the second administration is an administration method suitable for the cdk4/6 inhibitor and/or m-TOR inhibitor.

Some embodiments disclosed herein provide a method of treating ER+ breast cancer in a subject wherein: the ER+ breast cancer is resistant to one or more endocrinological therapies or the subject has progressed after prior treatment with one or more endocrinological therapies; the treatment comprises a first administration of 400 mg daily of RAD1901-2HCl crystalline Form 1 in a dosage form; the dosage form is a tablet or capsule; the administration is oral; and the first administrati is in combination with a second administration of palbociclib, ribociclib, abemaciclib and/or everolimus.

Some embodiments disclosed herein provide a method of treating ER+ breast cancer in a subject wherein: the ER+ breast cancer is resistant to one or more cdk4/6 inhibitors and/or m-TOR inhibitors; the treatment comprises a daily administration of 400 mg of RAD1901-2HCl crystalline Form 1 in a dosage form; the dosage form is a tablet or capsule; and the administration is oral.

Certain embodiments disclosed herein provide a method of treating breast cancer comprising an administration to a subject in need thereof a crystalline form of RAD1901-2HCl (e.g., Form 1 as disclosed herein). In some embodiments, the breast cancer is ER+.

Certain embodiments disclosed herein provide a method of treating ovarian cancer comprising an administration to a subject in need thereof RAD1901-2HCl (Form 1). In some embodiments, the ovarian cancer is ER+.

In some embodiments, provided herein is a method of treating ER+ breast cancer comprising an administration of a dosage form comprising one or more crystalline forms of RAD1901-2HCl as disclosed herein.

In some embodiments, the manufacture of a medicament useful for treating a subject in need with RAD1901-2HCl is provided herein, wherein the medicament comprises one or more crystalline and/or amorphous forms of RAD1901-2HCl as disclosed herein.

IV. Preparation of the Polymorphic Forms of RAD1901-2HCl

Provided herein are methods for preparing Forms 1, 2 and 3 of RAD1901-2HCl disclosed herein.

In certain embodiments, RAD1901-2HCl can be prepared by treating a RAD1901 solution in an organic solvent (e.g., EtOH, EtOAc, and mixtures thereof) with at least 2 eq. of HCl (e.g., in EtOH). In certain embodiments, a RAD1901-2HCl solution can be further concentrated, treated with an organic solvent (e.g., EtOAc), and filtered to provide RAD1901 as its bis-HCl salt, suitable for further processing according to the methods of form conversion provided in this disclosure.

In certain embodiments, Form 1 can be prepared by treating RAD1901-2HCl with an organic solvent substantially free of methanol (e.g., less than 5%, less than 4%, less than 3%, less than 2%, less than 1%, or less than 0.5% of the organic solvent is methanol) with relatively low water content (e.g., less than 5% v/v). In certain embodiments, Form 1 can be prepared by treating RAD1901-2HCl with an organic solvent (e.g., EtOH, etc.) with relatively low water content (e.g., less than 5% v/v) and then with another organic solvent in which RAD1901-2HCl has a lower solubility (e.g., esters such as EtOAc, etc.). As used herein, unless otherwise specified, an organic solvent may be a single organic solvent or a mixture of multiple organic solvents.

Certain embodiments disclosed herein provide methods of preparing Form 1 of RAD1901-2HCl comprising precipitating from a solution comprising RAD1901-2HCl and a solvent, or slurrying RAD1901-2HCl in a solvent, wherein the solvent comprises an organic solvent substantially free of methanol, and the content of water is at or below 5% v/v. In some embodiments, the organic solvent is selected from the group consisting of n-heptane, propyl acetate, ethyl acetate, isopropyl acetate, MIBK, MEK, 1-propanol, ethanol, TBME, 1,4-dioxane, toluene, 1,2-dimethoxyethane, tetrahydrofuran, dichloromethane, acetonitrile, nitromethane, and mixtures thereof.

In certain embodiments, Form 2, Form 3, or combinations thereof can be prepared by treating RAD1901-2HCl with an organic solvent containing water and/or methanol. In certain embodiments, Form 2, Form 3, or combinations thereof can be prepared by treating RAD1901-2HCl with an organic solvent containing water and/or methanol, and then with another organic solvent in which RAD1901-2HCl has a lower solubility (e.g., esters such as EtOAc, etc.). Form 3 can be preferably prepared via using solvents having a water content of 5% or higher. In certain embodiments, Form 2 can be prepared using MeOH with a water content of about 1% to about 2%.

In certain embodiments, methods for preparing Form 1 of RAD1901-2HCl comprises heating a composition comprising Form 2, Form 3, or combinations thereof at a temperature above 175° C. for a period of time sufficient for the conversion at a RH of about 90% or lower, about 85% or lower, about 80% or lower, about 75% or lower, about 70% or lower, about 65% or lower, about 60% or lower, about 55% or lower, about 50% or lower, about 45% or lower, or about 40% or lower.

In certain embodiments, methods of preparing Form 2 of RAD1901-2HCl comprises exposing a composition comprising Form 3 thereof to a RH of about 0% for a period of time sufficient for the conversion (e.g., 6 h at 0% RH).

In certain embodiments, methods of preparing Form 3 of RAD1901-2HCl comprises exposing a composition comprising Form 2, Form 3, or combinations thereof to a RH of about 40% or higher for a period of time sufficient for the conversion (e.g., about 2 weeks at RH 40%).

In certain embodiments, methods of preparing Form 3 of RAD1901-2HCl comprises exposing a composition comprising Form 1 to a RH of about 90% or higher for a period of time sufficient for the conversion (e.g., 1 week at 90% RH).

EXAMPLES

Instrument and Methodology

A. X-Ray Powder Diffraction (XRPD)

Two x-ray diffractometer instruments were used to collect X-ray diffraction patterns as described below.

A1. Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. A weekly performance check was carried out using a certified standard NIST 1976 Corundum (flat plate).

The beam divergence, i.e. the effective size of the X-ray beam on the sample, was approximately 4 mm. A θ-θ continuous scan mode was employed with a sample-detector distance of 20 cm which gave an effective 2θ range of 3.2°-29.7°. Typically, the sample was exposed to the X-ray beam for 120 seconds. The software used for data collection was GADDS for XP/2000 4.1.43 and the data were analyzed and presented using Diffrac Plus EVA v15.0.0.0.

A1-1) Ambient Conditions

Samples run under ambient conditions were prepared as flat plate specimens using powder as received without grinding. A sample was lightly pressed on a glass slide to obtain a flat surface.

A1-2) Non-Ambient Conditions

Samples run under non-ambient conditions were mounted on a silicon wafer with a heat-conducting compound. The sample was then heated from ambient to the appropriate temperature at 20° C./min and subsequently held isothermally for 1 minute before data collection was initiated. The sample was observed to melt during the experiment and recrystallized upon continued heated above this temperature.

A2. Bruker AXS D8 Advance

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument was performance checked using a certified Corundum standard (NIST 1976). The software used for data collection was Diffrac Plus XRD Commander v2.6.1 and the data were analyzed and presented using Diffrac Plus EVA v15.0.0.0.

A2-1) Ambient Conditions

Samples run under ambient conditions as flat plate specimens using powder as received. The sample was gently packed into a cavity, cut into polished, zero-background (510) silicon wafer. The sample was rotated in its own plane during analysis. The data were collected in an angular range of 2 to 42° 2θ, with a step size of 0.05° 2θ, and a collection time of 0.5 sec/step.

A2-2) Non-Ambient Conditions

Samples run under non-ambient conditions were prepared by gently packing into a cavity, cut into a silicon wafer to obtain a flat surface and mounted onto a humidity stage with an Ansyco controller and humidity sensor positioned directly next to the sample holder. The data were collected at 298.15 K with water temperature of 35.0° C., in an angular range of 3 to 31° 2θ, with a step size of 0.025° 2θ, a collection time of 2.0 sec/step, and a collection time at each % RH was 41 min 28 sec.

X-Ray Powder Diffraction (XRPD) patterns were collected at variable humidity values from 0 to 95% RH, based upon the humidity behavior of each compound observed during GVS experiments (described herein). For each Variable Humidity X-Ray Powder Diffraction (VH-XRPD) experiment performed, the % RH values selected are provided alongside the relevant experimental result. Full tables of detailing the % RH value at each collection point and the associated delay time at each value are provided in Tables 10-12.

Unless stated otherwise, listed 2θ values in this disclosure are +/−0.2 degrees 2θ.

B. Nuclear Magnetic Resonance (NMR): $^1$H NMR and $^{13}$C NMR

NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone. Samples were prepared in DMSO-d6. Off-line analysis was carried out using ACD Spectrus Processor 2014.

C. Differential Scanning Calorimetry (DSC)

DSC data were collected on a TA Instruments Q2000 equipped with a 50 position autosampler. The calibration for thermal capacity was carried out using sapphire and the calibration for energy and temperature was carried out using certified indium. Each sample (e.g., 1 mg, 2 mg), in a pin-holed aluminum pan, was heated at 10° C./min from 25° C. to 300° C. A purge of dry nitrogen at 50 ml/min was maintained over the sample. Modulated temperature DSC was carried out using an underlying heating rate of 1 or 2° C./min and temperature modulation parameters of ±0.318 or 0.636° C. (amplitude) respectively, every 60 seconds (period).

The instrument control software was Advantage for Q Series v2.8.0.394 and Thermal Advantage v5.5.3 and the data were analyzed using Universal Analysis v4.5A.

Unless stated otherwise, listed DSC temperatures are +/−3° C.

D. Thermo-Gravimetric Analysis (TGA)

TGA data were collected on a TA Instruments Q500 TGA, equipped with a 16 position autosampler. The instrument was temperature calibrated using certified Alumel and Nickel. Each sample (e.g., 5 mg) was loaded onto a pre-tared aluminum DSC pan and heated at 10° C./min from ambient temperature to 300° C. A nitrogen purge at 60 ml/min was maintained over the sample.

The instrument control software was Advantage for Q Series v2.5.0.256 and Thermal Advantage v5.5.3 and the data were analyzed using Universal Analysis v4.5A.

E. Polarized Light Microscopy (PLM)

Samples were studied on a Nikon SMZ1500 polarized light microscope with a digital video camera connected to a DS Camera control unit DS-L2 for image capture. A small amount of each sample was placed on a glass slide, mounted in immersion oil, the individual particles being separated as well as possible. The sample was viewed with appropriate magnification and partially polarized light, coupled to a λ false-color filter.

F. Scanning Electron Microscopy (SEM)

Data were collected on a Phenom Pro Scanning Electron Microscope. A small quantity of sample was mounted onto an aluminum stub using conducting double-sided adhesive tape. A thin layer of gold was applied using a sputter coater (20 mA, 120 s).

G. Water Determination by Karl Fischer Titration (KF)

The water content of each sample was measured on a Metrohm 874 Oven Sample Processor at 200° C. with 851 Titrano Coulometer using Hydranal Coulomat AG oven reagent and nitrogen purge. Weighed solid samples were introduced into a sealed sample vial. Approx 10 mg of sample was used per titration and duplicate determinations were made. Data collection and analysis using Tiamo v2.2.

H. Chemical Purity Determination by HPLC

Purity analysis was performed on an Agilent HP1100 series system equipped with a diode array detector (255 nM with 90 nM bandwidth) and using ChemStation software vB.04.03. Samples were prepared as 0.4-0.6 mg/mL in acetonitrile: water 1:1 solution. HPLC analysis was performed on a Supelco Ascentic Express C18 reversed-phase column (100×4.6 mm, 2.7 μm) with gradient elution shown in Table 1 at a flow rate of 2 mL/min. The column temperature was 25° C.; and each sample injection was 2 or 3 μL.

TABLE 1

HPLC Gradient Elution

| Time (min) | % Phase A (0.1% TFA in water) | % Phase B (0.085% TFA in acetonitrile) |
|---|---|---|
| 0 | 95 | 5 |
| 6 | 5 | 95 |
| 6.2 | 95 | 5 |
| 8 | 95 | 5 |

I. Gravimetric Vapour Sorption (GVS)

Sorption isotherms were obtained using a SMS DVS Intrinsic moisture sorption analyzer, controlled by DVS Intrinsic Control software v1.0.1.2 (or v 1.0.1.3). The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg).

A sample (e.g., 20 mg) was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). Standard isotherms were performed at 25° C. at 10% RH intervals over a 0-90% RH range. Data analysis was carried out using Microsoft Excel using DVS Analysis Suite v6.2 (or 6.1 or 6.0).

In a cycle of 2 scans, the first scan was performed with adsorption of 40-90% RH, followed by a second scan with desorption of 90-0% RH and adsorption of 0-40% RH, with intervals of 10% RH, at 25° C. with stability dm/dt of 0.002% ° C./min. The sorption time was 6 hr time out.

The sample was recovered after completion of the isotherm and re-analyzed by XRPD. Custom moisture sorption methods were also performed at 25° C. at fixed % RH intervals over a 0-95% RH range, with the purpose to fully understand the sorption/desorption behavior of the compound under elevated conditions. The custom method performed for each GVS experiment was provided in Tables 2-4 below.

TABLE 2

Custom GVS method at high % RH (HighRH, Steps 1 and 2) and Single Cycle GVS method at high % RH (HighRH_Desorp_3, Steps 1, 2, 3, and 4)

| Parameter | Steps | | | |
| | 1 | 2 | 3 | 4 |
|---|---|---|---|---|
| Adsorption/Desorption Intervals (% RH) | 40-80 10 | 90, 95 — | 90-0 10 | 0-40 10 |
| Sorption time | 6 hr time out | Held at each RH for 800 mins | 6 hr time out | 6 hr time out |
| Stability dm/dt (% ° C./min) | 0.002 | — | 0.002 | 0.002 |

TABLE 3

Custom Double Cycle GVS method (HighRH_DoubleCycle_2)

| Parameter | Steps | | | | | |
| | 1 | 2 | 3 | 4 | 5 | 6 |
|---|---|---|---|---|---|---|
| Adsorption/Desorption Intervals (% RH) | 40-80 10 | 90 — | 95 — | 90-0 10 | 0 — | 0-40 10 |
| Sorption time | 6 hr time out | Held at each RH for 800 mins | Held for 1,600 mins | 6 hr time out | Held for 800 mins | 6 hr time out |
| Stability dm/dt (% ° C./min) | 0.002 | — | — | 0.002 | — | 0.002 |

TABLE 4

Custom Double Cycle GVS method (P2803-J06994_3)

| Parameter | Steps | | | | |
| | 1 | 2 | 3 | 4 | 5 |
|---|---|---|---|---|---|
| Adsorption/Desorption Intervals (% RH) | 40-80 10 | 90-95 — | 90-0 10 | 0 — | 0-40 10 |
| Sorption time | 6 hr time out | Held at each RH for 800 mins | 6 hr time out | Held for 800 mins | 6 hr time out |
| Stability dm/dt (% ° C./min) | 0.002 | — | 0.002 | — | 0.002 |

J. Ion Chromatography (IC)

Data were collected on a Metrohm 930 Compact IC Flex with 858 Professional autosampler and 800 Dosino dosage unit monitor, using IC MagicNet software v3.1. Accurately weighed samples were prepared as stock solutions in an appropriate dissolving solution and diluted appropriately prior to testing. Quantification was achieved by comparison with standard solutions of known concentration of the ion being analyzed. IC method for anion chromatography was performed on a Metrosep A Supp 5-150 IC column (4.0×150 mm) at ambient temperature and a flow rate of 0.7 mL/min with injections of various μL. The eluent used was 3.2 mM sodium carbonate, 1.0 mM sodium hydrogen carbonate in a 5% acetone aqueous solution. A conductivity detector was used for detection.

Example 1. Preparation and Characterization of Crystalline Forms 1, 2, and 3 of RAD1901-2HCl RAD1901 in EtOH was added to EtOAc and the resultant mixture was heated until dissolution. The solution was cooled to approximately 20° C. and treated with 2.1 eq HCl in EtOH. The solution was concentrated and the resultant mixture was treated with EtOAc at approximately 20° C. and filtered to yield RAD1901 as its bis-HCl salt, suitable for further processing according to the methods of form conversion provided in this disclosure.

Two samples of RAD1901-2HCl, Samples 1 and 2, were prepared. Sample 1 was prepared by dissolving RAD1901-2HCl in a mixture of water and ethanol (1.5:19). The water content was reduced to <0.5% by azeotropic distillation and the concentrated solution was diluted with ethyl acetate. The mixture was stirred at ambient temperature for at least 2 hours and then the solid was collected by filtration. Sample 2 was prepared by dissolving RAD1901-2HCl in methanol. Ethyl acetate was added to the solution and the resulting mixture was stirred for at least 1 hour at ambient temperature. The solid was collected by filtration.

Samples 1 and 2 were characterized by XRPD at various conditions. XRPD patterns were collected for the samples at ambient condition as the samples were provided; at variable temperature (VT-XRPD); at variable humidity (VH-XRPD); after the samples were exposed to 40° C./75% RH for 1 week and 25° C./97% RH for 1 week, respectively; and after a GVS measurement wherein the samples were exposed to 0-90% RH. Samples 1 and 2 were also characterized by $^1$H NMR, TGA, DSC, KF, IC, GVS (exposed to 0-90% RH), PLM, SEM, and HPLC (Table 5).

Characterizations of Sample 1 (majorly Form 1) and Sample 2 (mixture of Form 2 and Form 3) show that Form 1 was stable, had lower hygroscopicity and better thermal properties than Form 2. Additionally, Form 1 could be converted to the hydrate Form 3 at high RH (>90%) (e.g., for 7 days); Form 3 of RAD1901-2HCl could also be prepared by exposing Form 2 to >40% RH for 7 days; Sample 2 (mixture of Form 2 and Form 3) could be converted to Form 1 when heated at above 175° C. at <90% RH; and Form 2 may also be prepared by exposing Form 3 to <40% RH for 8 hr. Thus, limiting the level of water/humidity in the preparation of RAD1901-2HCl may be beneficial to prepare Form 1 of RAD1901-2HCl. In certain embodiments, the percentage of water present in the preparation method was below 5% v/v and water content was determined by e.g. Karl Fischer titration (KF).

TABLE 5

Characterization of RAD1901-2HCl Samples 1 and 2

| Characterization Method | Sample/Method | Sample 1 | Sample 2 |
| --- | --- | --- | --- |
| HPLC (Purity %, AUC) | N/A | 99.2% AUC (FIG. 2A) | 99.2% AUC (FIG. 3A) |
| $^1$H-NMR | N/A | Consistent with structure (FIG. 2B) | Consistent with structure (FIG. 3B) |
| XRPD | Ambient condition | Crystalline, Form 1 (FIG. 4B) | Crystalline, mixture of Form 2 and 3 (FIG. 5A) |
| XRPD | Storage at 40° C./75% RH for 1 week | Form 1 (FIG. 4B) | Form 3 (FIG. 5B) |
| XRPD | Storage at 25° C./97% RH for 1 week | Form 3 (FIGS. 4B and 5C) | Form 3 (FIGS. 5B and 5C) |
| VT-XRPD | N/A | N/A | Anhydrous Form 2 obtained on heating to 100° C. Sample melted ~160° C. and recrystallized as Form 1 above 175° C. (FIG. 5D). |
| VH-XRPD | N/A | Form 1 converted to Form 3 over 24 hr at ~95% RH (FIG. 4C) | Conversion to Form 3 at >90% RH (FIG. 5E). Form 2 at 0% RH (FIG. 5F) |
| XRPD post GVS | GVS (uptake 0-90% RH) | Form 1 (FIG. 4D) | Mixture of form 2 and 3 (FIG. 5G) |
| XRPD post GVS | GVS (HighRH method, HighRH_Desorp_3 method, Table 2) | FIG. 4E | N/A |
| XRPD post GVS | GVS (HighRH_Desorp_3's 1 cycle and HighRH_Double_Cycle's 2 cycles, Tables 3 and 4) | FIG. 4F | N/A |

TABLE 5-continued

Characterization of RAD1901-2HCl Samples 1 and 2

Figure 4H:
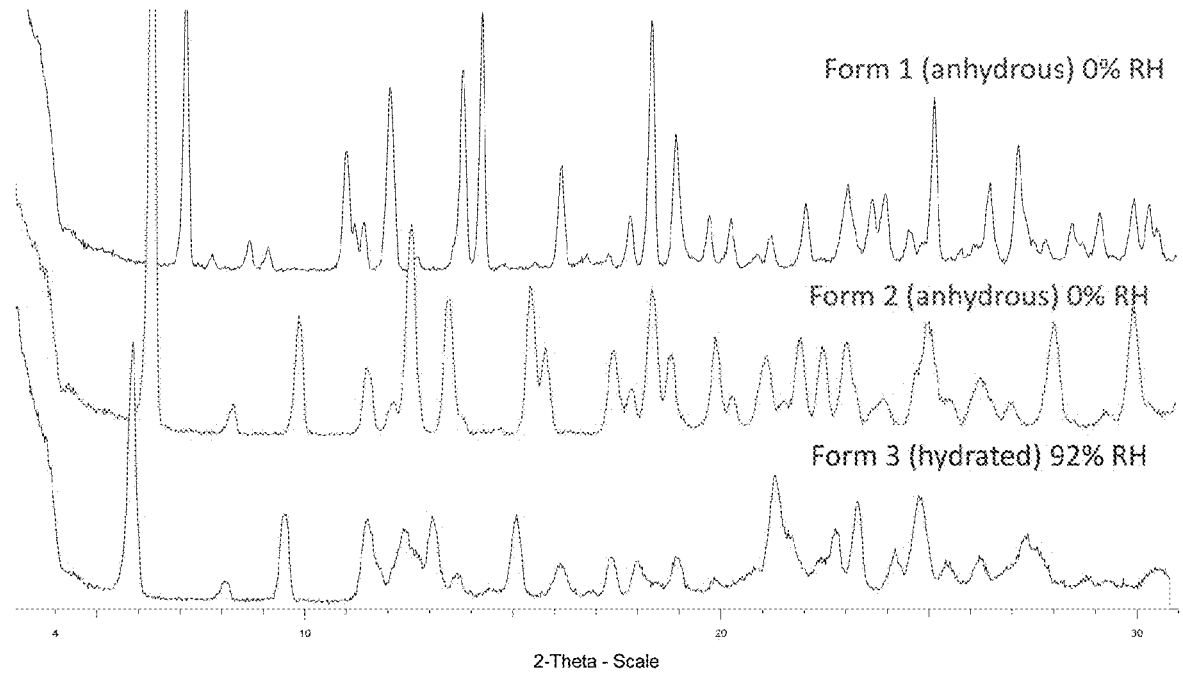
FIG. 4H: Overlay of XRPD diffraction pattern of Forms 1-3.
Figure 5I:
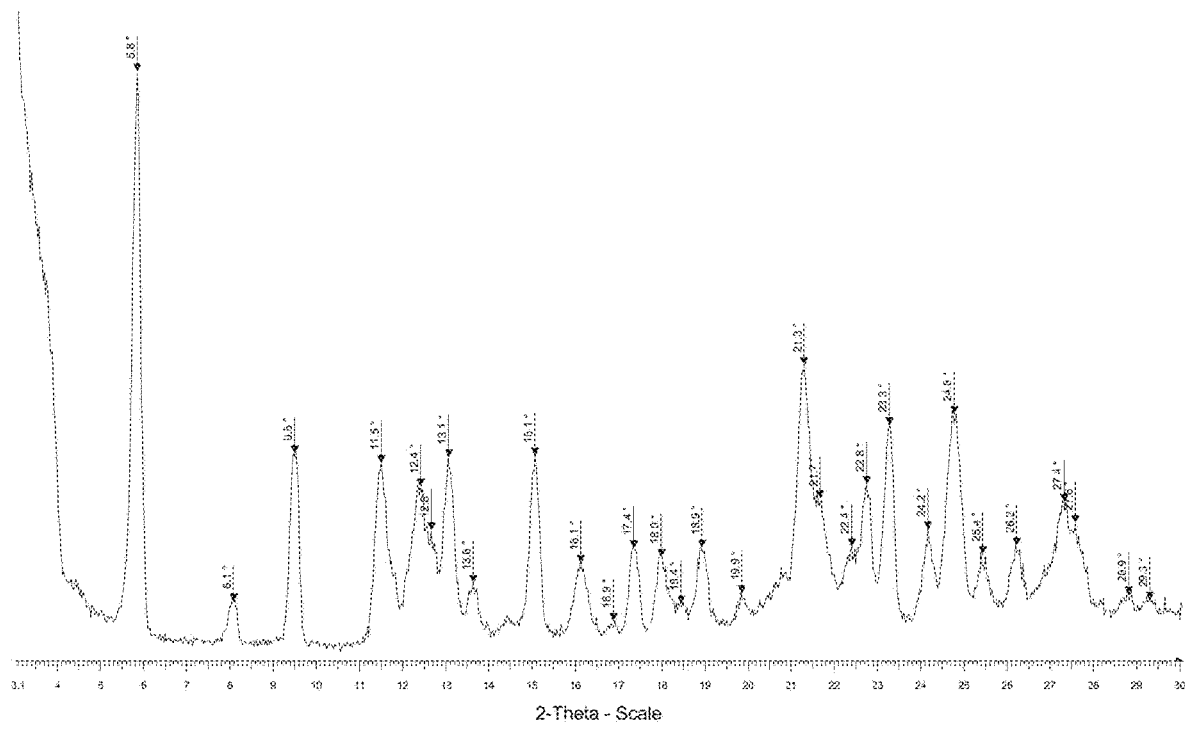
FIG. 5I: XRPD patterns obtained for Sample 2 at 92% RH (Form 3).
Figure 9:
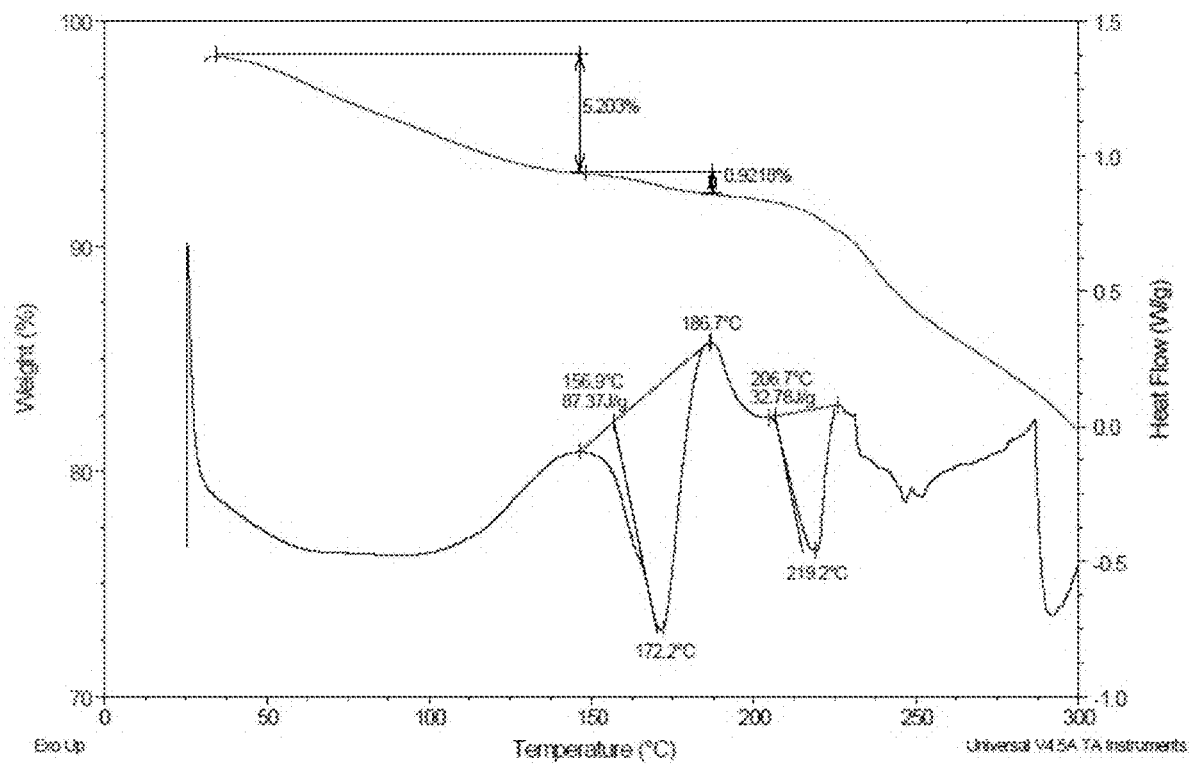
FIG. 9: Thermal analysis of Sample 2 by TGA (top) and DSC (bottom).
Figure 10A:
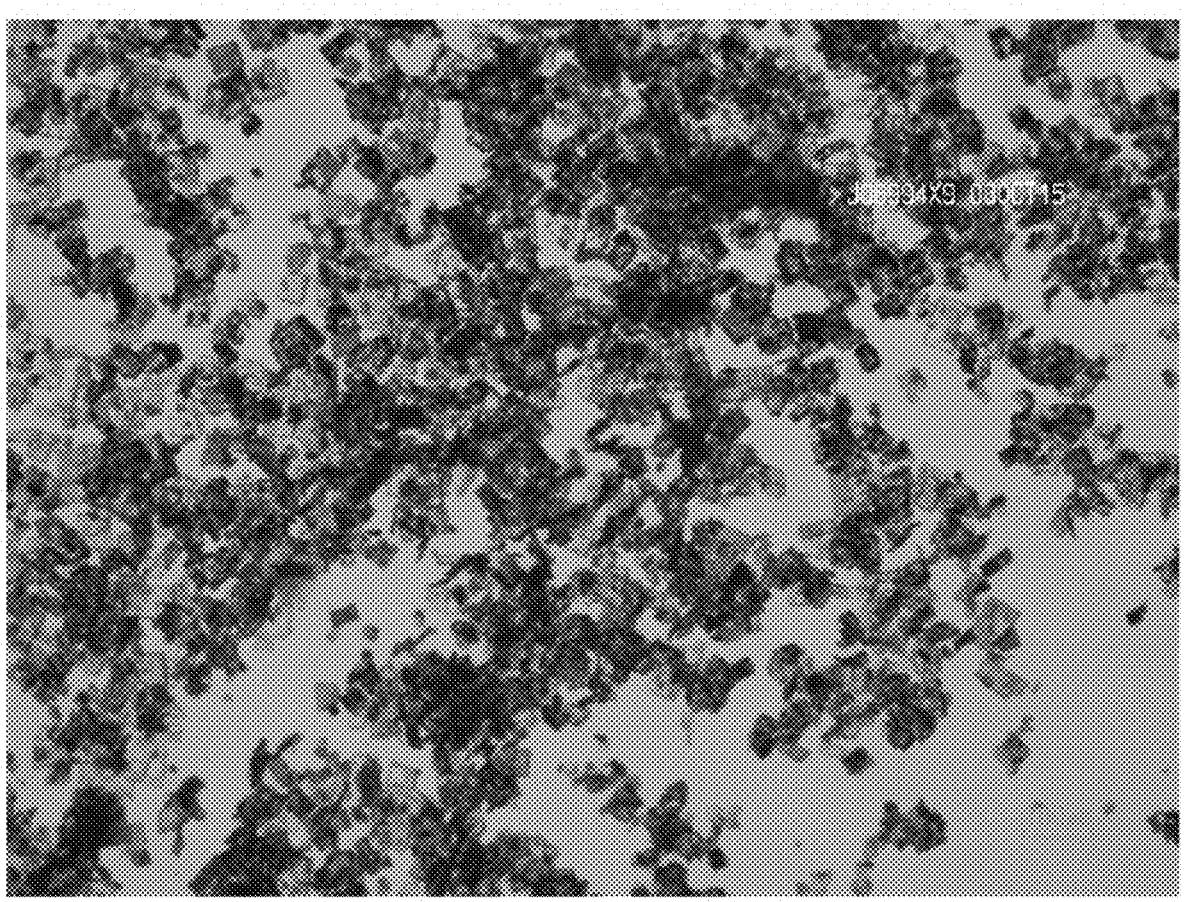
FIG. 10A: PLM images of Sample 1.
Figure 12A:
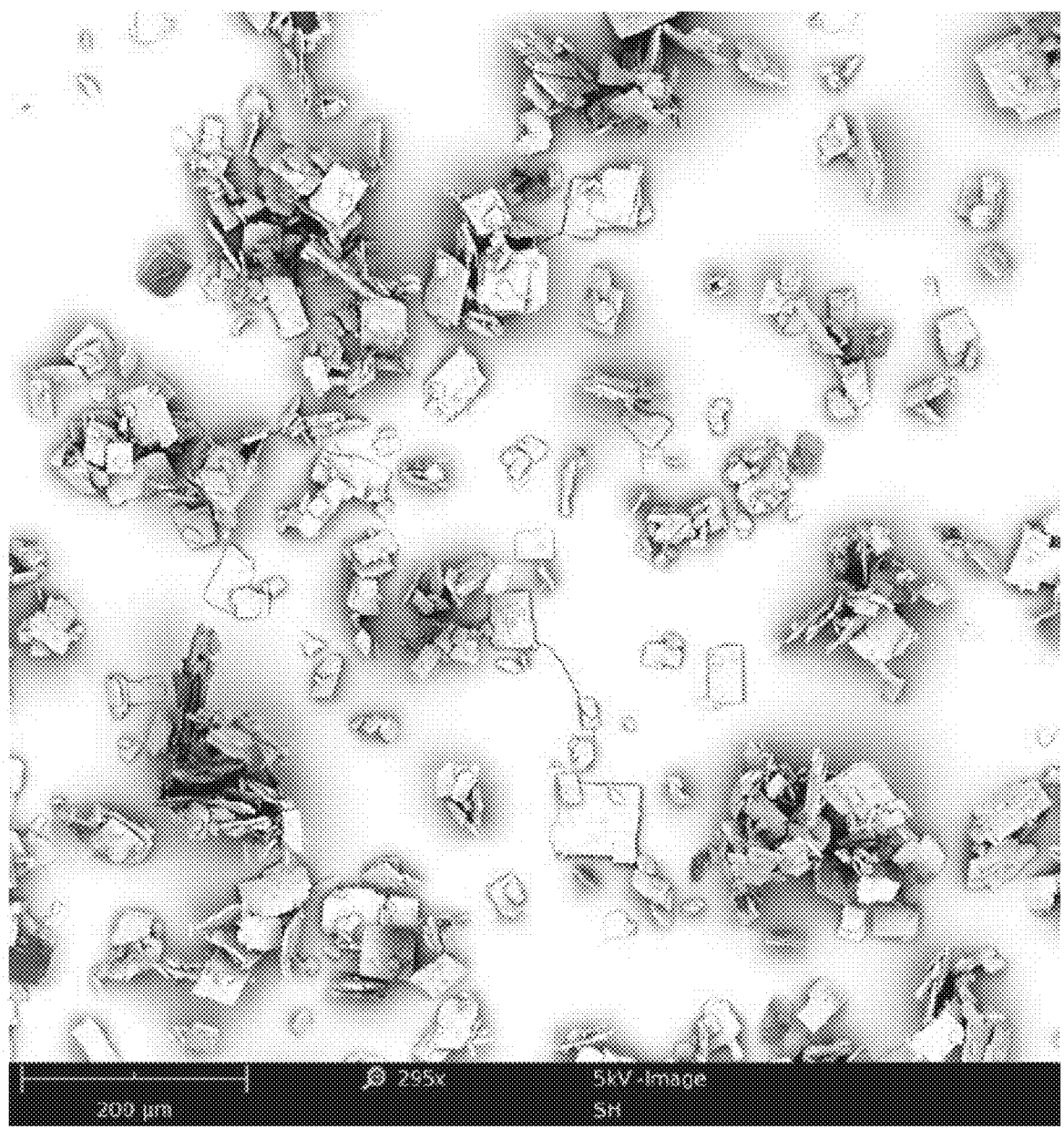
FIG. 12A: SEM images of Sample 1 (295×).
Figure 12B:
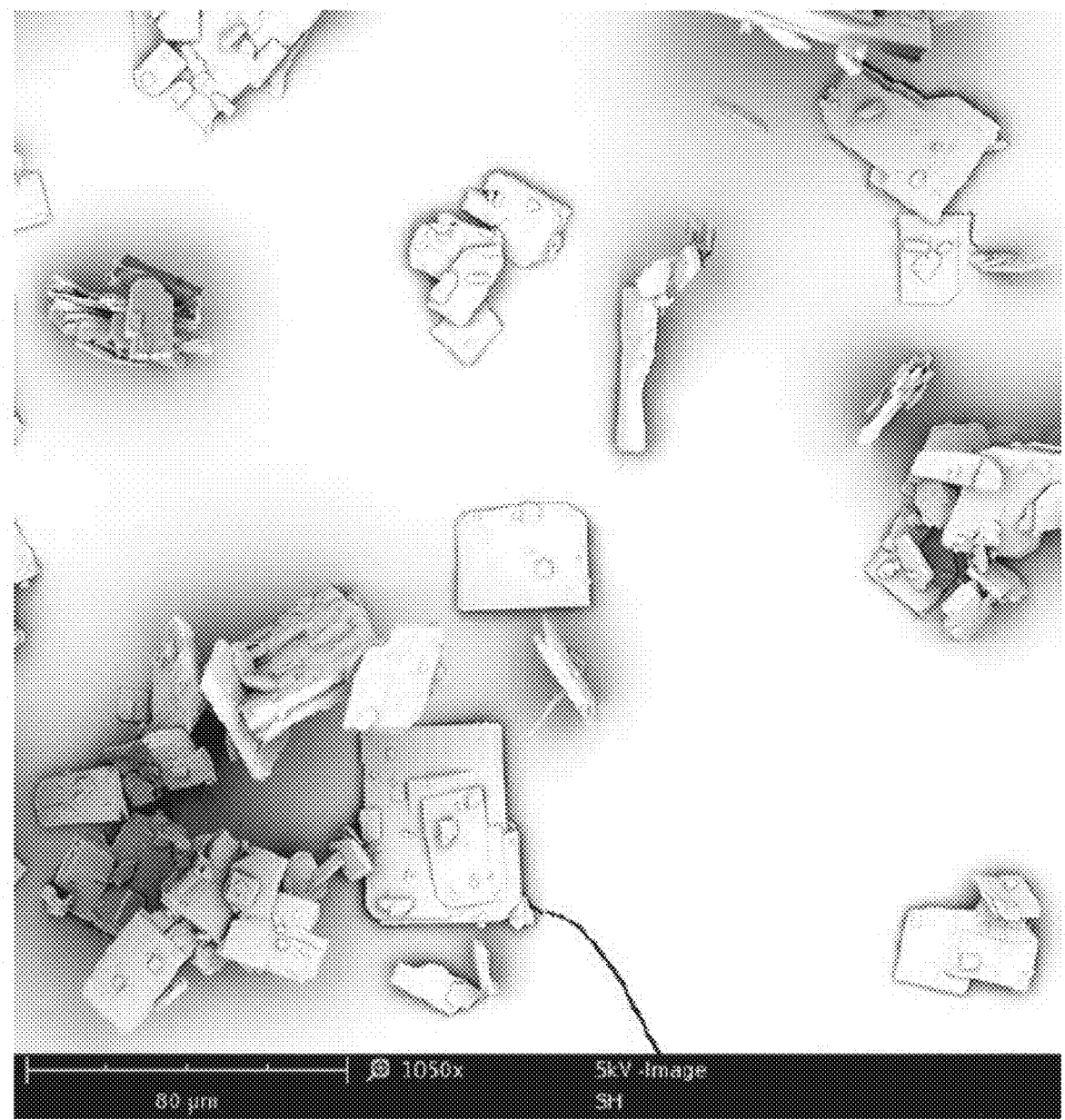
FIG. 12B: SEM images of Sample 1 (1050×).
Figure 12C:
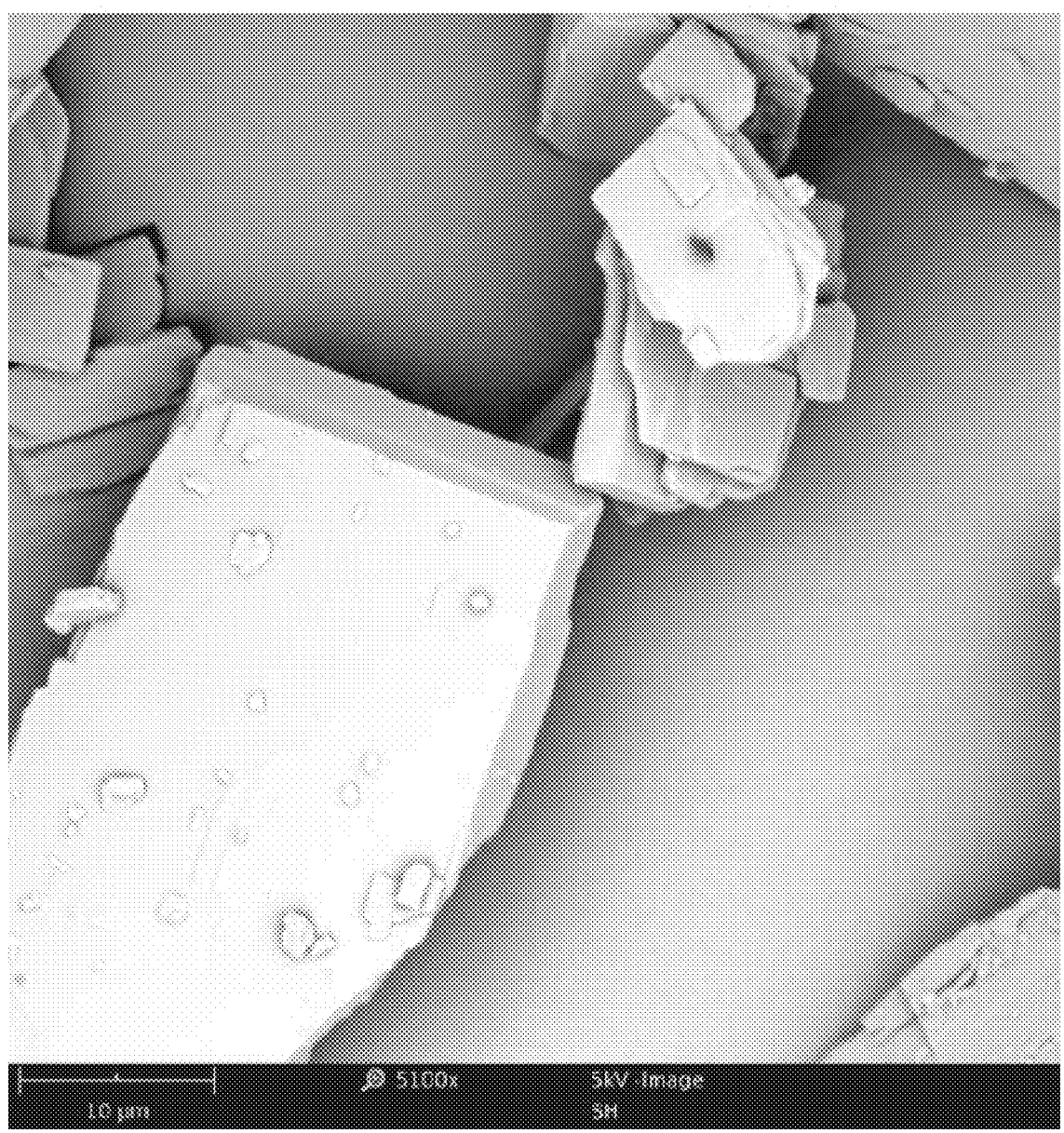
FIG. 12C: SEM images of Sample 1 (5100×).
Figure 13A:
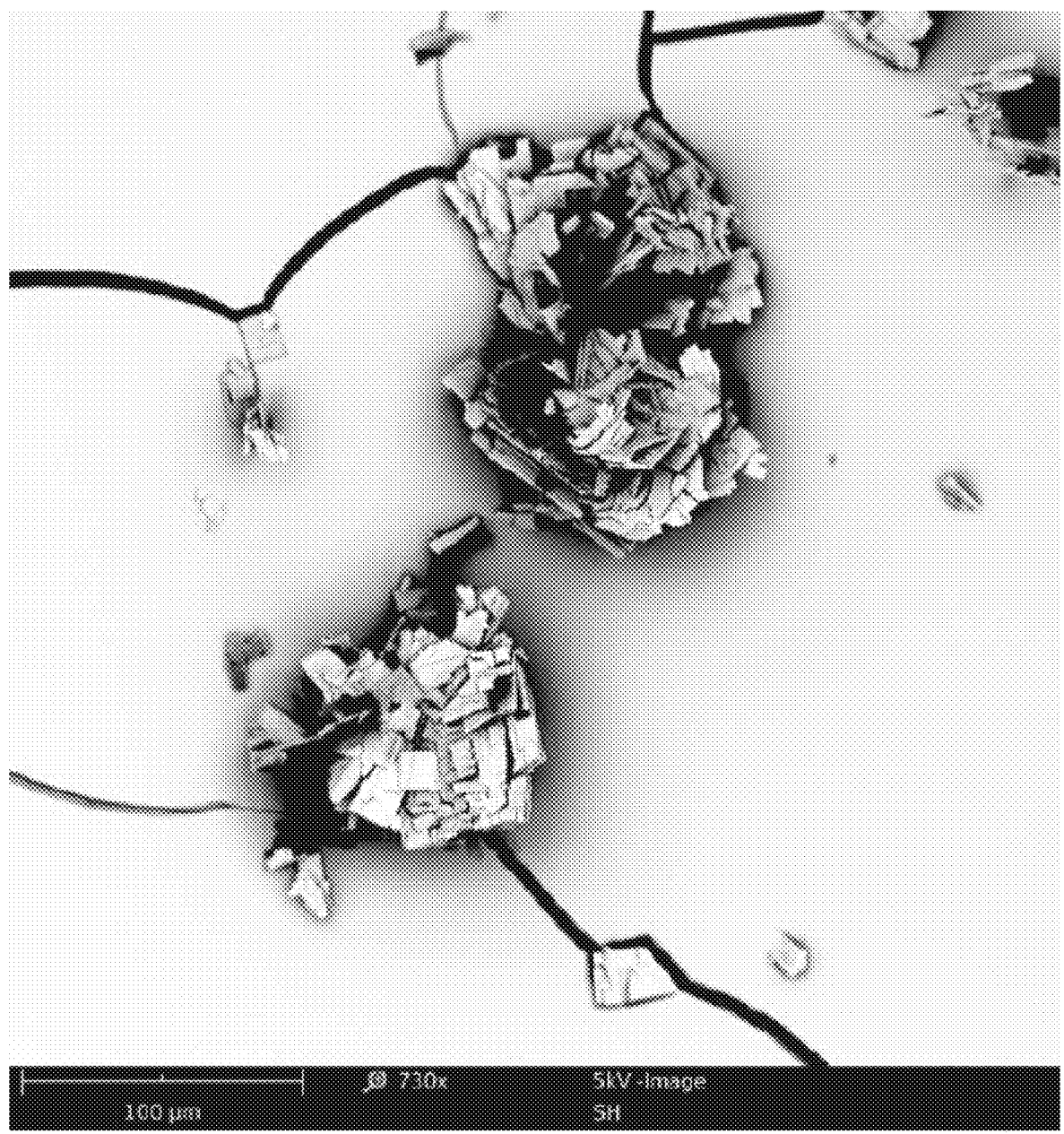
FIG. 13A: SEM images of Sample 2 (730×).
Figure 13B:
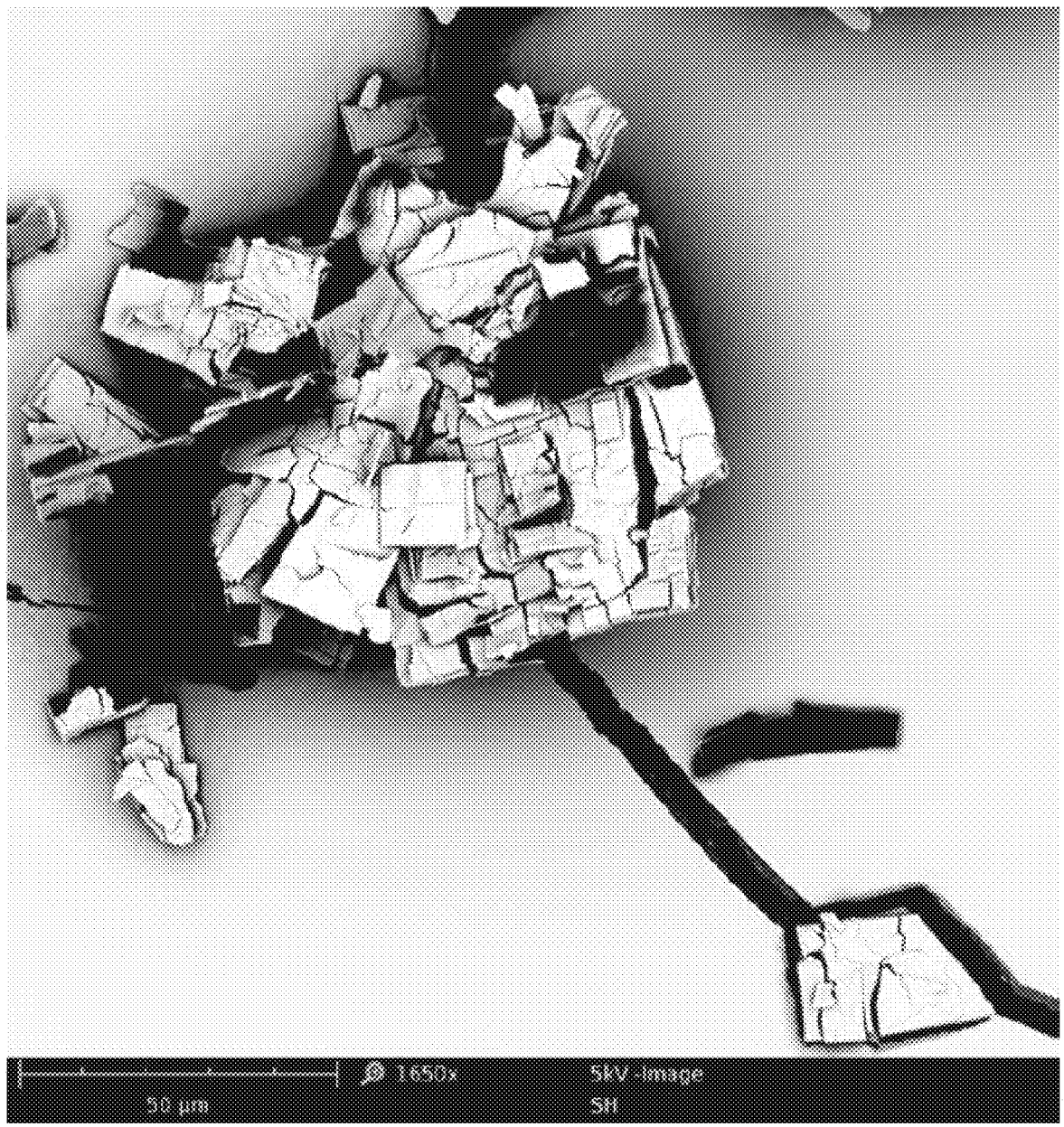
FIG. 13B: SEM images of Sample 2 (1650×).
Figure 13C:
FIG. 13C: SEM images of Sample 2 (3400×).

| Characterization Method | Sample/Method | Sample 1 | Sample 2 |
|---|---|---|---|
| XRPD | 0% RH | FIG. 4G (Form 1), FIG. 4H | FIG. 5H (Form 2), FIG. 4H |
| XRPD | 92% RH | — | FIG. 5I (Form 3), FIG. 4H |
| GVS | Uptake 0-90% RH | 1.8% wt. (reversible) (FIGS. 6A and 6B) | 6.7% wt. from 0-40% RH; 2.0% wt. from 40-90% RH (FIGS. 7A and 7B) |
| GVS | HighRH method, Table 2 | FIGS. 6C and 6D | N/A |
| GVS | HighRH_Desorp_3 method, Table 2 | FIGS. 6E and 6F | N/A |
| GVS | HighRH_DoubleCycle_2 method, Tables 3 and 4 | FIGS. 6G and 6H | N/A |
| TGA | N/A | 0.4% weight loss between ambient and 100° C. (FIG. 8, top) | 6.1% weight loss between ambient and 200° C. (FIG. 9, top) |
| DSC | N/A | Endotherm at 218° C. (onset) 150.0 J/g (melt) (FIG. 8, bottom) | Endotherm at 157° C. (onset) 87 J/g (melt), exotherm at 187° C. (recryst.), endotherm at 207° C. (onset) 33 J/g (melt as Form 1) (FIG. 9, bottom) |
| KF | N/A | 0.7% water (conducted at 200° C.) | 3.9% water (conducted at 200° C.) |
| IC | N/A | 2.0 eq (adjusted for TGA mass loss) | 1.9 eq (adjusted for TGA mass loss) |
| PLM | N/A | Crystalline (FIG. 10A) | Crystalline plates |
| SEM | N/A | Stacked plates (FIGS. 12A-12C) | Stacked plates with cracks (evidence of desolvation) (FIGS. 13A-13C) |

Figure 2A:
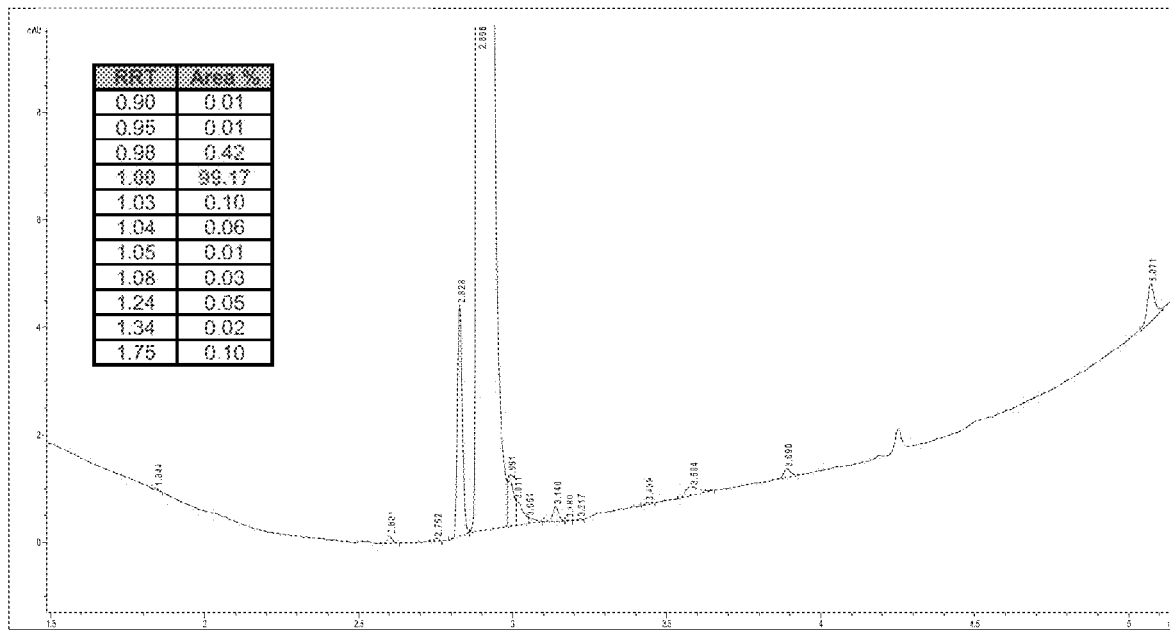
FIG. 2A: RP-HPLC Chromatogram of Sample 1 collected at 255 nm.
Figure 2B:
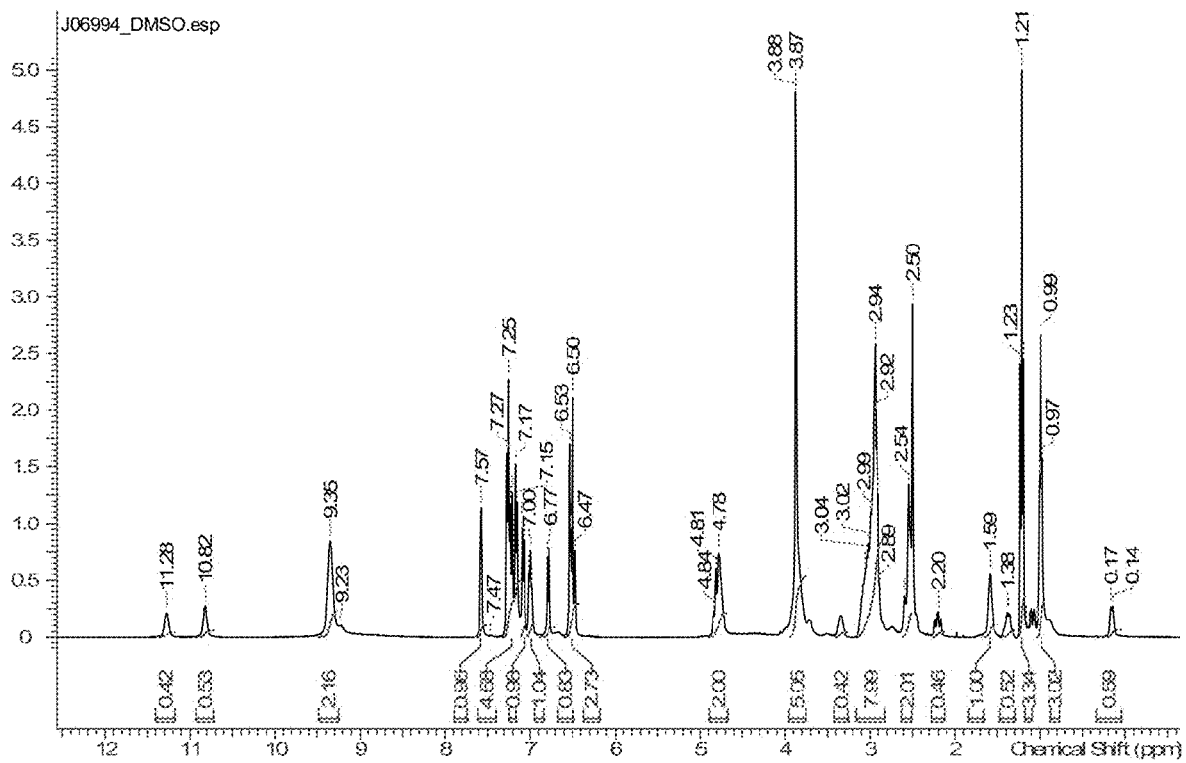
FIG. 2B: $^1$H NMR of Sample 1 collected in $d_6$-DMSO.
Figure 3A:
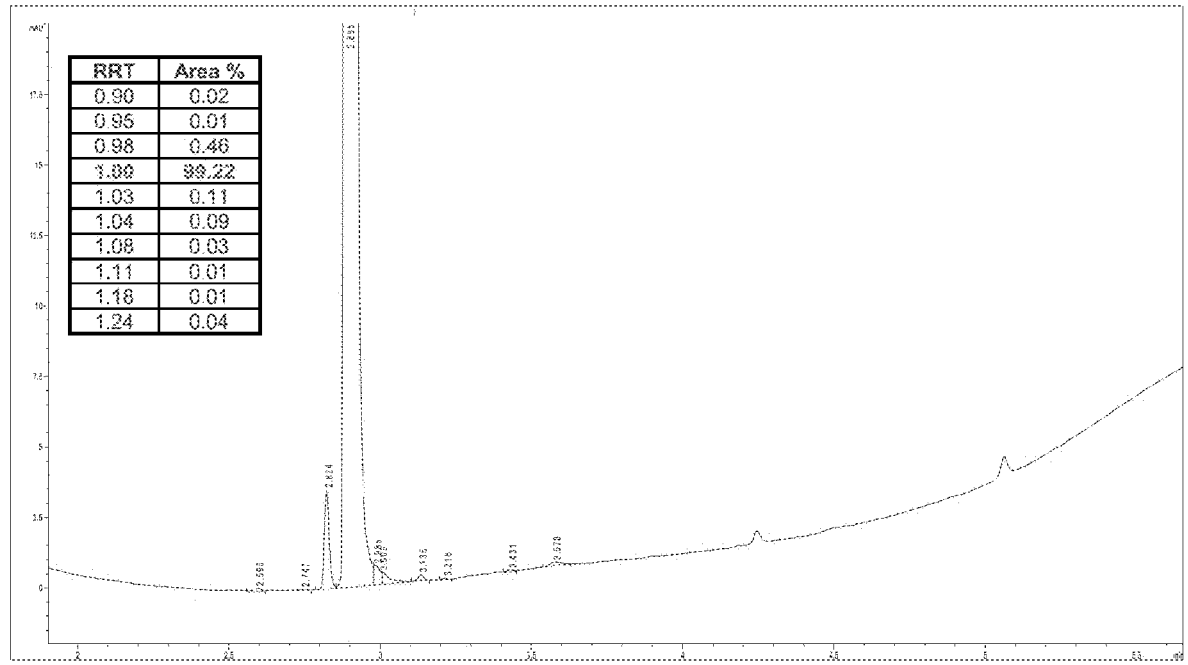
FIG. 3A: RP-HPLC Chromatogram of Sample 2 collected at 255 nm.
Figure 3B:
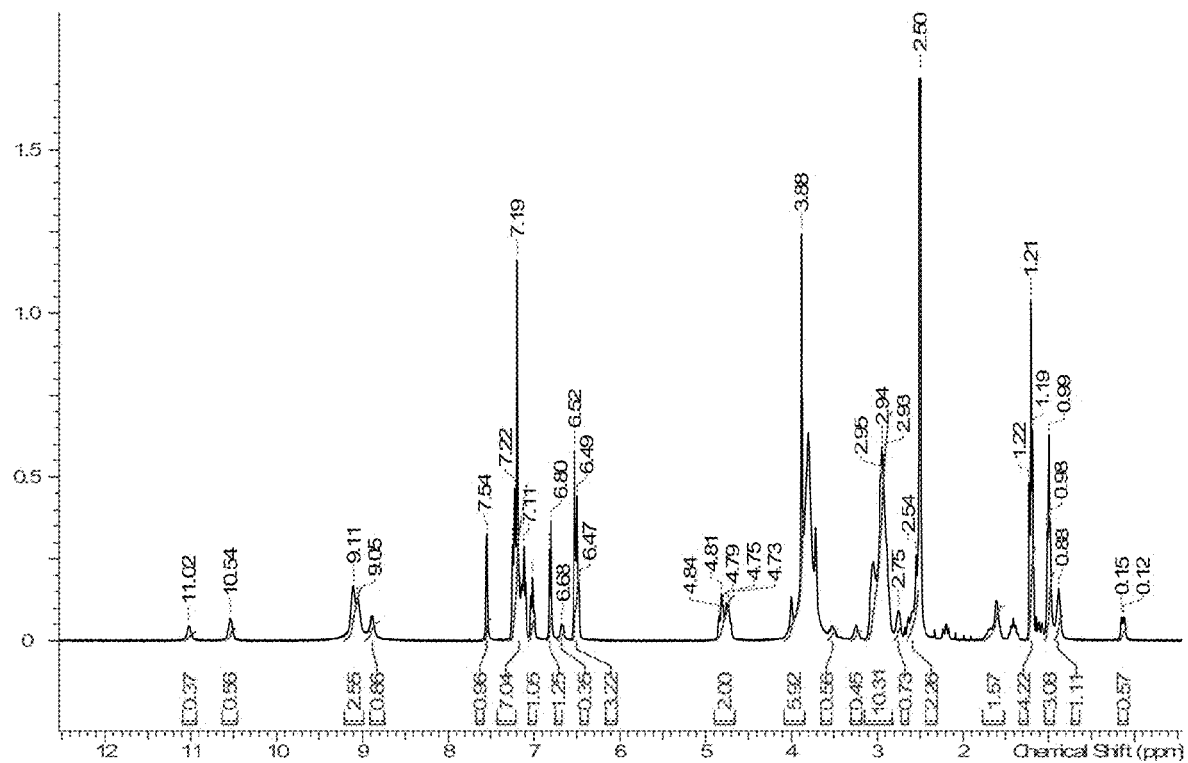
FIG. 3B: $^1$H NMR of Sample 2 collected in $d_6$-DMSO.

RP-HPLC analysis of Samples 1 and 2 showed 99.2% AUC collected at 255 nm (FIG. 2A for Sample 1, and FIG. 3A for Sample 2). $^1$H NMR of Samples 1 and 2 collected in $d_6$-DMSO are consistent with RAD1901-2HCl structure (FIG. 2B for Sample 1, and FIG. 3B for Sample 2).

Sample 1 was majorly Form 1 of RAD1901-2HCl having XRPD Pattern 1, FIG. 4G at 0% RH, with peaks summarized in Table 7. Sample 1 showed XRPD pattern slightly different at ambient RH (FIG. 4A, Table 6). Sample 2 was a mixture of Forms 2 and 3 of RAD1901-2HCl. Form 2 showed XRPD Pattern 2 (FIG. 5H, sample 2 at 0% RH, peaks summarized in Table 8) and Form 3 showed XRPD Pattern 3 (FIG. 5I, sample 2 at 92% RH, peaks summarized in Table 9).

TABLE 6

XRPD peaks of Sample 1 at ambient RH (Pattern 1)

| Caption | Angle degrees, (2θ) | Intensity (%) |
|---|---|---|
| 7.1° | 7.1 | 93.1 |
| 7.8° | 7.8 | 6.9 |
| 8.1° | 8.1 | 4.1 |
| 8.6° | 8.6 | 7.2 |
| 9.1° | 9.1 | 5.6 |
| 11.0° | 11.0 | 20.8 |
| 11.1° | 11.1 | 9.2 |
| 11.4° | 11.4 | 9.1 |
| 12.0° | 12.0 | 30.3 |
| 12.1° | 12.1 | 16.5 |
| 12.7° | 12.7 | 5.9 |
| 13.8° | 13.8 | 39.6 |
| 14.2° | 14.2 | 100.0 |
| 14.8° | 14.8 | 4.3 |
| 15.6° | 15.6 | 3.7 |
| 16.1° | 16.1 | 24.3 |
| 17.3° | 17.3 | 5.2 |
| 17.8° | 17.8 | 12.7 |
| 18.4° | 18.4 | 58.5 |
| 18.9° | 18.9 | 29.9 |
| 19.7° | 19.7 | 16.5 |
| 20.2° | 20.2 | 12.9 |
| 21.1° | 21.1 | 10.3 |
| 22.1° | 22.1 | 13.3 |
| 23.0° | 23.0 | 21.9 |
| 23.2° | 23.2 | 13.7 |
| 23.6° | 23.6 | 16.1 |
| 24.0° | 24.0 | 18.0 |
| 24.6° | 24.6 | 10.4 |
| 25.1° | 25.1 | 43.9 |
| 25.7° | 25.7 | 6.7 |

TABLE 6-continued

XRPD peaks of Sample 1 at ambient RH (Pattern 1)

| Caption | Angle degrees, (2θ) | Intensity (%) |
|---|---|---|
| 26.5° | 26.5 | 23.3 |
| 27.1° | 27.1 | 30.4 |
| 27.3° | 27.3 | 12.8 |
| 27.8° | 27.8 | 10.4 |
| 28.4° | 28.4 | 14.6 |
| 28.7° | 28.7 | 9.6 |
| 29.1° | 29.1 | 14.9 |
| 29.9° | 29.9 | 24.6 |
| 30.3° | 30.3 | 15.3 |
| 30.5° | 30.5 | 10.3 |

TABLE 7

XRPD peaks of Sample 1 at 0% RH (Pattern 1)

| Caption | Angle degrees (2θ) | Intensity (%) |
|---|---|---|
| 7.1° | 7.1 | 100.0 |
| 7.7° | 7.7 | 7.9 |
| 8.6° | 8.6 | 12.0 |
| 9.1° | 9.1 | 10.0 |
| 11.0° | 11.0 | 40.9 |
| 11.2° | 11.2 | 17.9 |
| 11.4° | 11.4 | 18.0 |
| 12.0° | 12.0 | 62.0 |
| 12.7° | 12.7 | 6.7 |
| 13.8° | 13.8 | 67.5 |
| 14.3° | 14.3 | 86.4 |
| 14.8° | 14.8 | 4.1 |
| 15.5° | 15.5 | 4.8 |
| 16.2° | 16.2 | 36.3 |
| 16.8° | 16.8 | 7.8 |
| 17.3° | 17.3 | 7.9 |
| 17.8° | 17.8 | 20.1 |
| 18.3° | 18.3 | 83.5 |
| 18.9° | 18.9 | 47.3 |
| 19.7° | 19.7 | 20.5 |
| 20.2° | 20.2 | 19.8 |
| 20.9° | 20.9 | 7.6 |
| 21.2° | 21.2 | 13.6 |
| 22.0° | 22.0 | 24.7 |
| 23.1° | 23.1 | 30.7 |
| 23.6° | 23.6 | 25.3 |
| 24.0° | 24.0 | 27.5 |
| 24.5° | 24.6 | 15.3 |
| 25.1° | 25.1 | 58.4 |
| 25.8° | 25.8 | 9.8 |
| 26.5° | 26.5 | 31.1 |
| 27.2° | 27.2 | 43.4 |
| 27.5° | 27.5 | 12.3 |
| 27.8° | 27.8 | 12.7 |
| 28.5° | 28.5 | 17.6 |
| 28.7° | 28.7 | 11.6 |
| 29.1° | 29.1 | 21.1 |
| 30.0° | 30.0 | 25.8 |
| 30.3° | 30.3 | 23.8 |
| 30.5° | 30.5 | 16.1 |

TABLE 8

XRPD peaks of Sample 2 at 0% RH (Pattern 2)

| Caption | Angle degrees (2θ) | Intensity (%) |
|---|---|---|
| 6.3° | 6.3 | 100.0 |
| 8.2° | 8.3 | 6.0 |
| 9.8° | 9.8 | 19.1 |
| 11.5° | 11.5 | 11.5 |
| 12.1° | 12.1 | 6.1 |
| 12.5° | 12.5 | 32.9 |
| 13.4° | 13.4 | 21.7 |
| 13.8° | 13.8 | 3.8 |
| 14.6° | 14.6 | 2.1 |
| 15.4° | 15.4 | 23.5 |
| 15.8° | 15.8 | 14.2 |
| 17.4° | 17.4 | 13.9 |
| 17.8° | 17.8 | 8.0 |
| 18.3° | 18.3 | 23.3 |
| 18.8° | 18.8 | 13.3 |
| 19.9° | 19.9 | 16.1 |
| 20.3° | 20.3 | 7.4 |
| 21.1° | 21.1 | 13.2 |
| 21.5° | 21.5 | 6.3 |
| 21.9° | 21.9 | 15.8 |
| 22.5° | 22.5 | 14.6 |
| 23.00 | 23.0 | 15.1 |
| 23.9° | 23.9 | 7.0 |
| 24.70 | 24.7 | 10.9 |
| 25.0° | 25.0 | 18.2 |
| 25.5° | 25.5 | 6.7 |
| 26.2° | 26.2 | 9.9 |
| 27.0° | 27.0 | 6.2 |
| 28.0° | 28.0 | 18.3 |
| 29.3° | 29.3 | 4.8 |
| 29.9° | 29.9 | 20.4 |
| 30.3° | 30.3 | 6.4 |

TABLE 9

XRPD Peak of Sample 2 at 92% RH (Pattern 3)

| Caption | Angle degrees (2θ) | Intensity (%) |
|---|---|---|
| 5.8° | 5.8 | 100 |
| 8.1° | 8.1 | 10 |
| 9.5° | 9.5 | 35.2 |
| 11.5° | 11.5 | 33.6 |
| 12.4° | 12.4 | 29.5 |
| 12.6° | 12.7 | 22 |
| 13.1° | 13.1 | 34.5 |
| 13.6° | 13.6 | 13.1 |
| 15.1° | 15.1 | 34.8 |
| 16.1° | 16.1 | 16.4 |
| 16.9° | 16.9 | 6.7 |
| 17.4° | 17.4 | 19 |
| 18.0° | 18.0 | 17.5 |
| 18.4° | 18.4 | 9.7 |
| 18.9° | 18.9 | 19.1 |
| 19.9° | 19.9 | 11.4 |
| 21.3° | 21.3 | 50.1 |
| 21.7° | 21.7 | 27.5 |
| 22.4° | 22.4 | 19.3 |
| 22.8° | 22.8 | 29.9 |
| 23.3° | 23.3 | 40 |
| 24.2° | 24.2 | 22.2 |
| 24.8° | 24.8 | 41.8 |
| 25.4° | 25.4 | 18 |
| 26.2° | 26.2 | 19.5 |
| 27.4° | 27.4 | 26.9 |
| 27.6° | 27.6 | 23.3 |
| 28.9° | 28.9 | 11.1 |
| 29.3° | 29.3 | 10.2 |
| 30.5° | 30.5 | 14.3 |

Form 1 was stable after storage at 40° C./75% RH for 1 week and after exposure to 0-90% RH in a GVS, as confirmed by unchanged XRPD pattern (Pattern 1) of Form 1 sample pre- and post-GVS. However, Form 1 was converted to Form 3 after storage at 25° C./97% RH for 1 week.

Figure 6A:
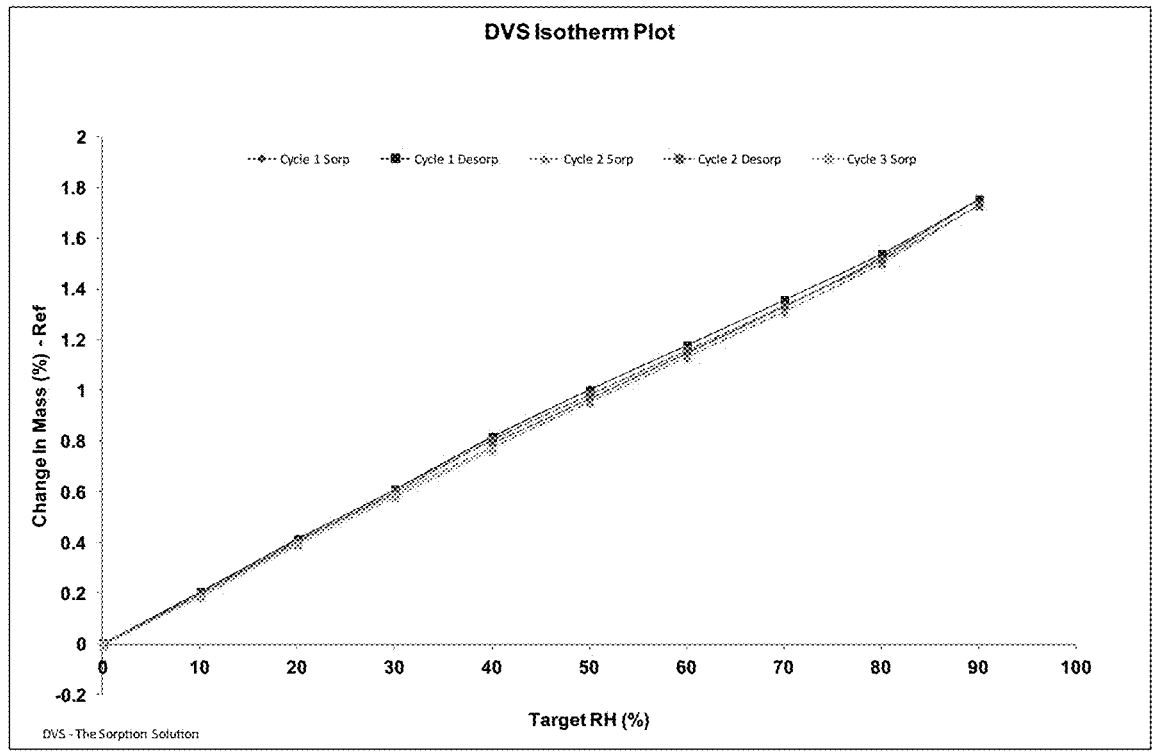
FIG. 6A: GVS Isotherm Plot for Sample 1 collected from 0 to 90% RH.
Figure 6B:
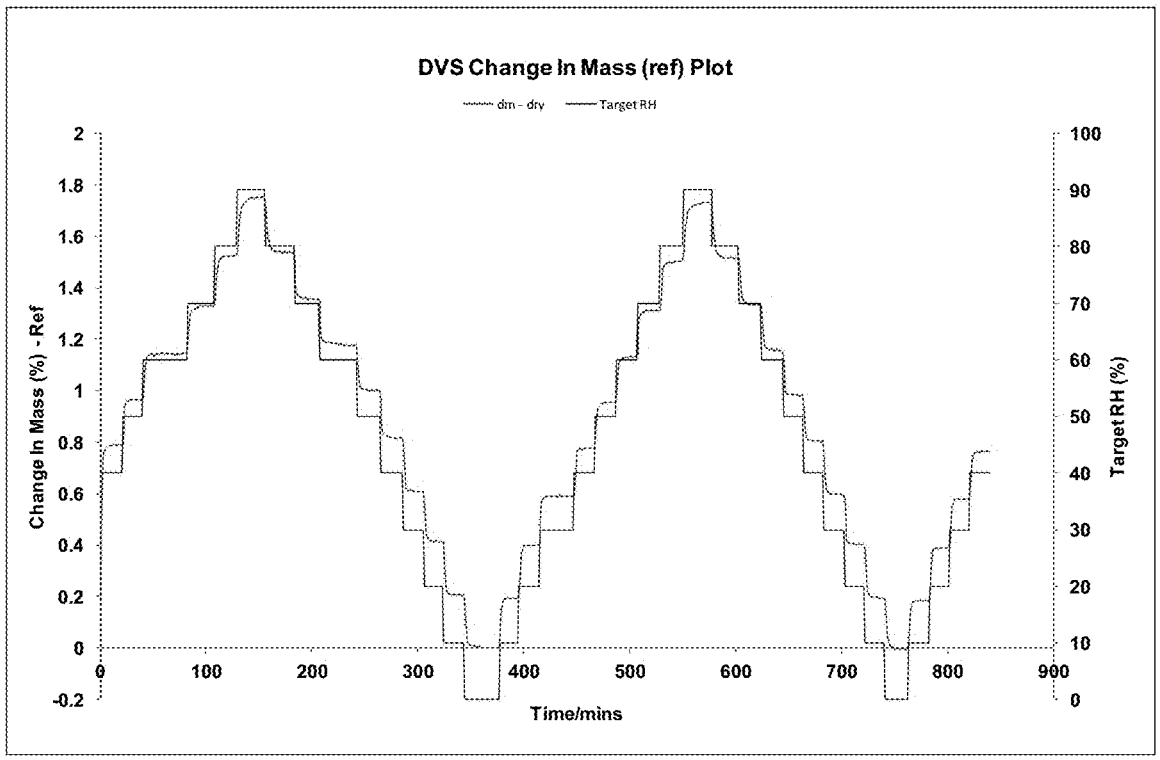
FIG. 6B: GVS Kinetic Plot for Sample 1 collected from 0 to 90% RH.

Form 1 was relatively non-hygroscopic between 0 and 90% RH as shown in GVS data (FIGS. 6A-6B). No changes were observed in the XRPD pattern pre- and post-GVS analysis (FIG. 4D).

Form 1 was stable to storage at 40° C./75% RH for 7 days (from XRPD analysis), but storage at 25° C./97% RH for 7 days resulted in conversion towards a hydrated state Form 3 (see FIG. 4B).

An overlay of the new patterns obtained upon storage of Sample 1 and Sample 2 at elevated conditions is provided in FIG. 5C, which are substantially consistent with Form 3. Importantly, this indicates that upon prolonged exposure to high RH, Sample 1 (Form 1) was converted to the hydrate Form 3.

To further explore the humidity behavior of Sample 1 (Form 1) upon exposure to high RH (>90%), custom GVS experiments were designed and carried out. Initially, the sample was treated by holding at 90 and then 95% RH for ~12 hours to see if hydrate formation could be observed (HighRH method of Steps 1 and 2 of Table 2, FIGS. 6C-6D).

Figure 6C:
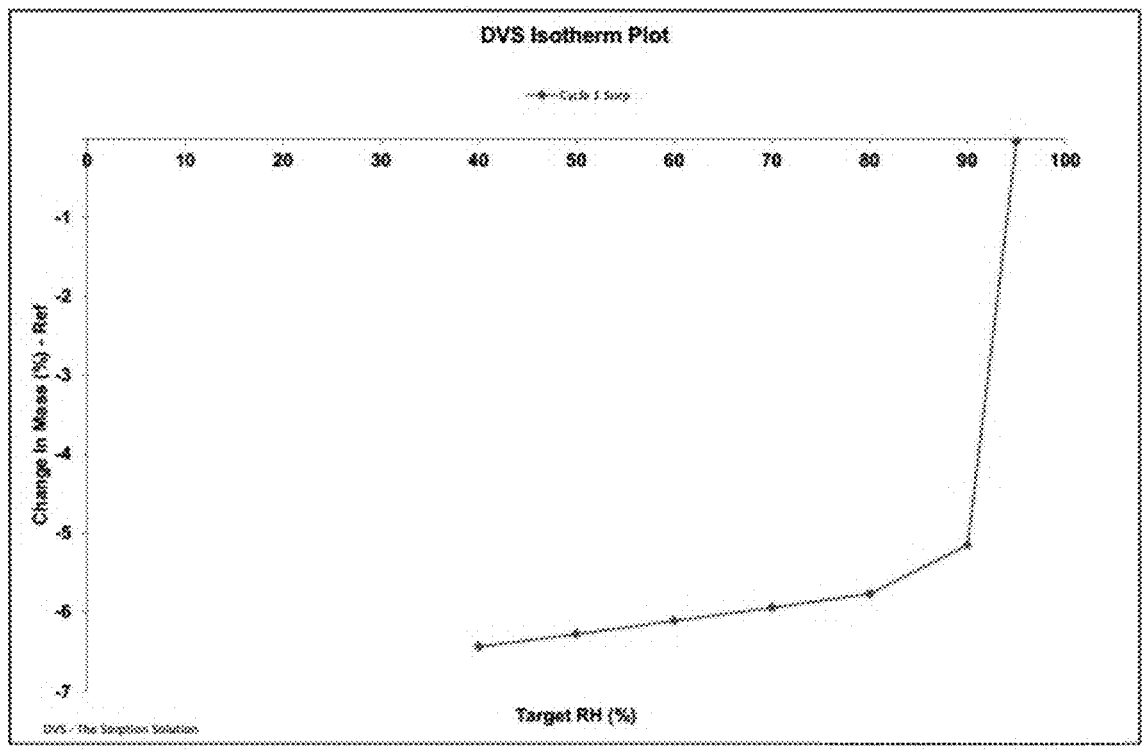
FIG. 6C: GVS Isotherm Plot for Sample 1 collected from 40 to 95% RH with GVS method HighRH.
Figure 6D:
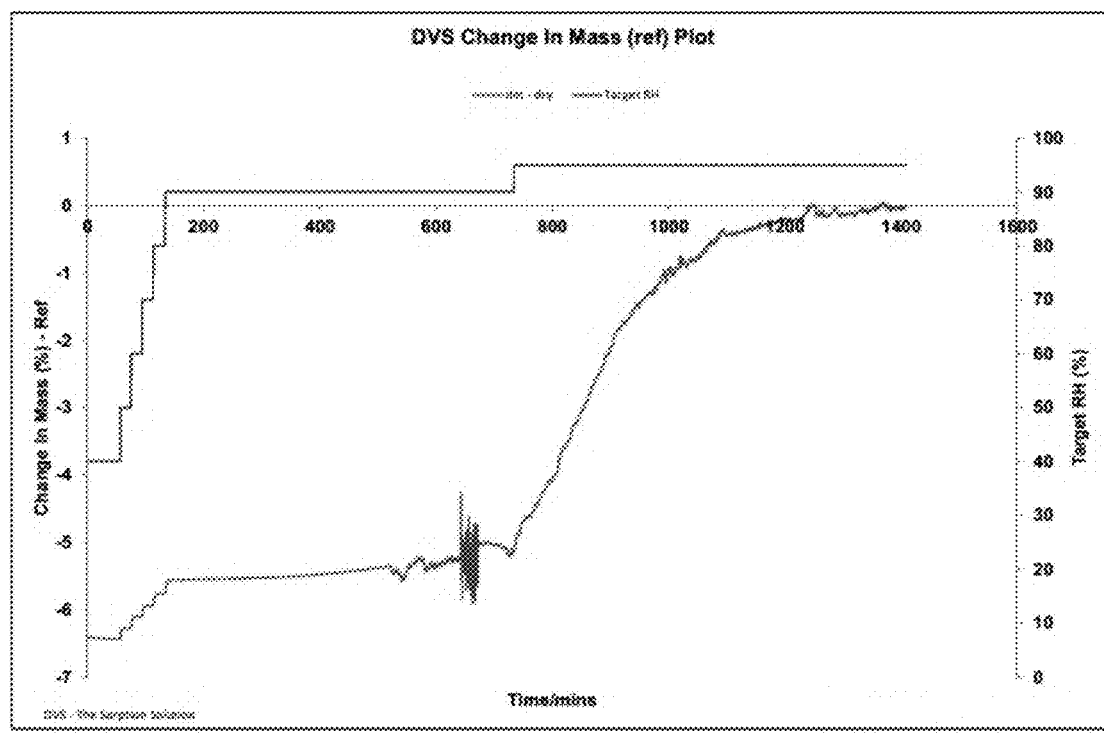
FIG. 6D: GVS Kinetic Plot for Sample 1 collected from 40 to 95% RH with GVS method HighRH.

FIGS. 6C-6D (HighRH method of Steps 1 and 2 of Table 2) shows Sample 1 (Form 1) took up 5-6% wt. when held at 95% RH for ~12 hours, indicating hydrate formation. XRPD analysis of the sample post-GVS experiment (HighRH, red in FIG. 4E) showed significant changes compared to that of Form 1 (black in FIG. 4E), with similarities to both the hydrated state Form 3 and the anhydrous Form 1. FIG. 4E suggested a mixture of states or incomplete conversion from Sample 1 to the hydrate form.

Figure 6E:
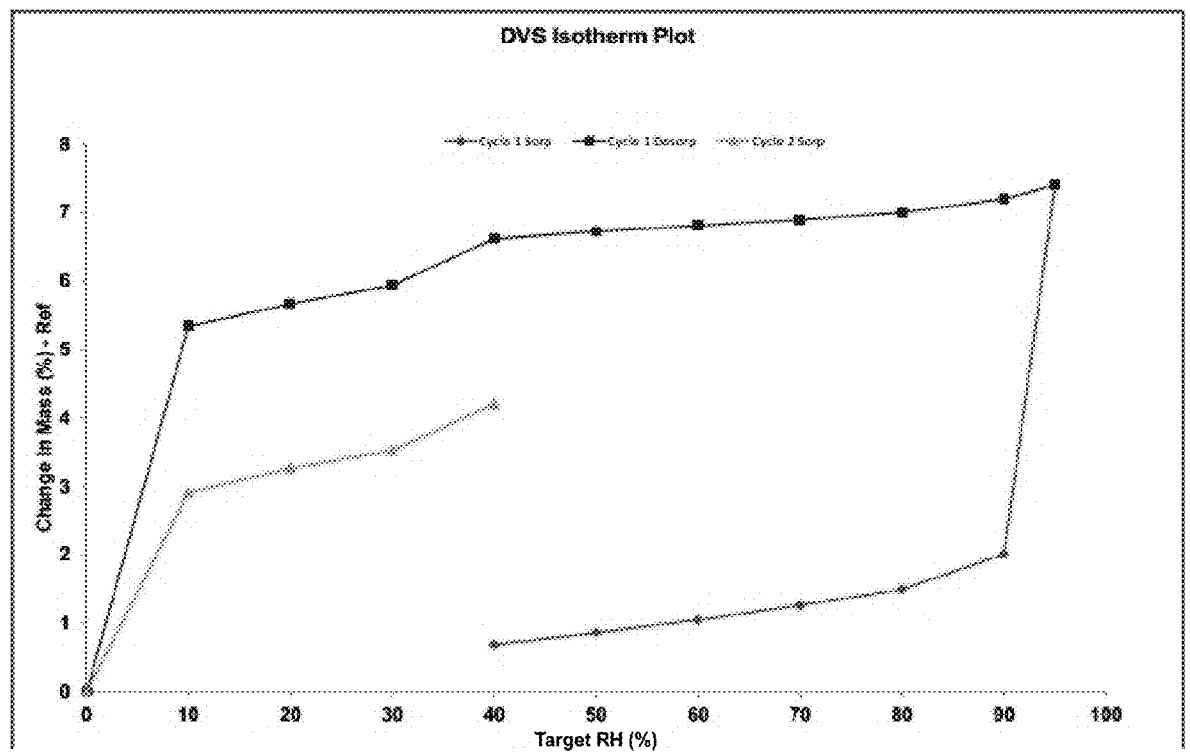
FIG. 6E: GVS Isotherm Plot for Sample 1 collected over a single cycle with GVS method HighRH_Desorp_3.
Figure 6F:
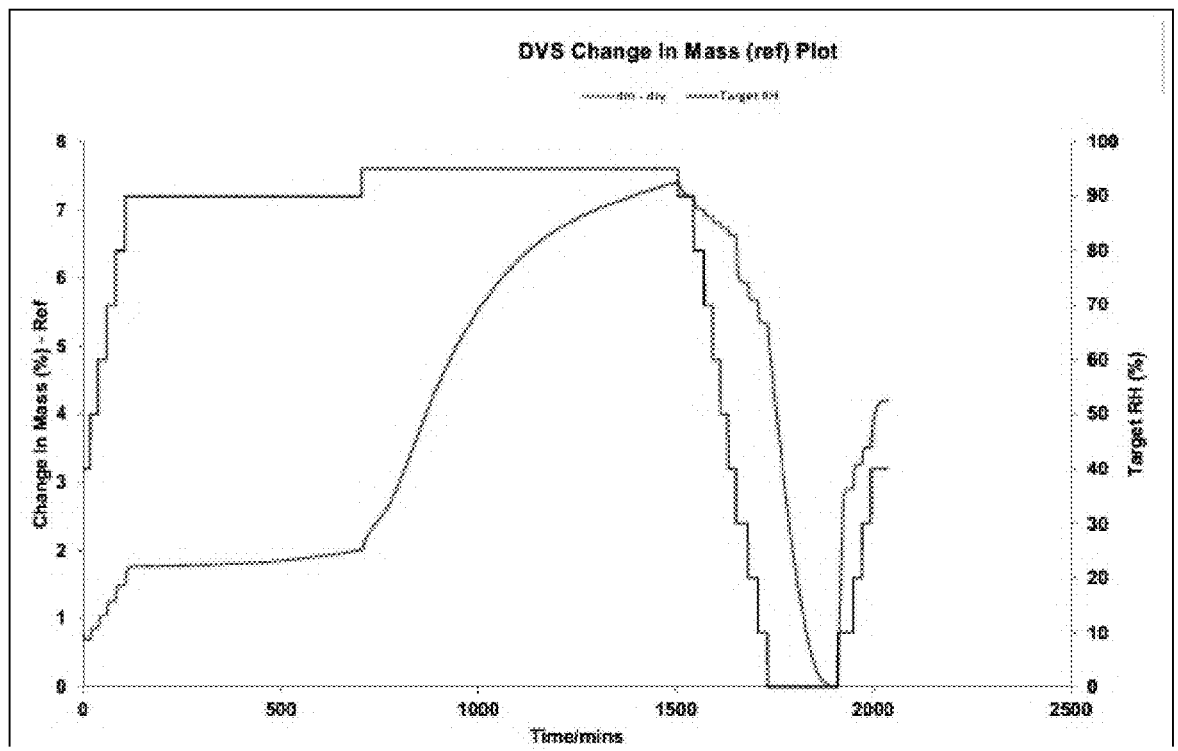
FIG. 6F: GVS Kinetic Plot for Sample 1 collected over a single cycle with GVS method HighRH_Desorp_3
Figure 6G:
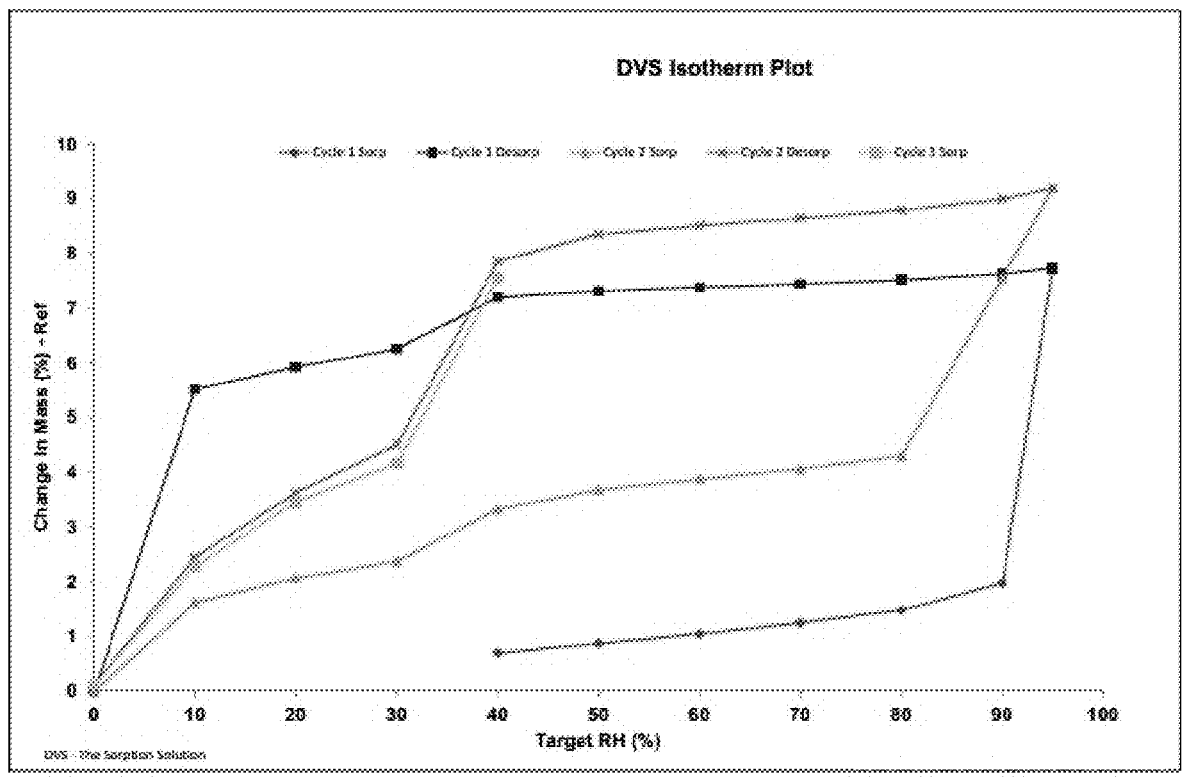
FIG. 6G: GVS Isotherm Plot for Sample 1 collected over a double cycle with GVS method HighRH_DoubleCycle_2.
Figure 6H:
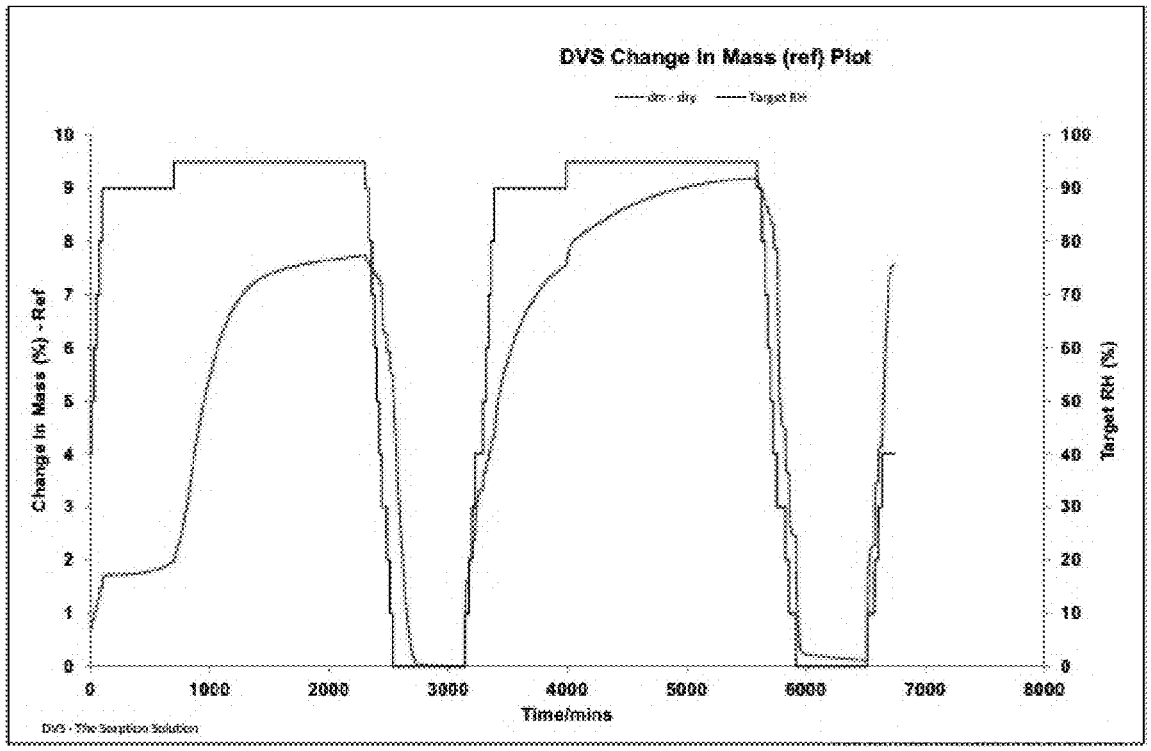
FIG. 6H: GVS Kinetic Plot for Sample 1 collected over a double cycle with GVS method HighRH_DoubleCycle_2.

To test the stability of the hydrated state, GVS method HighRH_Desorp_3 was designed with a desorption step and subsequent adsorption (see Table 2 with steps 1-4, FIGS. 6E-6F).

The GVS data in FIGS. 6E-6F shows that the hydrated state (at 95% RH) was stable to desorption until near 0% RH, and upon adsorption from 0 to 40% RH, the sample did not convert back to anhydrous Form 1, but instead irreversibly converted to a new state (indicating a mixture of hydrate and anhydrous). Furthermore, the shape of the adsorption step from 0 to 40% was observed to be highly similar to that of Form 2 (see FIG. 7A). XRPD analysis of the sample post-GVS experiment ('HighRH_Desorp_3') confirmed that a mixture of Form 1 and Form 3 was present (see FIG. 4E), as shown by starred peaks (indicating peaks present in either the XRPD pattern of the anhydrous or hydrated form). The XRPD patterns obtained for Sample 1 post GVS of HighRH_Desorp_3 is shown in green.

Finally, to ensure complete conversion to the anhydrous and hydrated forms, a GVS experiment was designed to increase both the length of the desorption step at 0% RH, and the adsorption step at 95% RH, respectively (Table 3). Based on the weight stabilization observed in the kinetic plots for Sample 1 in HighRH and HighRH_Desorp_3 methods discussed above (FIGS. 6D and 6F), a holding time of 800 mins at 0% RH and 1600 mins at 95% RH were chosen. A double cycle was also recorded for this experiment to observe whether the sample would return to Form 1 or form a mixed anhydrous/hydrated species (see Table 3, FIGS. 6G-6H).

The GVS data (FIGS. 6G-6H) show that after complete desorption at 0% RH, and subsequent re-adsorption, the sample continued to uptake water and formed a mixed anhydrous/hydrated species. This species converted to the hydrate at 90-95% RH (Form 3), which remained stable during desorption until 40%, below which the sample desorbed sharply. Subsequent adsorption from 0 to 40% RH followed this step-wise transition, which can be clearly observed in the GVS Isotherm Plot of Sample 2 (see FIG. 7A). This GVS data provides clear evidence that the Sample 1/Form 1 material irreversibly converted to a hydrate (Form 3) under exposure to high RH (>90%), and upon desorption shifts into an equilibrium between the anhydrous state (Form 2) and the hydrated state (Form 3). XRPD analysis of the sample post-GVS experiment ('HighRH DoubleCycle 2') confirmed the formation of the hydrate (Form 3), see FIG. 4F.

To fully characterize the polymorphic behavior of Samples 1 and 2 at variable humidity, and to collect reference XRPD patterns for the 'pure' anhydrous Form 1 and Form 2 material, and 'pure' hydrated Form 3 material, Variable Humidity (VH) XRPD experiments were conducted on Samples 1 and 2. Initially, VH-XRPD experiments were conducted using Sample 1, and XRPD diffractograms were collected at selected humidity values, in line with those collected during GVS experiments (see FIGS. 6E-6F). XRPD diffractograms were collected initially at ambient RH, then collected over 24 hours at ~95% RH and finally collected during desorption steps to 0% RH and over 10 hours at 0% RH (see FIG. 4C). Full method details are provided in Table 10 below.

TABLE 10

Experimental conditions for collection of VH experiment on Sample 1 (sample: J06994__D8__VH, method: P2803-06NOV15)

| Desired Humidity | Recorded humidity | Measured delay (hold) time (hrs) | Scan time (hrs) |
|---|---|---|---|
| Ambient | 53.7 | 0 | 0.69* |
| 94 | 96.1 | 2 | 0.69 |
| 94 | 95.3 | 2 | 0.69 |
| 94 | 94.9 | 2 | 0.69 |
| 94 | 94.7 | 2 | 0.69 |
| 94 | 94.5 | 2 | 0.69 |
| 94 | 94.5 | 2 | 0.69 |
| 94 | 94.4 | 2 | 0.69 |
| 94 | 94.3 | 2 | 0.59 |
| 94 | 94.3 | 2 | 0.69 |
| 94 | 94.2 | 2 | 0.69 |
| 80 | 82.4 | 1 | 0.69 |
| 70 | 72.8 | 1 | 0.69 |
| 60 | 63.6 | 1 | 0.69 |
| 50 | 51.7 | 1 | 0.69 |
| 40 | 40.3 | 1 | 0.69 |
| 30 | 29.3 | 1 | 0.69 |
| 20 | 17.3 | 1 | 0.69 |
| 10 | 5.9 | 1 | 0.69 |
| 0 | 0 | 1 | 0.69 |
| 0 | 0 | 4 | 0.69 |
| 0 | 0 | 4 | 0.69 |
| 10 | 5.8 | 2 | 0.69 |
| 20 | 17.2 | 2 | 0.69 |
| 30 | 29.1 | 2 | 0.69 |
| 40 | 40.0 | 2 | 0.69 |

*each scan was 41 m 28 s (0.69 hrs)

The VH-XRPD experiment was unable to show a direct conversion from the starting material Sample 1 (Form 1) to the hydrated state (Form 3) over 24 hours at ~95% RH (see FIG. 4C). However, there were subtle changes in the diffractogram pattern observed at ~95% RH, compared to that of the starting material at ambient RH and at 0% RH (see starred peaks). These changes included a shoulder at 12 degrees 2θ and an additional peak at 19 degrees 2θ and indicated a slow conversion towards the hydrated state (see post 25/97' in FIG. 4C). Thus, Form 1 may have converted to Form 3 (hydrate) over time, as supported by GVS data (FIGS. 6E-6F). One possible explanation for the slower kinetics in VH-XRPD is that VH-XRPD experiments relied on changes in the crystal structure of a sample at an exposed surface layer to varying humidity, whereas GVS experiments allowed all surfaces of the sample to be exposed as the sample was suspended in a wire basket.

Thermal analysis of the supplied materials showed that Sample 1 was anhydrous (by TGA and KF), and had no thermal events prior to melt or degradation. In comparison, Sample 2 had a complex thermal profile by DSC (see FIG. 9B) and was found to be a hydrate (by TGA and KF). The DSC trace showed that Sample 2 desolvated upon heating from ambient to 150° C., melted at ~157° C. and recrystallized at ~187° C. (see FIG. 9B). TGA data showed that this desolvation event corresponded to a loss of 6.2% weight, equivalent to 2 molecules of water.

Variable Temperature XRPD (VT-XRPD) experiments were therefore conducted to examine the thermal behavior of Sample 2 observed by DSC (see FIG. 9B). VT-XRPD analysis shows that Sample 2 converted to the anhydrous state (Form 2, red) upon heating above 100° C., then melted and recrystallized at ~175° C. (blue) as Form 1 material (FIG. 5D).

This indicates that Sample 2 as a mixture of Forms 2 and 3 can be converted to Form 1 by recrystallization above 175° C. However, it is clear that Form 1 material irreversibly converted to the hydrate Form 3 under exposure to high RH (>90%).

VH-XRPD experiments were also conducted using Sample 2 and XRPD diffractograms were collected at selected humidity values of 0% RH (Table 12) and 90% RH (Table 11, to obtain reference XRPD patterns for the 'pure' anhydrous Form 2 and 'pure' hydrated Form 3 respectively. The GVS Kinetic Plot collected for Sample 2 (see FIG. 7B) indicated relatively fast kinetics for conversion from anhydrous to hydrated form, therefore XRPD patterns were collected at time points of up to 10-14 hours (see FIGS. 5E-5F).

TABLE 11

Experimental conditions for collection of VH experiment on Sample 2 at high RH (sample: J06993_D8_VH_90, method: P2803-11NOV15)

| Desired humidity | Recorded humidity | Measured delay (hold) time (hrs) | Scan time (hrs) |
|---|---|---|---|
| 40 | 41.8 | 0 | 0.69 |
| 90 | 93.4 | 2 | 0.69 |
| 90 | 92.1 | 2 | 0.69 |
| 90 | 91.6 | 2 | 0.69 |
| 90 | 91.6 | 2 | 0.69 |

TABLE 12

Experimental conditions for collection of VH experiment on Sample 2 at 0% RH (sample: J06993_D8_VH_0, method: P2803-12NOV15)

| Desired humidity | Recorded humidity | Measured delay (hold) time (hrs) | Scan time (hrs) |
|---|---|---|---|
| 0 | 0 | 2 | 0.69 |
| 0 | 0 | 2 | 0.69 |
| 0 | 0 | 2 | 0.69 |
| 0 | 0 | 2 | 0.69 |
| 0 | 0 | 0.69 | 0.69 |

As shown in FIG. 5E, slight changes in the XRPD pattern of Sample 2 were observed between ambient (42% RH) and 92-93% RH (see starred peaks), showing conversion toward the hydrated state (as represented by the XRPD pattern post storage at 25° C./97% RH). However, the kinetics remained relatively slow. Based on these observations, the XRPD pattern for anhydrous Sample 2 (at 0% RH) was collected after drying a sample in a vacuum oven (RT, 8 hours) (see FIG. 5F). The XRPD pattern collected at 0% RH was consistent with a sample of anhydrous Sample 2 produced by heating to 100° C. on a VT-XRPD stage (see experimental section above and FIG. 5D), and therefore provided a reference for the anhydrous Form 2.

Form 3 in Sample 2 was converted to Form 2 when Sample 2 was heated to 100° C. Sample 2 started to melt around 160° C. and recrystallized as Form 1 at above 175° C. The characterization data of Samples 1 and 2 are summarized in Table 5.

Figure 7A:
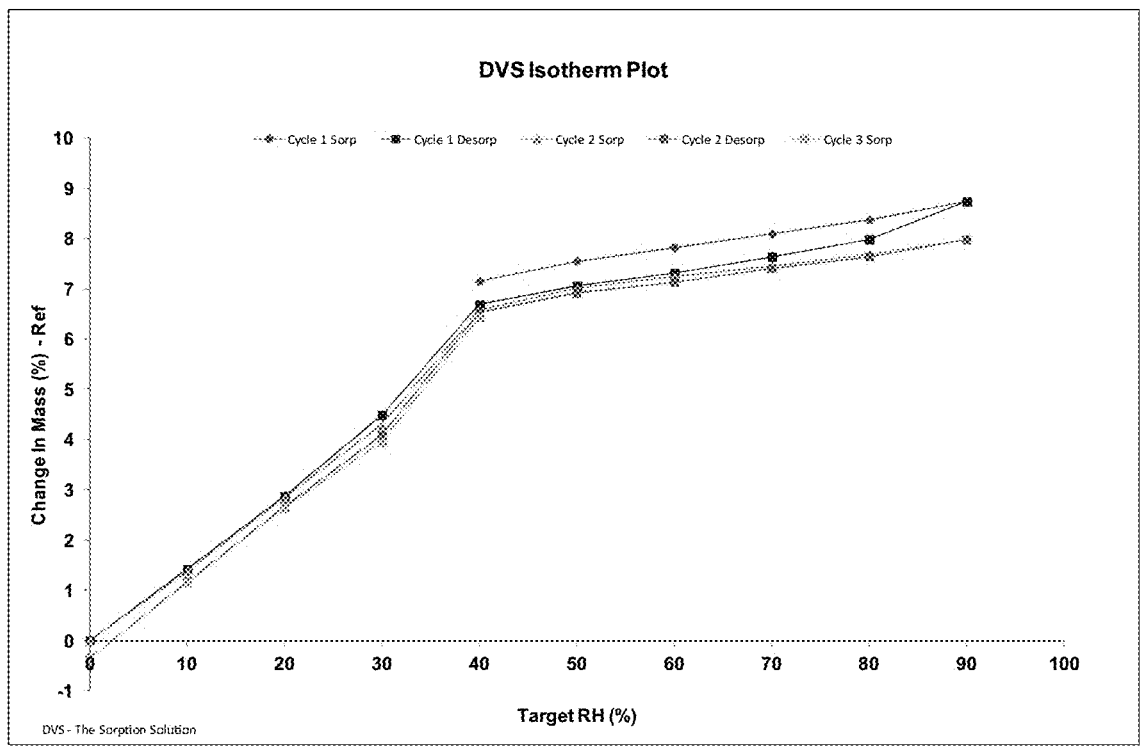
FIG. 7A: GVS Isotherm Plot for Sample 2 collected from 0 to 90% RH.
Figure 7B:
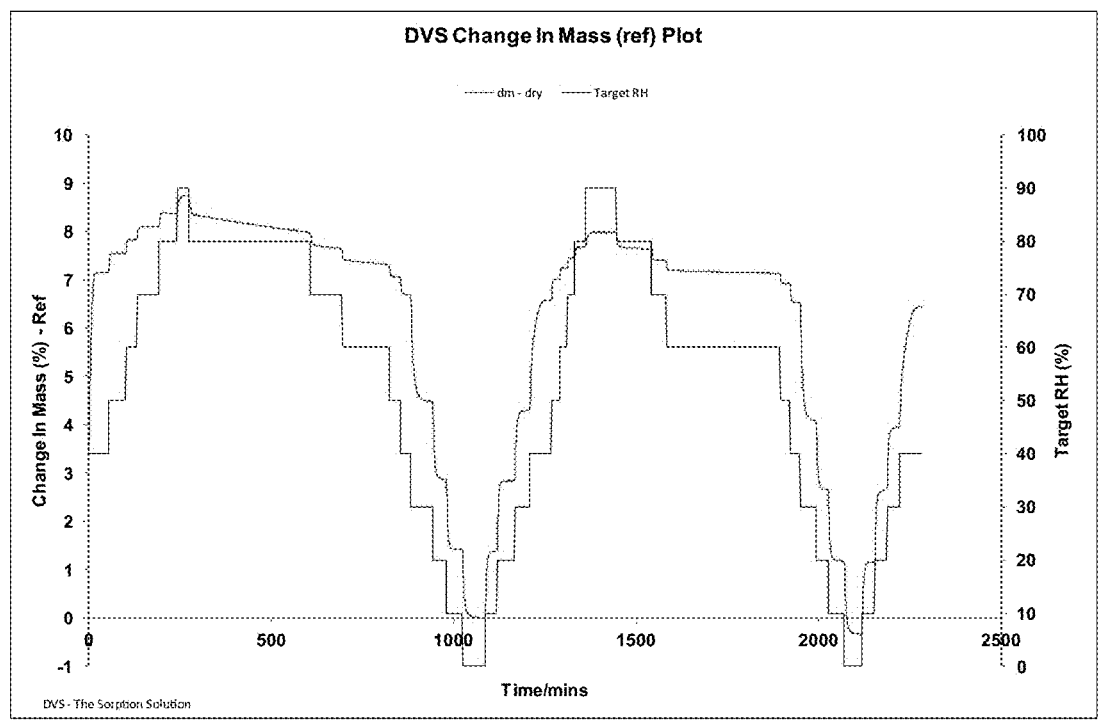
FIG. 7B: GVS Kinetic Plot for Sample 2 collected from 0 to 90% RH.

GVS experiments showed that Sample 2 was hygroscopic with a mass uptake of 6.7% wt. from 0% to 40% RH, plateauing above 40% RH (2.0% wt. from 40-90% RH) (see FIGS. 7A-7B). Thus, an equilibrium existed between the anhydrous and hydrated states for Sample 2 at near ambient RH (e.g., 40-65% RH).

The XRPD pattern collected for Sample 2 varied depending on the prevailing RH during measurement. For XRPD diffractograms pre- and post-GVS, see FIG. 5G, which showed that a mixture of Form 2 and Form 3 existed in between 0% and 90% RH (post GVS).

Example 2. Solubility Assessment of Polymorphic Forms of RAD1901-2HCl

Solubility assessment was carried out on the Sample 1 of RAD1901-2HCl (majorly Form 1 shown by XRPD) in 24 solvent systems in HPLC vials (sample IDs: A1 to A24). RAD1901-2HCl (25 mg) was treated with increasing volumes of solvent until the material fully dissolved or until a maximum of 60 vol had been used (Table 13).

TABLE 13

Solubility assessment and polymorph screen on Form 1 of RAD1901-2HCl

| Sample ID | Solvent | 10 vol. | 20 vol. | 40 vol. | 60 vol. | Cooled to 5° C. | After 50/RT maturation | Evaporation | XRPD | FIG. No. |
|---|---|---|---|---|---|---|---|---|---|---|
| A1 | n-Heptane | X | X | X | X | N/A | X | N/A | Form 1 | 14A |

TABLE 13-continued

Solubility assessment and polymorph screen on Form 1 of RAD1901-2HCl

| Sample ID | Solvent | 10 vol. | 20 vol. | 40 vol. | 60 vol. | Cooled to 5° C. | After 50/RT maturation | Evaporation | XRPD | FIG. No. |
|---|---|---|---|---|---|---|---|---|---|---|
| A2 | Propyl acetate | X | X | X | X | N/A | X | N/A | Form 1 | 14A |
| A3 | Ethyl acetate | X | X | X | X | N/A | X | N/A | Form 1 | 14A |
| A4 | Isopropyl acetate | X | X | X | X | N/A | X | N/A | Form 1 | 14A |
| A5 | MIBK | X | X | X | X | N/A | X | N/A | Form 1 | 14A |
| A6 | 2-propanol | X | X | X | X | N/A | X | N/A | Form 3* | 14C |
| A7 | MEK | X | X | X | X | N/A | X | N/A | Form 1* | 14A |
| A8 | 1-propanol | X | X | X | X | N/A | X | N/A | Form 1 | 14A |
| A9 | Acetone | X | X | X | X | N/A | X | N/A | Form 3* | 14C |
| A10 | Ethanol | X | X | X | X | N/A | X | N/A | Form 1 | 14A |
| A11 | Dimethyl sulfoxide | S | | | S | N/A | S | S | — | |
| A12 | Water | +/− | S | | S | N/A | Solid | | Form 3 | 14C |
| A13 | TBME | X | X | X | X | N/A | X | N/A | Form 1 | 14B |
| A14 | 1,4-Dioxane | X | X | X | X | N/A | X | N/A | Form 1 | 14B |
| A15 | Toluene | X | X | X | X | N/A | X | N/A | Form 1 | 14B |
| A16 | 1,2-dimethoxyethane | X | X | X | X | N/A | X | N/A | Form 1 | 14B |
| A17 | Tetrahydrofuran | X | X | X | X | N/A | X | N/A | Form 1 | 14B (THF) |
| A18 | Dichloromethane | X | X | X | X | N/A | X | N/A | Form 1 | 14B |
| A19 | Acetonitrile | X | X | X | X | N/A | X | N/A | Form 1 | 14B (ACN) |
| A20 | Methanol | +/− | S | | | Platelet crystal | N/A | N/A | Form 3 | 14C |
| A21 | Nitromethane | X | X | X | X | N/A | S | Solids | Form 1 | 14B |
| A22 | 10% water/EtOH | +/− | S | | | Some crystal | N/A | N/A | Form 3* | 14C |
| A23 | 10% water/IPA | X | X | +/− | S | S | N/A | Solids, green solution | Form 3 | 14C |
| A24 | 10% water/THF | X | X | +/− | S | S | N/A | Solids | Form 3 | 14C |

Legend: X = suspension; S = solution; +/− = nearly dissolved; *= poorly crystalline; N/A = not applicable After each addition of solvent, the system was stirred for 5 to 10 minutes at 25° C., then shaken at 50° C. for 5 to 10 minutes, and observations made. Samples were allowed to stand at room temperature for 5 min before the addition of a new aliquot of solvent. After the assessment was completed, the suspensions obtained were matured (maturation) and the clear solutions were cooled (cooling) and slowly evaporated (evaporation) as described below. All solids recovered from maturation, cooling and evaporation experiments were analyzed by high resolution XRPD.

The suspensions obtained during the solubility assessment were matured by shaken in a maturation chamber between 50° C. and RT (8 hr per cycle) for up to 5 days. Then the mixture was allowed to stand at room temperature for 10 minutes. The resulting solids were filtered and air dried and analyzed by XRPD. The clear solutions obtained during maturation were evaporated in ambient conditions and the resulting residues were analyzed by XRPD.

The clear solutions obtained during the course of the solubility assessment were cooled on a Polar Bear device from 50° C. to 5° C. at 0.1° C./min. Solids obtained upon cooling were recovered from the vials, air dried and analyzed by XRPD. If no solid was obtained, the solutions were evaporated slowly through a needle inserted into the septum cap of the vial until a solid appeared at ambient conditions and the resulting solids were filtered, air dried and analyzed by XRPD.

Figure 14A:
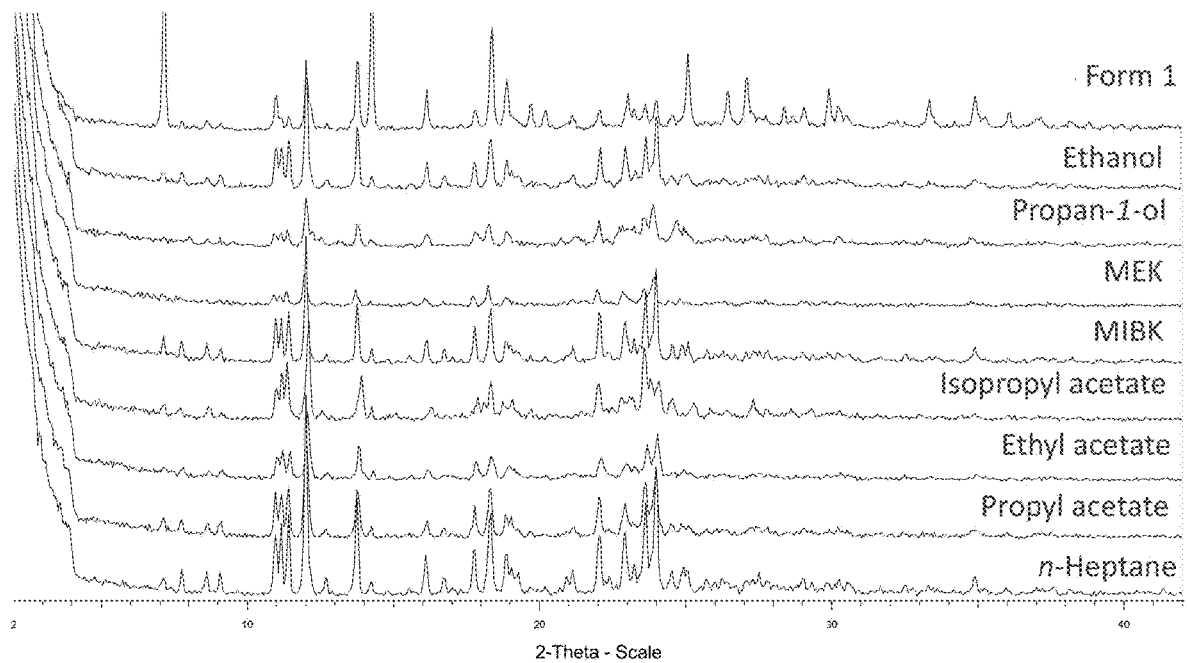
FIG. 14A: Overlay of XRPD patterns obtained from the polymorph screen on crystalline Sample 1, which are substantially consistent with Form 1.
Figure 14B:
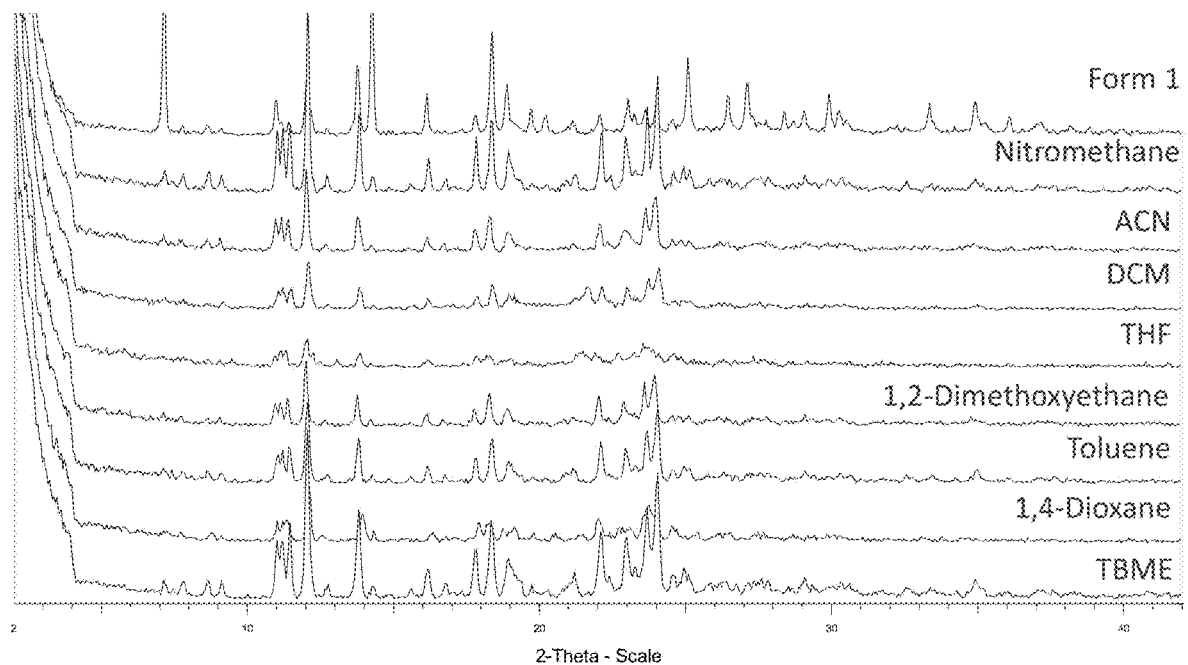
FIG. 14B: Overlay of XRPD patterns obtained from the polymorph screen on crystalline Sample 1, which are substantially consistent with Form 1.
Figure 14C:
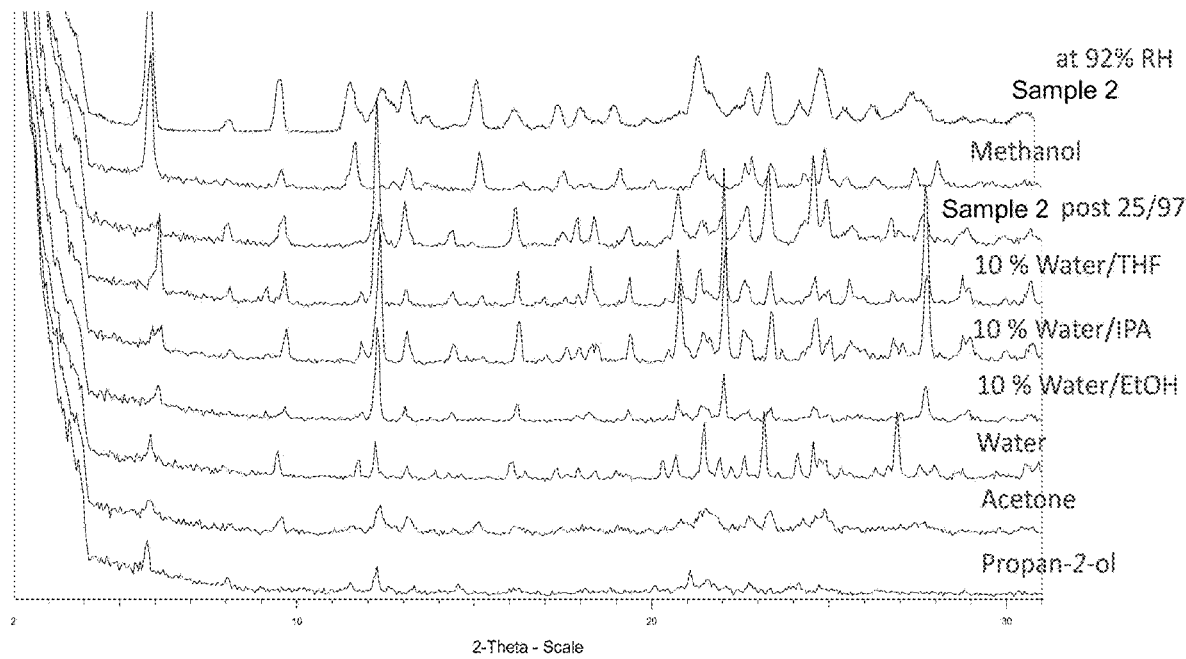
FIG. 14C: Overlay of XRPD patterns obtained from the polymorph screen on crystalline Sample 1, which are substantially consistent with Form 3.

The solubility assessment of the Sample 1 in different solvent systems showed that the compound had low solubility in alcohols, esters, and hydrocarbon solvents, but was highly soluble in water. XRPD analysis of solids recovered after maturation, cooling and evaporation (in the solvents listed in Table 13) found that either anhydrous Form 1 or hydrated Form 3 were produced (FIGS. 14A-14C). Consistent with the solid-state characterization of Sample 1 in Example 1, slurrying in water or water/solvent systems produced the hydrated state, Form 3. Pattern 3 was also observed from slurrying in 2-propanol, acetone and methanol, but it is likely that the hydrate resulted from residual water present in the solvent stock solutions (anhydrous solvents were not used in this screen).

Figure 10B:
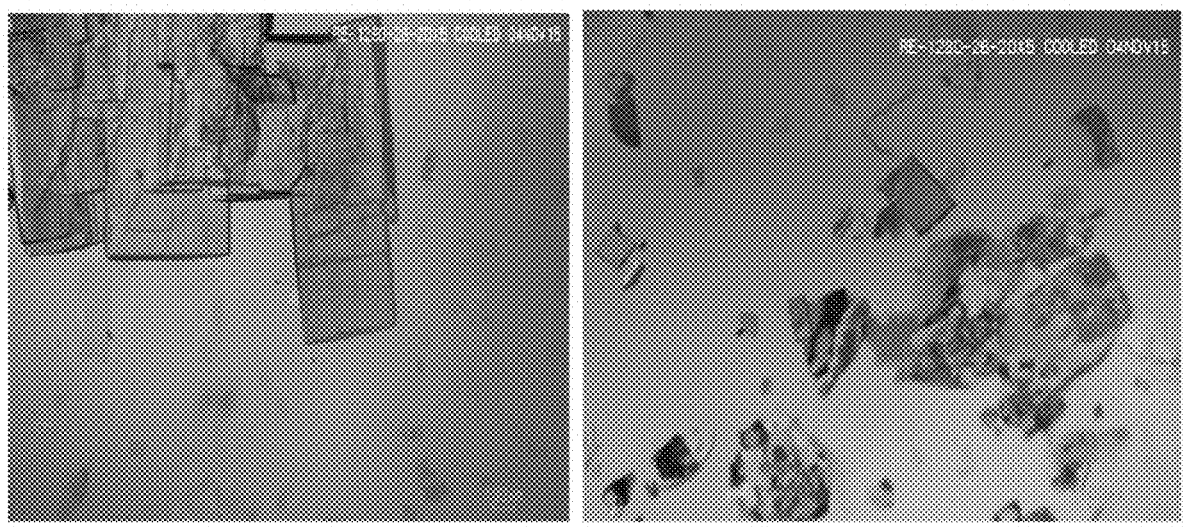
FIG. 10B: PLM images of crystals isolated from solubility assessment of Sample 1, produced platelet crystals upon cooling in methanol.
Figure 11:
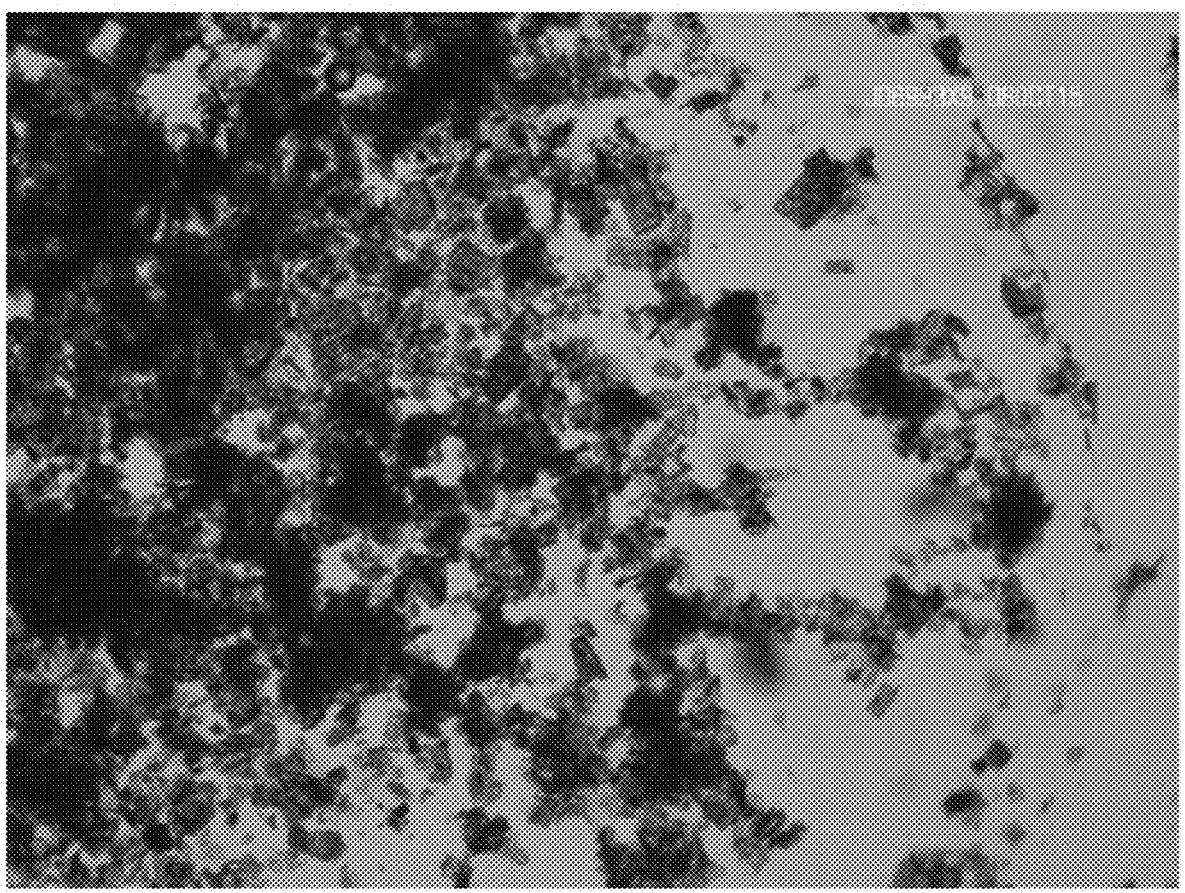
FIG. 11: PLM images of Sample 2.

During these screening experiments, it was observed that one sample (A20) produced crystals of plate morphology (see FIG. 10B), and was submitted for Single Crystal analysis. However, these crystals were found to exist as stacks (as seen by SEM, see FIGS. 12A-12C), not single crystals and were therefore unsuitable for collection by SCXRD. Analysis of the crystals by XRPD found that the material was consistent with a hydrated state, and most closely resembled Pattern 3 (FIG. 14C).

Example 3. Preparation and Characterization of Amorphous RAD1901-2HCl

A) Preparation and Characterization of Amorphous RAD1901-2HCl

Figure 15A:
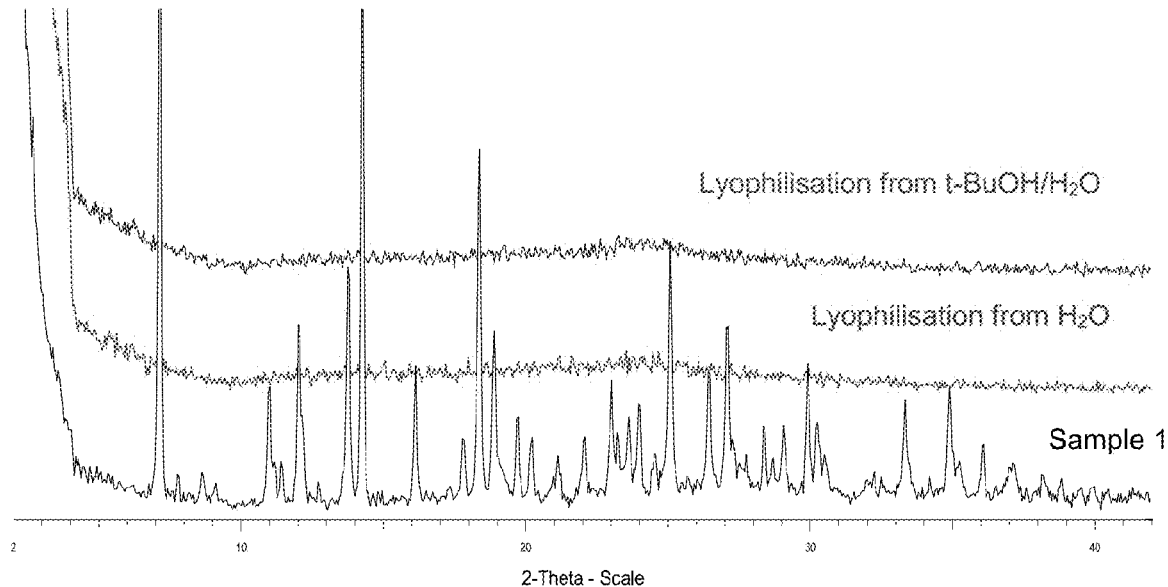
FIG. 15A: Overlay of XRPD patterns obtained for Sample 1 pre- and post-lyophilisation in water or t-butanol/water.

As Sample 1 of RAD1901-2HCl showed high solubility in water and t-butanol/water (1:1), amorphous RAD1901-2HCl was prepared from each of these solvents by lyophilization. RAD1901-2HCl (100 mg) was placed into a scintillation vial and appropriate solvent systems tested for dissolution of the material. Water or t-butanol/water (1:1) (20-30 vol., 2-3 mL) was added to the sample at RT, and the mixture was vortexed until dissolution, and filtered to remove any remaining solid particles. The solution was frozen in a dry ice/acetone bath and the solvent removed by lyophilization. The resulting solids were analyzed for amorphous content by XRPD (FIG. 15A), counterion identity by IC, purity by HPLC and NMR, and thermal properties by TGA and DSC (Table 14).

TABLE 14

Characterization data for amorphous RAD1901-2HCl produced by lyophilisation

Figure 15B:
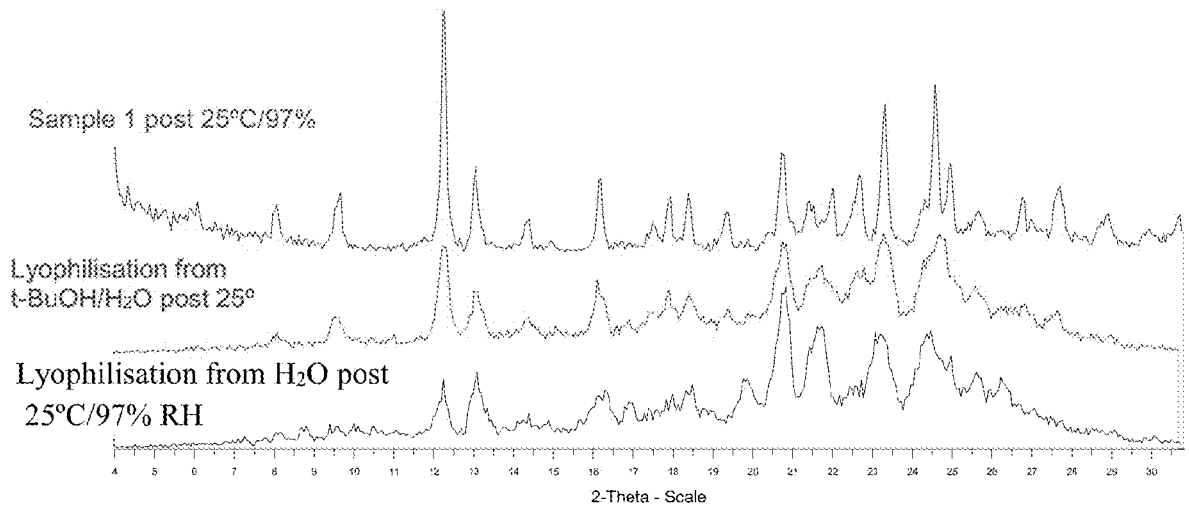
FIG. 15B: Overlay of XRPD patterns obtained for samples obtained by lyophilization if Sample 1 from water or t-butanol/water and crystalline samples of Sample 1 post-storage at 25° C./97% RH.
Figure 15C:
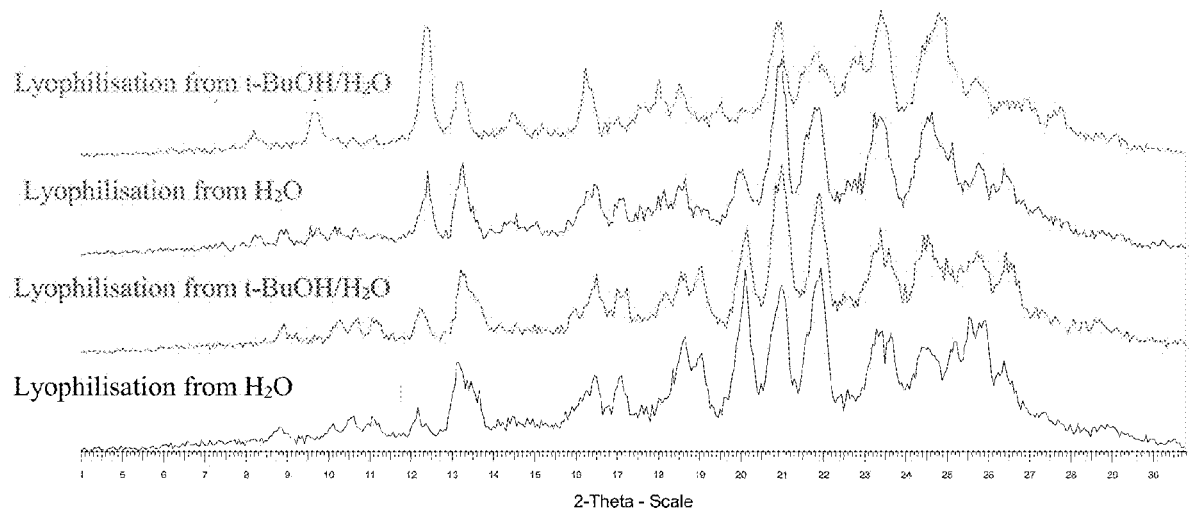
FIG. 15C: Overlay of XRPD patterns obtained for samples obtained by lyophilization from water or t-butanol/water of Sample 1 post-storage at 25° C./97% RH and 40° C./97% RH.
Figure 16:
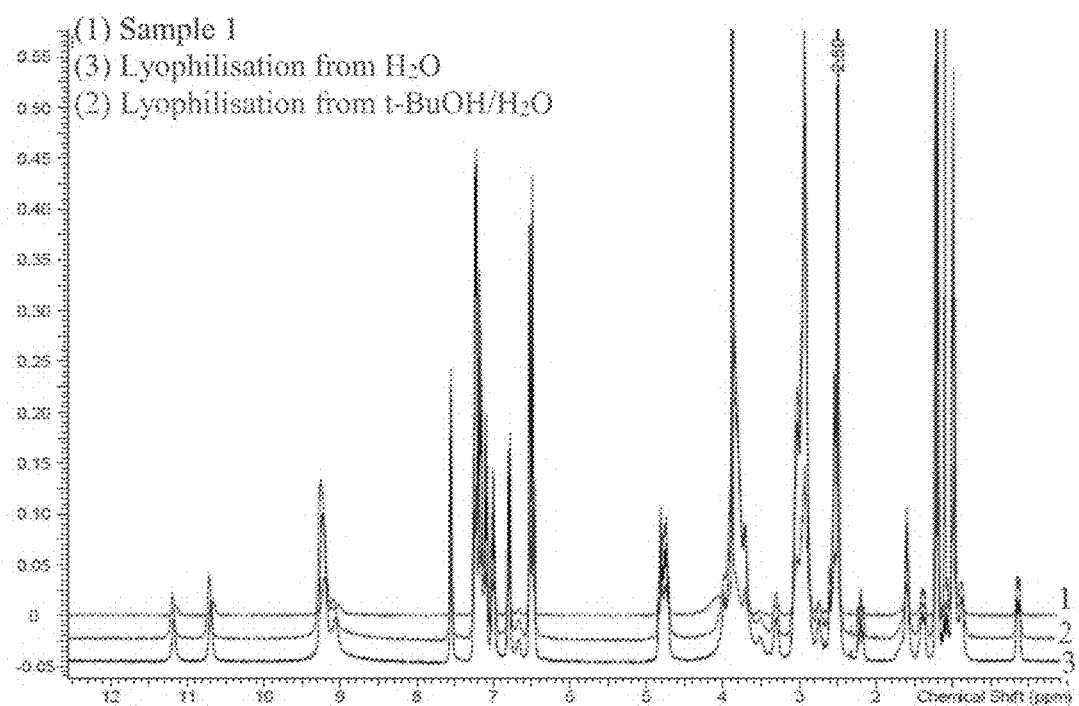
FIG. 16: $^1$H NMR spectra of Sample 1 pre- and post-lyophilisation in water or t-butanol/water.
Figure 17A:
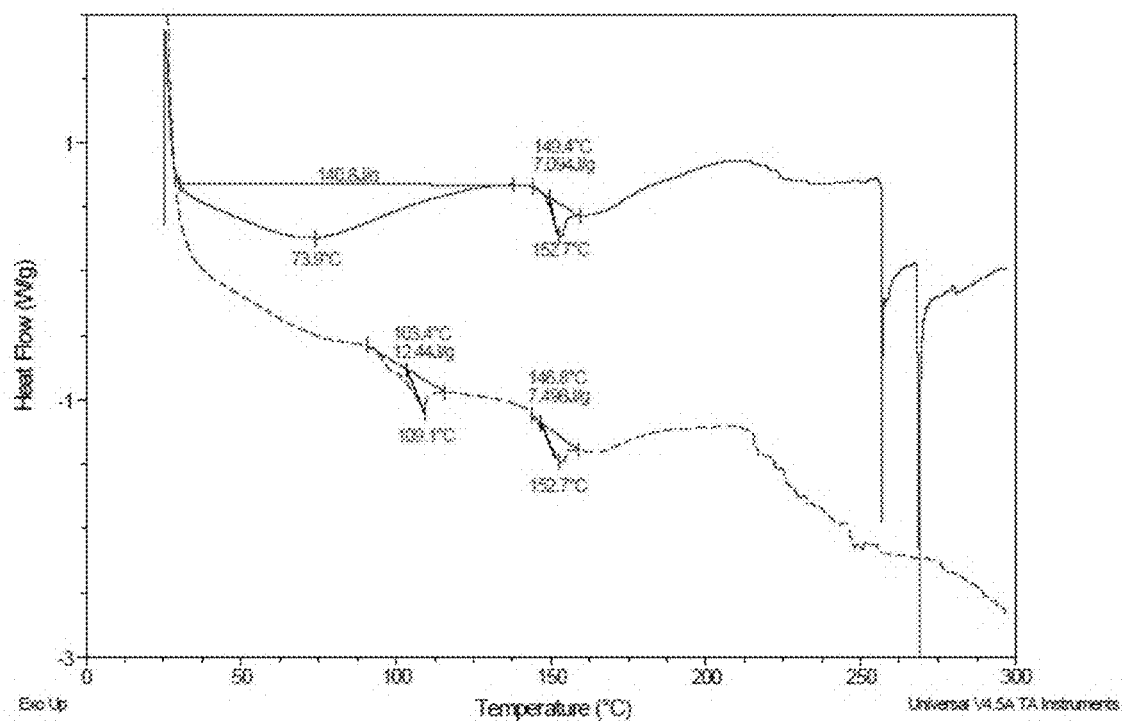
FIG. 17A: DSC analysis of samples of Sample 1 obtained by lyophilization from water (solid line) or t-butanol/water (dashed line).
Figure 17B:
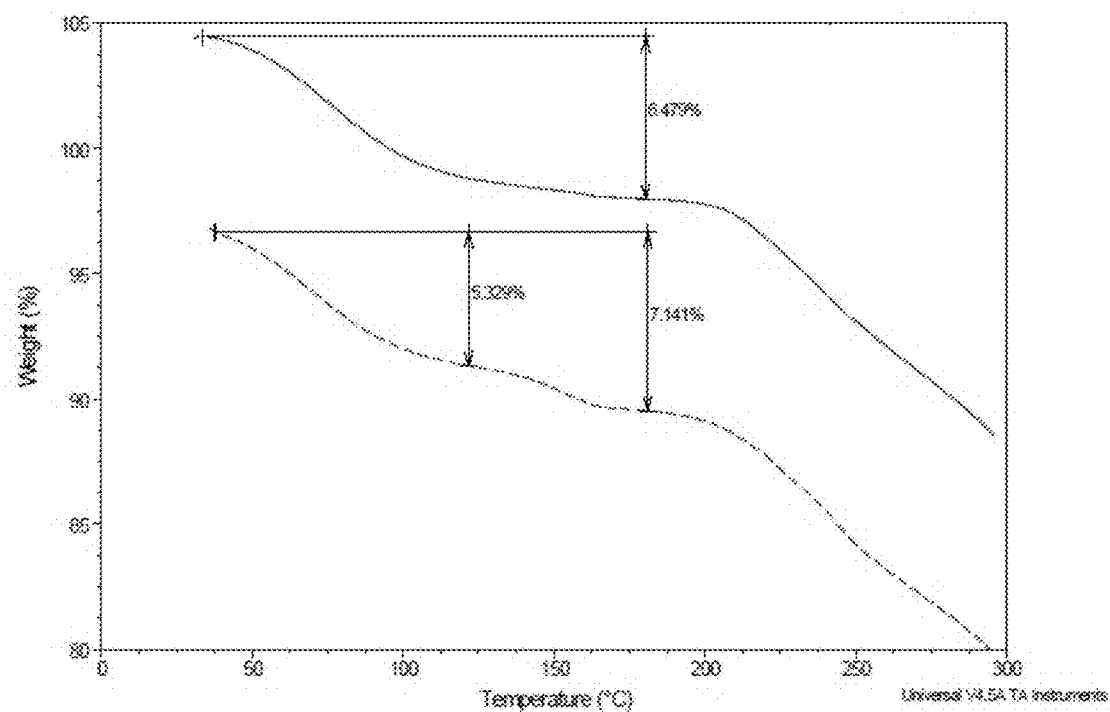
FIG. 17B: TGA analysis of samples of Sample 1 obtained by lyophilization from water (solid line) or t-butanol/water (dashed line).
Figure 17C:
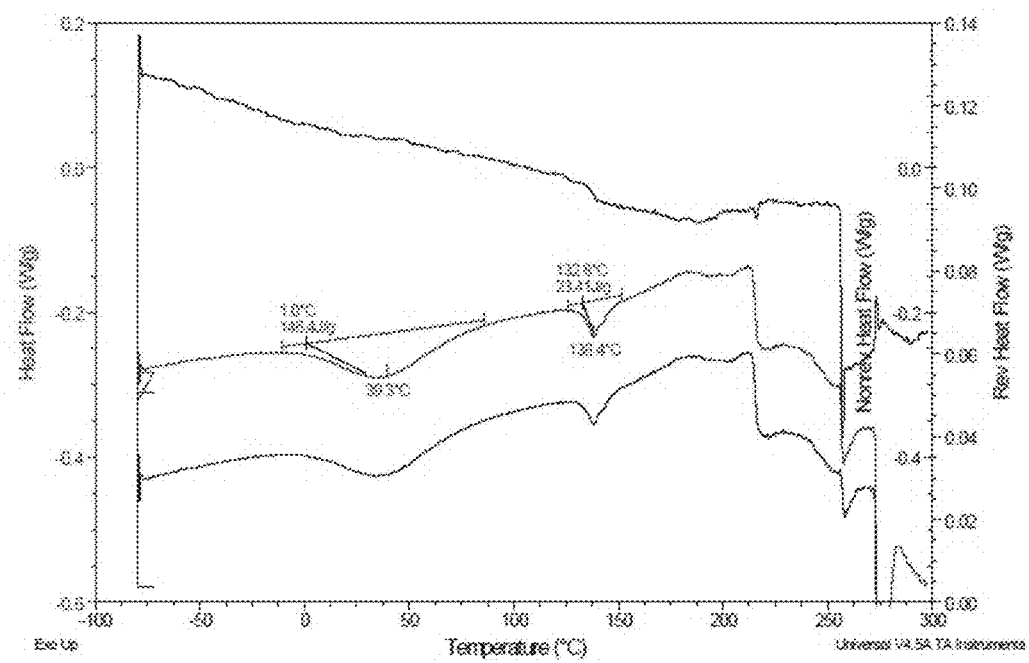
FIG. 17C: mDSC analysis of a sample of Sample 1 obtained by lyophilization from water (solid line).

| Technique/Sample ID | Lyophilization in water | Lyophilization in t-Butanol/Water(1:1) |
|---|---|---|
| XRPD | Amorphous (FIG. 15A) | Amorphous (FIG. 15A) |
| ¹H-NMR | Consistent with starting material (FIG. 16) | Consistent with starting material, 0.3 eq. residual t-butanol (FIG. 16) |
| HPLC (Purity %) | 99.3% AUC | 99.2% AUC |
| DSC | Broad endotherm from 25° C. to 140° C., endotherm at 149° C. (onset) (FIG. 17A) | Broad endotherm from 25° C. to 140° C., endotherms at 103° C. (onset) and 147° C. (onset) (FIG. 17A) |
| TGA | 6.5% wt. loss from RT to 190° C. (FIG. 17B) | Two steps: 5.3% wt. loss from RT to 120° C. and 1.8% wt. loss from 120° C. to 190° C. (FIG. 17B) |
| IC | Average = 1.79 (adjusted for TGA wt. loss = 1.93) | Average = 1.79 (adjusted for TGA wt. loss = 1.92) |
| mDSC | Broad endotherm 0-150° C. masks any Tg (FIG. 17C) | Broad endotherm 0-100° C. masks any Tg |
| XRPD post storage at 25° C./97% RH (10 days) | Consistent with Form 3 (FIG. 15B) | Consistent with Form 3 (FIG. 15B) |
| XRPD post storage at 40° C./75% RH (10 days) | Consistent with Form 3 (FIG. 15C) | Consistent with Form 3 (FIG. 15C) |

B) Scale-Up Preparation of Amorphous RAD1901-2HCl

In a scale-up preparation of amorphous RAD1901-2HCl, RAD1901-2HCl (600 mg) was dissolved in water (20 vol., 12 mL) and filtered to remove any remaining solid particles. The solution was then aliquoted into 24 HPLC vials, frozen in a dry ice/acetone bath and the solvent removed by lyophilisation. Solids produced by lyophilization were used directly in solubility assessment and polymorph screens in Example 4.

Example 4. Solubility Assessment and Polymorph Screen of Amorphous RAD1901-2HCl

A) Solubility Assessment and Polymorph Screen of Amorphous RAD1901-2HCl

Amorphous RAD1901-2HCl prepared as described in Example 3B was used directly in solubility assessment and polymorph screens (Table 15). XRPD patterns were further obtained for amorphous RAD1901-2HCl prepared using other solvents.

TABLE 15

Solubility assessment and polymorph screen on amorphous RAD1901-2HCl

| Sample ID | Solvent | 10 vol. | After maturation at 25° C. | PLM after maturation at 25° C. | XRPD post 25° C. | After maturation at 50 ° C. | XRPD post 50° C./RT | FIG. No. |
|---|---|---|---|---|---|---|---|---|
| B1. | n-Heptane | X | X | No visible crystalsX | N/A | X | Amorphous | 18D |
| B2. | Propyl acetate | X | X | No visible crystalsX | N/A | X | Form 2/3 | 18B |
| B3. | Ethyl acetate | X | X | No visible crystalsX | N/A | X | Form 2/3 | 18B |
| B4. | Isopropyl acetate | X | X | No visible crystalsX | N/A | X | Form 2/3 | 18B |
| B5. | MIBK | X | X | No visible crystalsX | N/A | X | Form 3 | 18B |
| B6 | 2-propanol | X | X | No visible crystalsX | N/A | X | Form 1⁺ | 18D |
| B7. | MEK | X | X | No visible crystalsX | N/A | X | Form 1⁺ | 18D |
| B8. | 1-propanol | X | X | No visible crystalsX | N/A | Crystalline material | Form 1 | 18A |
| B9. | Acetone | X | X | No visible crystalsX | N/A | X | Form 1* | 18D |
| B10. | Ethanol | X | X | No visible crystalsX | N/A | Fine crystals | Form 1 | 18A |
| B11. | Dimethyl sulfoxide | S | S | S | N/A | S | S | — |
| B12. | Water | S | X | Fine needles | Form 3 | Lath crystals | Form 3 | 18C |
| B13. | TBME | X | X | Birefringent solid | Amorphous | Some crystals | Poor crystalline | 18D |
| B14. | 1,4-Dioxane | X | X | No visible crystalsX | N/A | X | Poor crystalline | 18D |
| B15. | Toluene | X | X | No visible crystalsX | N/A | Fine crystals | Form 3 | 18B |
| B16. | 1,2-dimethoxyethane | X | X | No visible crystalsX | N/A | Crystalline material | Form 3* | 18C |
| B17. | Tetrahydrofuran | X | X | No visible crystalsX | N/A | Fine crystals | Form 1* | 18A (THF) |
| B18. | Dichloromethane | X | X | No visible crystalsX | N/A | Crystalline material | Form 3 | 18B |
| B19. | Methanol | X | Crystal | Cubic crystals | Form 3 | Green solution | N/A | 18C |
| B20. | Acetonitrile | X | X | No visible crystalsX | N/A | Crystalline material | Form 1 | 18A |
| B21. | Nitromethane | X | X | Cubic/needle crystals | Form 1 | Needle crystals | Form 1 | 18A |
| B22. | 10% water/EtOH | S | S | Needle/Lath crystals | Form 3 | Green solution | N/A | 18C |
| B23. | 10% water/IPA | X | X | Fine crystals | Form 3 | Fine crystals | Form 3 | 18C |
| B24. | 10% water/THF | X | X | Fine crystals | Form 3 | Fine crystals | Form 3 | 18C |

Legend: X = suspension; S = solution; +/− = nearly dissolved; *= poorly crystalline; N/A = not applicable; ⁺Possibly some Form 3 present In the polymorph screen of the amorphous RAD1901-2HCl prepared as described in Example 3B, an aliquot of each sample was examined for its morphology under the microscope, both after maturing at 25° C., and after maturing at 50° C./RT. If any crystalline material was observed at either maturation stage, the resulting solids were filtered, air dried and analyzed by high resolution XRPD. XRPD analysis of samples from the polymorph screen showed that only three distinct patterns could be observed: patterns for Forms 1, 2 and 3 previously observed (FIGS. 18A-18D). In some instances, the sample appeared to be a mixture of various polymorphic forms, e.g. Form 2 and Form 3 (FIGS. 18B-18C), similar to the mixture of Forms 2 and 3 in Sample 2 having an equilibrium between the two solid forms, depending on the prevailing RH.

Figure 18A:
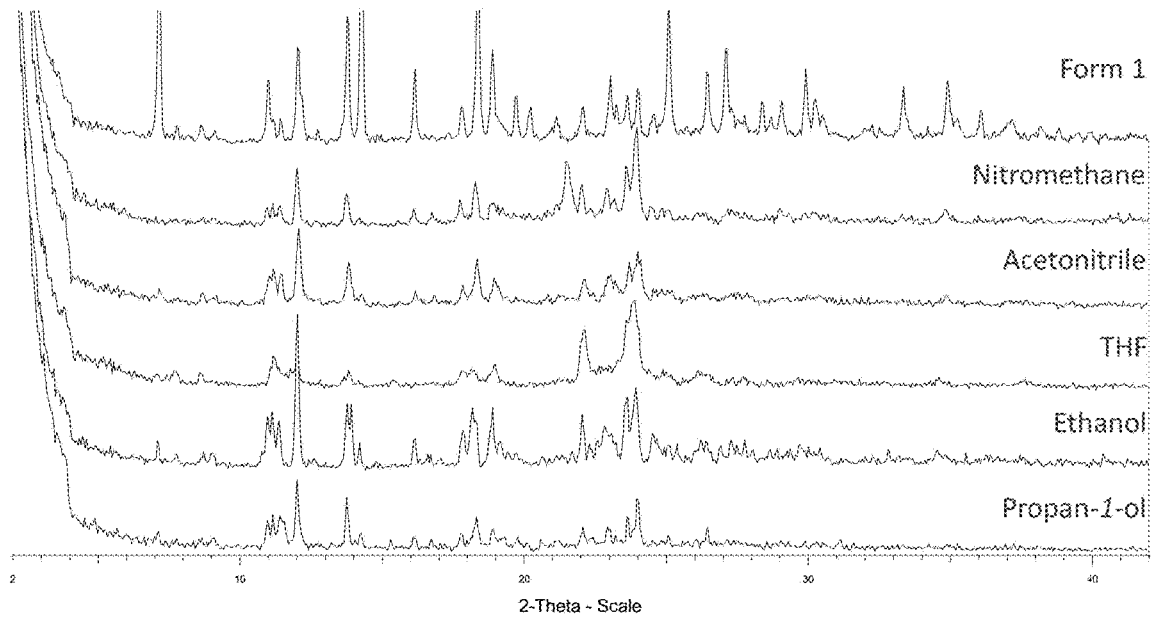
FIG. 18A: Overlay of XRPD patterns obtained from the polymorph screen on Sample 1 obtained by lyophilization from nitromethane, acetonitrile, THF, ethanol, or propan-1-ol, which are substantially consistent with (anhydrous) Form 1.
Figure 18B:
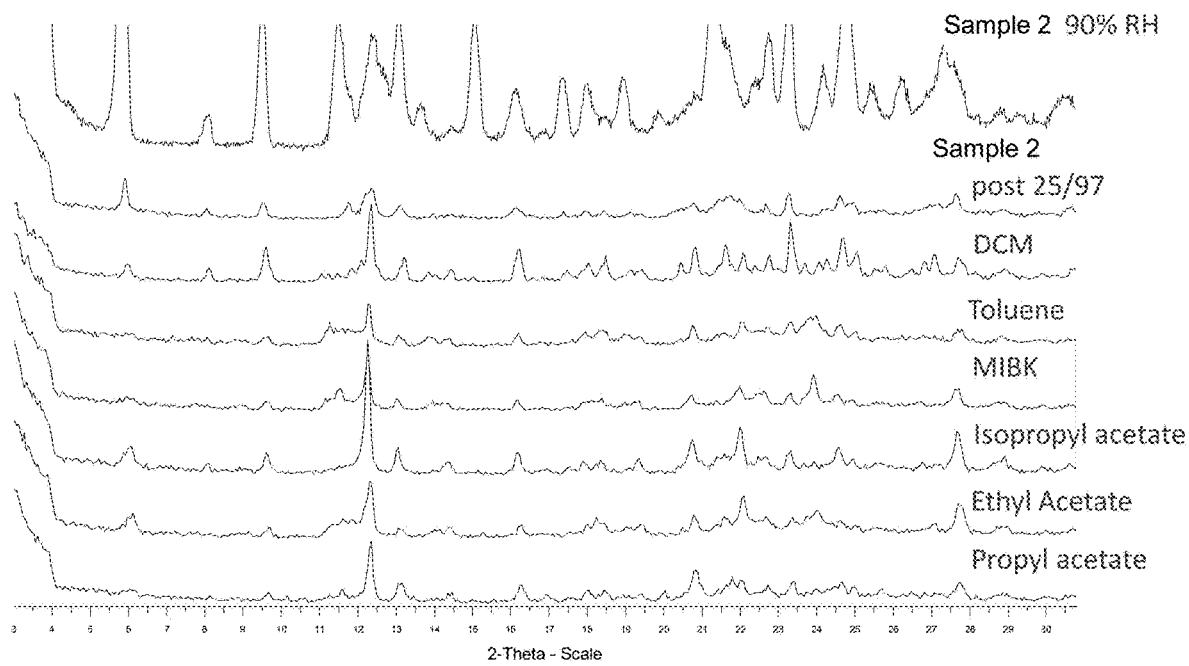
FIG. 18B: Overlay of XRPD patterns obtained from the polymorph screen on Sample 1 obtained by lyophilization from dichloromethane (DCM), toluene, methyl isobutyl ketone (MIBK), isopropyl acetate, ethyl acetate or propyl acetate, which are substantially consistent with Form 3 (Sample 2, 90% RH) or a mixture of Form 2 and Form 3 (sample 2 post 25/97).
Figure 18C:
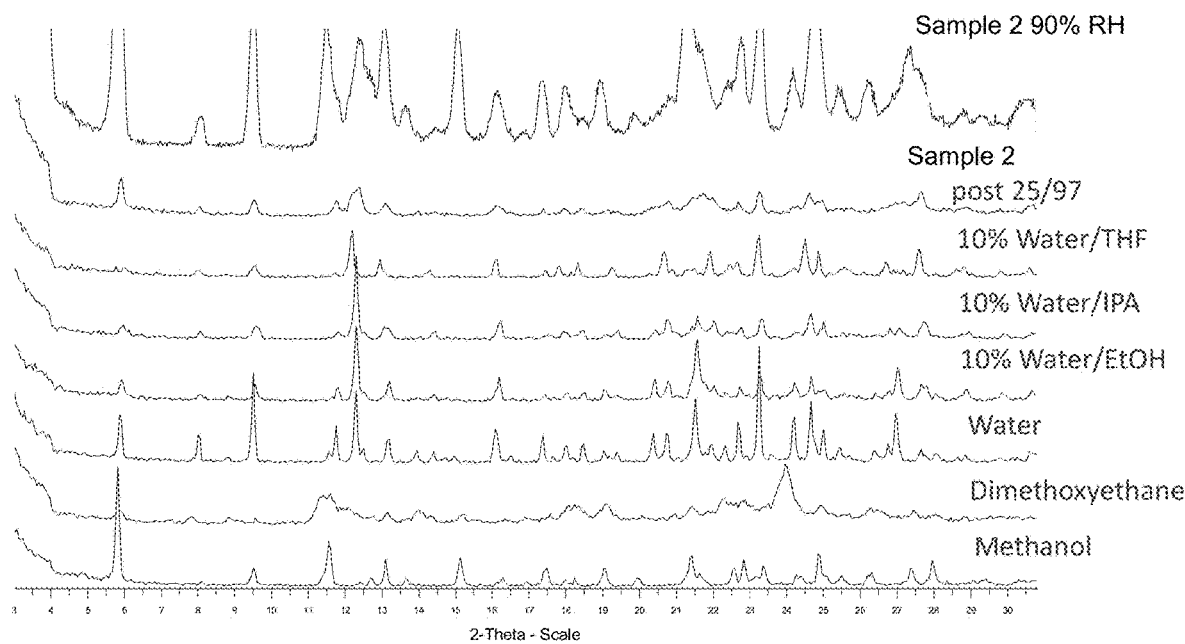
FIG. 18C: Overlay of XRPD patterns obtained from the polymorph screen on Sample 1 obtained by lyophilization from 10% water/THF, 10% water/IPA, 10% water/EtOH, water, dimethoxyethane, or methanol, which are substantially consistent with Form 3 (hydrate, Sample 2, 90% RH) or a mixture of Form 2 (anhydrous) and Form 3 (sample 2 post 25/97).
Figure 18D:
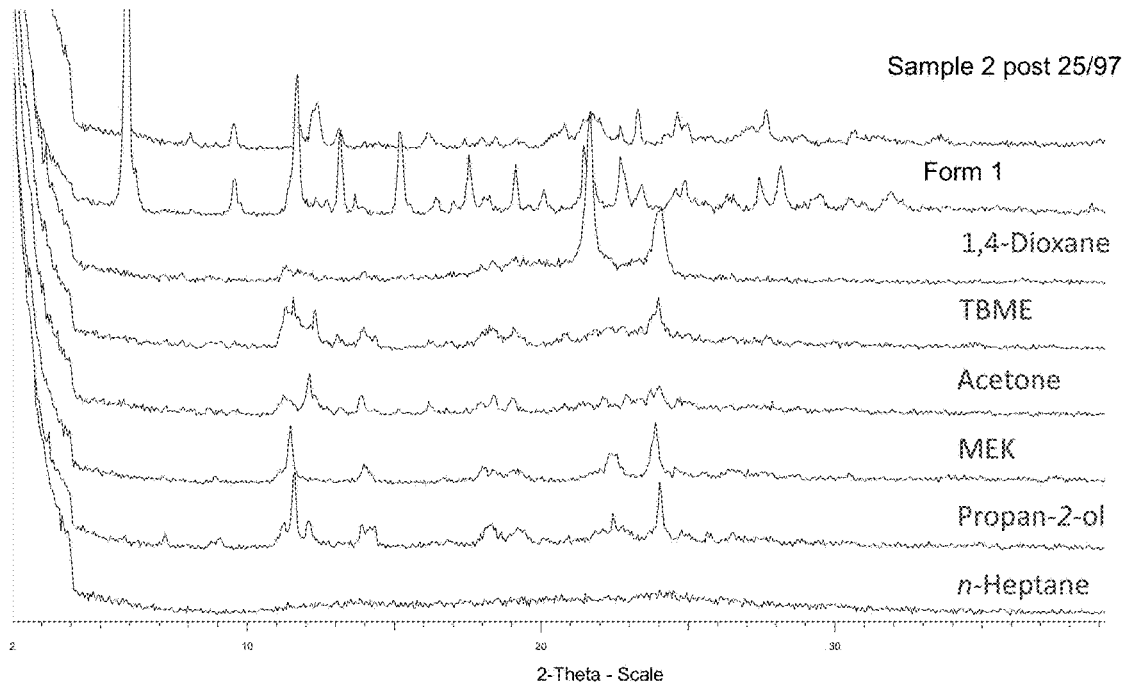
FIG. 18D: Overlay of XRPD patterns obtained from the polymorph screen on Sample 1 obtained by lyophilization from 1,4-dioxane, t-butyl methyl ether (TBME), acetone, methyl ethyl ketone (MEK), propan-2-ol, or n-heptane, which are too poorly crystalline to assign polymorph, but appear to be Form 1 or a mixture of Form 2 and Form 3 (sample 2 post 25/97).

Similarly, samples prepared from 2-propanol and MEK may contain a mix of anhydrous Form 1 and hydrated Form 3 material (FIG. 18D).

Figure 19A:
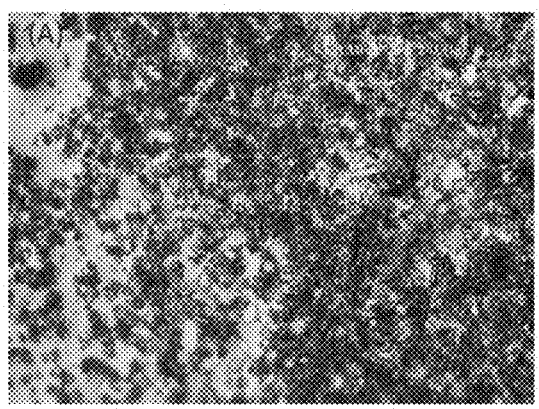
FIG. 19A: PLM images of crystals obtained during polymorph screens prepared by cooling a lyophilized sample of Sample 1-methanol.
Figure 19B:
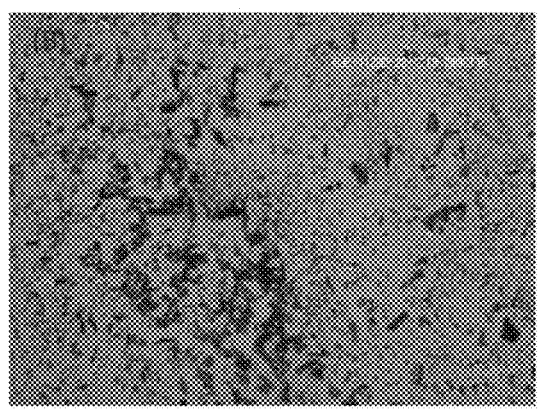
FIG. 19B: PLM images of crystals obtained during polymorph screens prepared by maturation of a lyophilized sample of Sample 1 in water.
Figure 19C:
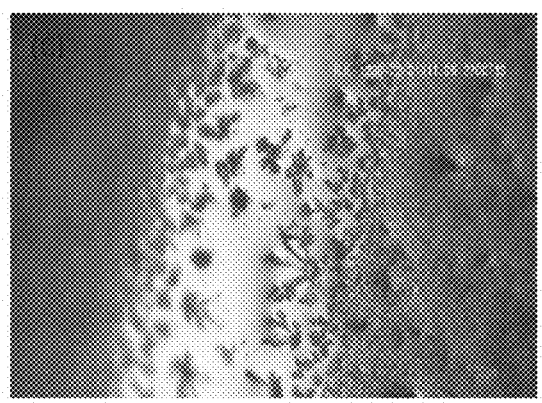
FIG. 19C: PLM images of crystals obtained during polymorph screens prepared by maturation of a lyophilized sample of Sample 1 in nitromethane.

PLM images were obtained for crystals obtained during polymorph screens using amorphous RAD1901-2HCl prepared as described in Example 3B via cooling in methanol (FIG. 19A), maturation in water (FIG. 19B), or maturation in nitromethane (FIG. 19C), respectively (FIG. 19).

Despite collecting high resolution XRPD data, some samples were also poorly crystalline and their pattern could not be definitively assigned, but closely resembles that of Form 1 (FIG. 18D). Therefore, no additional new patterns have been observed in these screens using amorphous RAD1901-2HCl.

B) Solubility Assessment of Amorphous RAD1901-2HCl in Water/Organic Solvent System Samples of amorphous RAD1901-2HCl were prepared in water/organic solvent mixtures containing varying ratios of water. The organic solvents chosen were anhydrous ethanol, methanol and ethyl acetate. The percentage of water in the water/organic solvent mixtures was varied between 0 and 10% (v/v) in order to place a limit on the level of water that can be present during production processes, and to retain formation of Form 1. Above this water activity limit, the hydrated Form 3 will be obtained, as shown by GVS experiments (see FIGS. 6G and 20A). It should be noted that samples prepared in ethyl acetate, were either slurried in anhydrous ethyl acetate, or in water saturated ethyl acetate.

Figure 20A:
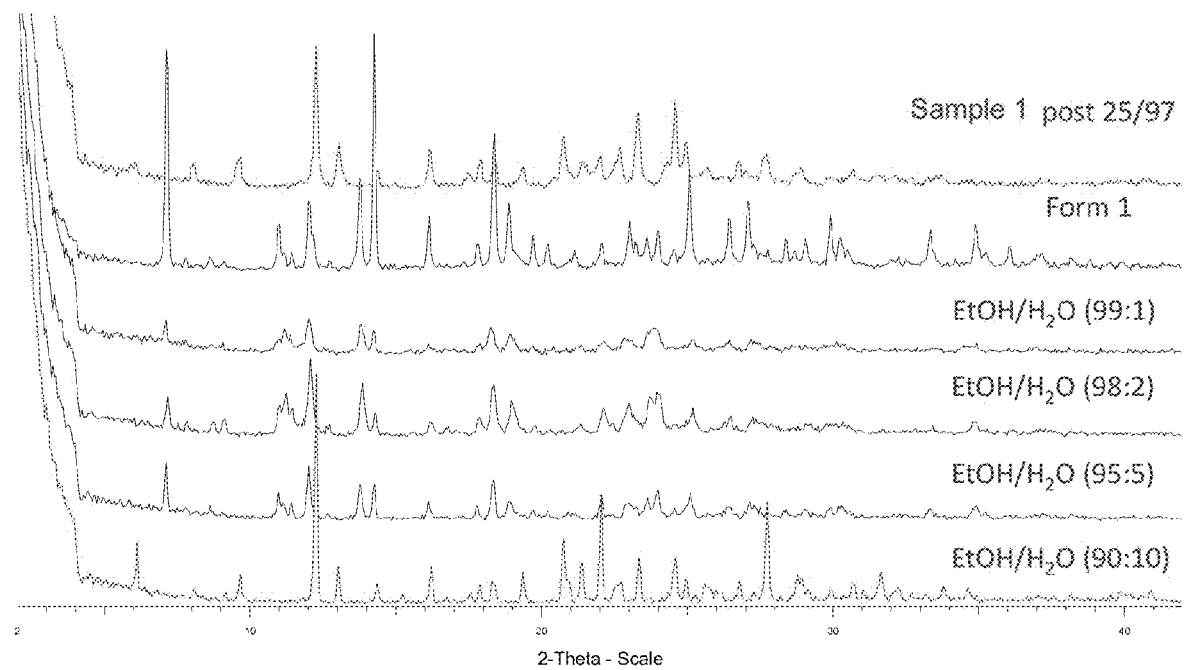
FIG. 20A: Overlay of XRPD patterns of samples prepared by maturation of a lyophilized sample of Sample 1 in different water/ethanol solvent mixtures, which are substantially consistent with Form 1 or Form 3 (hydrate) (sample 1 post 25/97).
Figure 20B:
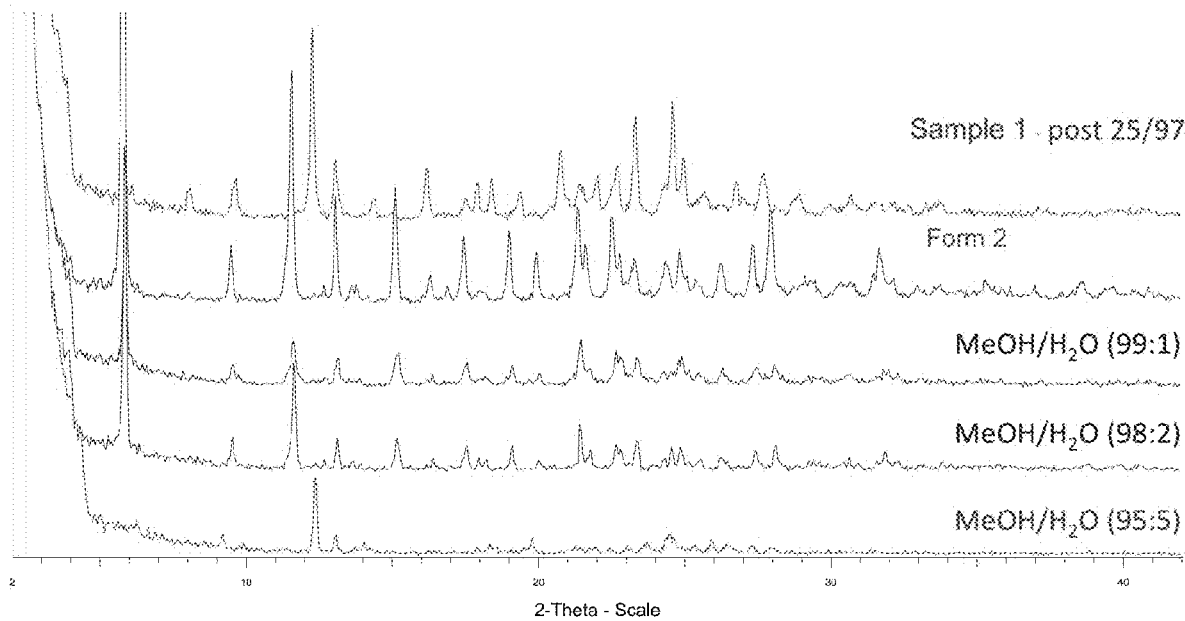
FIG. 20B: Overlay of XRPD patterns of samples prepared by maturation of a lyophilized sample of Sample 1 in different water/methanol solvent mixtures, which are substantially consistent with Form 2 or Form 3 (hydrate) (sample 1 post 25/97).
Figure 20C:
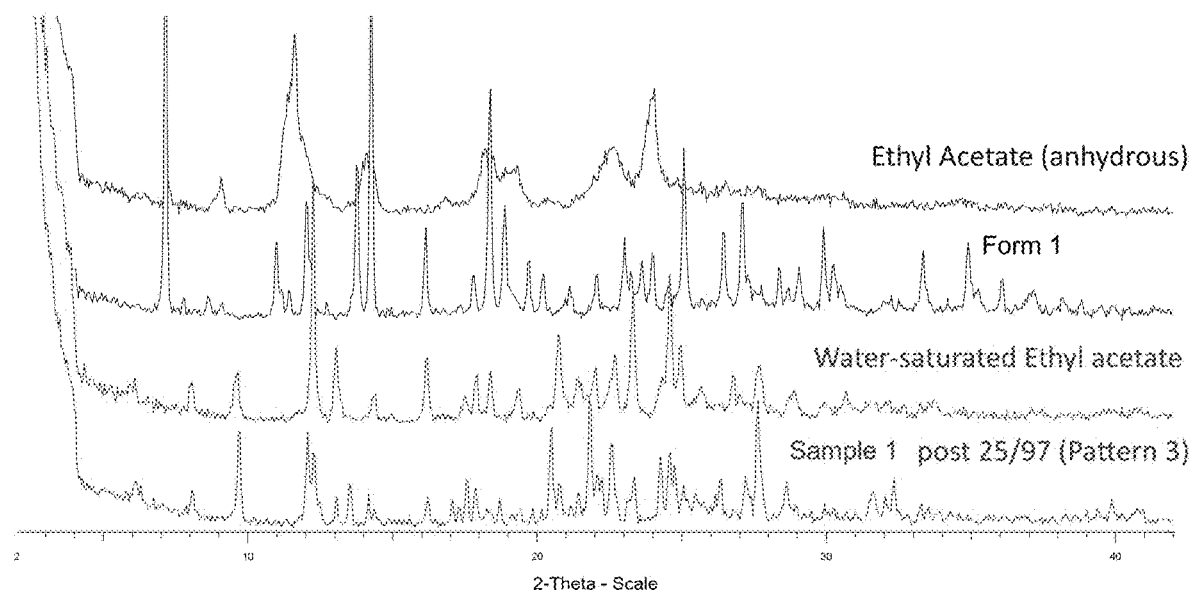
FIG. 20C: Overlay of XRPD patterns of samples prepared by maturation of a lyophilized sample of Sample 1 in anhydrous or water-saturated ethyl acetate, which are substantially consistent with Form 1 or Form 3 (sample 1 post 25/97).

The results from the water/organic solvent experiment are given in Table 16 and in FIGS. 20A-20C. The water activity values for each water/organic solvent mixture are provided in Table 16, and were calculated using the reference given in Bell, Halling, *Enzyme Microbiol. Technol.* 1997, 20, 471, incorporated herein by reference.

TABLE 16

Solubility assessment and polymorph screen on amorphous RAD1901-2HCl

| Sample ID | Solvent | Water activity | 10 vol. | 20 vol | 30 vol | After stirring at 25° C. for 72 hours | XRPD | FIG. No. |
|---|---|---|---|---|---|---|---|---|
| C1. | EtOH/H$_2$O (90:10) | 0.58 | S | | | X | Form 3 | 20A |
| C2. | EtOH/H$_2$O (95:5) | 0.39 | X | | | X | Form 1 | 20A |
| C3. | EtOH/H$_2$O (98:2) | 0.20 | X | | | X | Form 1 | 20A |
| C4. | EtOH/H$_2$O (99:1) | 0.11 | X | | | X | Form 1 | 20A |
| C5. | MeOH/H$_2$O (90:10) | 0.33 | S | | | S | S | |
| C6. | MeOH/H$_2$O (95:5) | 0.19 | S | | | Crystals | Form 3* | 20B |
| C7. | MeOH/H$_2$O (98:2) | 0.08 | +/− | | | Crystals | Form 2 | 20B |
| C8. | MeOH/H$_2$O (99:1) | 0.04 | +/− | | | Crystals | Form 2 | 20B |
| C9. | Ethyl acetate (anhydrous) | 0.00 | X | X | X | X | Form 1* | 20C |
| C10. | Water-saturated ethyl acetate | 0.77 | X | X | X | X | Form 3 | 20C |

Legend: X = suspension; S = solution; +/− = nearly dissolved; *= poorly crystalline.

The water/organic solvent experiments demonstrate a water activity limit above which the hydrated Form 3 was produced. Samples of amorphous RAD1901-2HCl obtained from Example 3b prepared in anhydrous ethanol crystallized as Form 1 material, consistent with the XRPD pattern obtained during polymorph screening of amorphous Sample 1 (see Table 15). It is also known that ethanol solvent is used in the production of Form 1 material of RAD1901-2HCl (Sample 1) during drug purification processes (along with ethyl acetate). Crystals produced from water/ethanol were Form 1 up to a ratio of 5% water/ethanol, above which the hydrate Form 3 resulted. This equates to a water activity limit of 0.39 (see Table 16), and indicates that at least on small-scale, up to 5% water can be present during drug production process to produce Form 1.

Amorphous RAD1901-2HCl in anhydrous methanol crystallized as Form 2 having XRPD Pattern 2. This is consistent with the supplied batch of sample 2, which was known to form during isolation of RAD1901-2HCl using methanol (and ethyl acetate) solvent. Crystals produced from water/methanol were Form 2 (anhydrous) up to a ratio of 2% water/methanol, above which the hydrate Form 3 having XRPD Pattern 3 was produced. This equates to a water activity limit of 0.08 (see Table 16), which is low, and may reflect the observations (by GVS, see FIG. 7A) that at relatively low (ambient) RH, Form 2 material converts to the hydrate Form 3 or a mixture of Forms 2 and 3.

Slurrying of amorphous RAD1901-2HCl in anhydrous ethyl acetate produced crystals of Form 1 material, which supports the observation that Form 1 could be isolated using ethanol and ethyl acetate solvents in drug production processes, whereas Form 2 could be produced using methanol and ethyl acetate. The ratio of water/ethyl acetate was not varied, since the water-saturated ethyl acetate has above 2.7% (v/v) water (e.g., 3.3% water at 20° C.), which equates to water activity of 0.77. Slurrying in water-saturated ethyl acetate produced the hydrate Form 3.

Example 5. A crystalline form of RAD1901-2HCl.

Example 6. A solid form of RAD1901-2HCl, having an X-ray powder diffraction pattern comprising a peak, in terms of 2-theta, at 7.1 degrees 2θ±0.2 degree 2θ at about relative humidity 0%.

Example 7. A solid form of RAD1901-2HCl, having an X-ray powder diffraction pattern comprising a peak, in terms of 2-theta, at 7.1 degrees 2θ±0.2 degree 2θ and/or 14.3 degrees 2θ±0.2 degree 2θ at about relative humidity 0%.

Example 8. A solid form of RAD1901-2HCl, having an X-ray powder diffraction pattern comprising at least two peaks, in terms of 2-theta, selected from the group consisting of 7.1 degrees 2θ±0.2 degree 2θ, 14.3 degrees 2θ±0.2 degree 2θ and 18.3 degrees 2θ±0.2 degree 2θ at about relative humidity 0%.

Example 9. A solid form of RAD1901-2HCl, having an X-ray powder diffraction pattern comprising at least three peaks, in terms of 2-theta, selected from the group consisting of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ and 12.0 degrees 2θ±0.2 degree 2θ, at about relative humidity 0%.

Example 10. A solid form of RAD1901-2HCl, having an X-ray powder diffraction pattern comprising at least four peaks, in terms of 2-theta, selected from the group consisting of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ, 12.0 degrees 2θ±0.2 degree 2θ, 25.1 degrees 2θ±0.2 degree 2θ and 18.9 degrees 2θ±0.2 degree 2θ, at about relative humidity 0%.

Example 11. A solid form of RAD1901-2HCl, having an X-ray powder diffraction pattern comprising at least five peaks, in terms of 2-theta, selected from the group consisting of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ, 12.0 degrees 2θ±0.2 degree 2θ, 25.1 degrees 2θ±0.2 degree 2θ, 18.9 degrees 2θ±0.2 degree 2θ, 27.2 degrees 2θ±0.2 degree 2θ and 11.0 degrees 2θ±0.2 degree 2θ, at about relative humidity 0%.

Example 12. A solid form of RAD1901-2HCl, having an X-ray powder diffraction pattern comprising at least five peaks, in terms of 2-theta, selected from the group consisting of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ, 12.0 degrees 2θ±0.2 degree 2θ, 25.1 degrees 2θ±0.2 degree 2θ, 18.9 degrees 2θ±0.2 degree 2θ, 27.2 degrees 2θ±0.2 degree 2θ, 11.0 degrees 2θ±0.2 degree 2θ and 16.2 degrees 2θ±0.2 degree 2θ, at about relative humidity 0%.

Example 13. A solid form of RAD1901-2HCl, having an X-ray powder diffraction pattern comprising at least seven peaks, in terms of 2-theta, selected from the group consisting of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ, 12.0 degrees 2θ±0.2 degree 2θ, 25.1 degrees 2θ±0.2 degree 2θ, 18.9 degrees 2θ±0.2 degree 2θ, 27.2 degrees 2θ±0.2 degree 2θ, 11.0 degrees 2θ±0.2 degree 2θ and 16.2 degrees 2θ±0.2 degree 2θ, at about relative humidity 0%.

Example 14. A solid form of RAD1901-2HCl, having an X-ray powder diffraction pattern comprising at least eight peaks, in terms of 2-theta, selected from the group consisting of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ, 12.0 degrees 2θ±0.2 degree 2θ, 25.1 degrees 2θ±0.2 degree 2θ, 18.9 degrees 2θ±0.2 degree 2θ, 27.2 degrees 2θ±0.2 degree 2θ, 11.0 degrees 2θ±0.2 degree 2θ and 16.2 degrees 2θ±0.2 degree 2θ, at about relative humidity 0%.

Example 15. A solid form of RAD1901-2HCl, having an X-ray powder diffraction pattern comprising at least nine peaks, in terms of 2-theta, selected from the group consisting of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ, 12.0 degrees 2θ±0.2 degree 2θ, 25.1 degrees 2θ±0.2 degree 2θ, 18.9 degrees 2θ±0.2 degree 2θ, 27.2 degrees 2θ±0.2 degree 2θ, 11.0 degrees 2θ±0.2 degree 2θ and 16.2 degrees 2θ±0.2 degree 2θ, at about relative humidity 0%.

Example 16. A solid form of RAD1901-2HCl, having an X-ray powder diffraction pattern comprising the peaks, in terms of 2-theta, of 7.1 degrees 2θ±0.2 degree 2θ, 14.3 degrees 2θ±0.2 degree 2θ, 18.3 degrees 2θ±0.2 degree 2θ, 13.8 degrees 2θ±0.2 degree 2θ, 12.0 degrees 2θ±0.2 degree 2θ, 25.1 degrees 2θ±0.2 degree 2θ, 18.9 degrees 2θ±0.2 degree 2θ, 27.2 degrees 2θ±0.2 degree 2θ, 11.0 degrees 2θ±0.2 degree 2θ and 16.2 degrees 2θ±0.2 degree 2θ, at about relative humidity 0%.

Example 17. A solid form of RAD1901-2HCl, having an X-ray powder diffraction pattern substantially as shown in FIG. 4G at about relative humidity 0%.

Example 18. A solid form of RAD1901-2HCl, having a differential scanning calorimetry (DSC) thermogram comprising a melting onset at 218.2° C. and an endothermic peak at 232.1° C.

Example 19. The solid form of Example 18, having a differential scanning calorimetry (DSC) thermogram substantially as shown in the bottom figure of FIG. 8.

Example 20. A solid form of RAD1901-2HCl, having a thermogravimetric analysis (TGA) substantially as shown in the top graph of FIG. 8.

Example 21. A composition comprising RAD1901 wherein at least 5% w/w of the total amount of RAD1901 is a solid form of any one of previous examples.

Example 22. A composition comprising RAD1901 wherein at least 25% w/w of the total amount of RAD1901 is a solid form of any one of previous examples.

Example 23. A composition comprising RAD1901 wherein at least 50% w/w of the total amount of RAD1901 is a solid form of any one of previous examples.

Example 24. A composition comprising RAD1901 wherein at least 90% w/w of the total amount of RAD1901 is a solid form of any one of previous examples.

Example 25. A composition comprising RAD1901 wherein at least 95% w/w of the total amount of RAD1901 is a solid form of any one of previous examples.

Example 26. A composition comprising RAD1901 wherein at least 98% w/w of the total amount of RAD1901 is a solid form of any one of previous examples.

Example 27. A pharmaceutical composition comprising the solid form of any of Examples 5-26 and one or more pharmaceutically acceptable excipients.

Example 28. A process for preparing a solid form of any of Examples 5-27 comprising precipitating from a solution comprising RAD1901-2HCl and a solvent, or slurrying RAD1901-2HCl in a solvent, wherein the solvent comprises an organic solvent substantially free of methanol, and the content of water is at or below 5% v/v.

Example 29. The process according to Example 28 wherein the solvent is selected from the group consisting of n-heptane, propyl acetate, ethyl acetate, isopropyl acetate, methyl isobutyl ketone (MIBK), methyl ethyl ketone (MEK), 1-propanol, ethanol, t-butyl methyl ether (TBME), 1,4-dioxane, toluene, 1,2-dimethoxyethane, tetrahydrofuran, dichloromethane, acetonitrile, nitromethane, and mixtures thereof.

Example 30. A method of treating breast cancer comprising an administration to a subject in need thereof a solid form of any of Examples 5-26.

Example 31. The method of Example 30 wherein said breast cancer is ER+.

Example 32. A method of treating ovarian cancer comprising an administration to a subject in need thereof a solid form of RAD1901-2HCl according to any of Examples 5-26.

Example 33. A solid form of RAD1901-2HCl, having an X-ray powder diffraction pattern comprising a peak, in terms of 2-theta, at 6.3 degrees 2θ±0.2 degree 2θ at about relative humidity 0%.

Example 34. A solid form of RAD1901-2HCl, having an X-ray powder diffraction pattern comprising a peak, in terms of 2-theta, at 6.3 degrees 2θ±0.2 degree 2θ and/or 12.5 degrees 2θ±0.2 degree 2θ at about relative humidity 0%.

Example 35. A solid form of RAD1901-2HCl, having an X-ray powder diffraction pattern comprising at least two peaks, in terms of 2-theta, selected from the group consisting of 6.3 degrees 2θ±0.2 degree 2θ, 12.5 degrees 2θ±0.2 degree 2θ and 15.4 degrees 2θ±0.2 degree 2θ, at about relative humidity 0%.

Example 36. A solid form of RAD1901-2HCl, having an X-ray powder diffraction pattern comprising at least three peaks, in terms of 2-theta, selected from the group consisting of 6.3 degrees 2θ±0.2 degree 2θ, 12.5 degrees 2θ±0.2 degree 2θ, 15.4 degrees 2θ±0.2 degree 2θ, 18.3 degrees 2θ±0.2 degree 2θ and 13.4 degrees 2θ±0.2 degree 2θ, at about relative humidity 0%.

Example 37. A solid form of RAD1901-2HCl having an X-ray powder diffraction pattern substantially as shown in FIG. 5H at about relative humidity 0%.

Example 38. A pharmaceutical composition comprising a solid form according to any one of Examples 32-37 and one or more pharmaceutically acceptable excipients.

Example 39. A solid form of RAD1901-2HCl that is a hydrate.

Example 40. The solid form of RAD1901-2HCl of Example 39 that is a dihydrate.

Example 41. The solid form of Examples 39 or 40 having an X-ray powder diffraction pattern comprising a peak, in terms of 2-theta, at 5.8 degrees 2θ±0.2 degree 2θ at about relative humidity 92%.

Example 42. The solid form of any of Examples 39-41 having an X-ray powder diffraction pattern comprising a peak, in terms of 2-theta, at 5.8 degrees 2θ±0.2 degree 2θ and/or 21.3 degrees 2θ±0.2 degree 2θ, at about relative humidity 92%.

Example 43. The solid form of any of Examples 39-41 having an X-ray powder diffraction pattern comprising at least two peaks, in terms of 2-theta, selected from the group consisting of 5.8 degrees 2θ±0.2 degree 2θ, 21.3 degrees 2θ±0.2 degree 2θ and 24.8 degrees 2θ±0.2 degree 2θ, at about relative humidity 92%.

Example 44. The solid form of any of Examples 39-41 having an X-ray powder diffraction pattern comprising at least three peaks, in terms of 2-theta, selected from the group consisting of 5.8 degrees 2θ±0.2 degree 2θ, 21.3 degrees 2θ±0.2 degree 2θ, 24.8 degrees 2θ±0.2 degree 2θ, 23.3 degrees 2θ±0.2 degree 2θ and 9.5 degrees 2θ±0.2 degree 2θ, at about relative humidity 92%.

Example 45. The solid form of any of Examples 39-41 having an X-ray diffraction pattern comprising at least four peaks, in terms of 2-theta, selected from the group consisting of 5.8 degrees 2θ±0.2 degree 2θ, 21.3 degrees 2θ±0.2 degree 2θ, 24.8 degrees 2θ±0.2 degree 2θ, 23.3 degrees 2θ±0.2 degree 2θ, 12.1 degrees 2θ±0.2 degree 2θ and 9.5 degrees 2θ±0.2 degree 2θ, at about relative humidity 92%.

Example 46. A solid form of RAD1901-2HCl that is amorphous.

Example 47. A form of RAD1901-2HCl as an amorphous material in a dispersion matrix.

Example 48. A tablet comprising 400 mg amorphous RAD1901-2HCl dispersed into a matrix.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A solid form of RAD1901-2HCl,

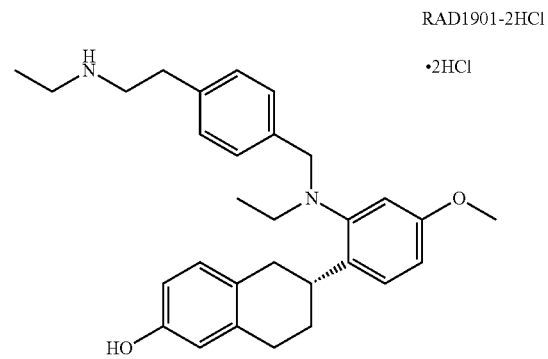 [SMILES: CCNCCc1ccc(CN(CC)c2cc(OC)ccc2[C@@H]2CCc3cc(O)ccc3C2)cc1]

wherein the solid form of RAD1901-HCl is a mixture of solid Form 2 and solid Form 3 of RAD1901-2HCl, and is characterized by an X-Ray powder diffraction pattern comprising peaks, in terms of 2-theta, at 6.3 degrees 2θ±0.2 degree 2θ and 12.5 degrees 2θ±0.2 degree 2θ at relative humidity 0%, and further characterized by an X-Ray powder diffraction pattern comprising peaks, in terms of 2-theta, at 5.8 degrees 2θ±0.2 degree 2θ, 21.3 degrees 2θ±0.2 degree 2θ and 24.8 degrees 2θ±0.2 degree 2θ, at about relative humidity 92%.

2. The solid form of RAD1901-2HCl according to claim 1, wherein the solid form is characterized by an X-ray powder diffraction pattern comprising peaks, in terms of 2-theta, at 6.3 degrees 2θ±0.2 degree 2θ, 12.5 degrees 2θ±0.2 degree 2θ, and 15.4 degrees 2θ±0.2 degree 2θ, at relative humidity 0%, and further characterized by an X-Ray powder diffraction pattern comprising peaks, in terms of 2-theta, at 5.8 degrees 2θ±0.2 degree 2θ, 21.3 degrees 2θ±0.2 degree 2θ, 23.3 degrees 2θ±0.2 degree 2θ, and 24.8 degrees 2θ±0.2 degree 2θ, at about relative humidity 92%.

3. The solid form of RAD1901-2HCl according to claim 2, wherein the solid form is characterized by an X-ray powder diffraction pattern comprising peaks, in terms of 2-theta, at 6.3 degrees 2θ±0.2 degree 2θ, 12.5 degrees 2θ±0.2 degree 2θ, 13.4 degrees 2θ±0.2 degree 2θ, and 15.4 degrees 2θ±0.2 degree 2θ, at relative humidity 0%, and further characterized by an X-Ray powder diffraction pattern comprising a peak, in terms of 2-theta, at 5.8 degrees 2θ±0.2 degree 2θ, 12.1 degrees 2θ±0.2 degree 2θ, 21.3 degrees 2θ±0.2 degree 2θ, 23.3 degrees 2θ±0.2 degree 2θ, and 24.8 degrees 2θ±0.2 degree 2θ, at about relative humidity 92%.

4. The solid form of RAD1901-2HCl according to claim 3, wherein the solid form is characterized by an X-ray powder diffraction pattern comprising peaks, in terms of 2-theta, at 6.3 degrees 2θ±0.2 degree 2θ, 12.5 degrees 2θ±0.2 degree 2θ, 13.4 degrees 2θ±0.2 degree 2θ, 15.4 degrees 2θ±0.2 degree 2θ, and 18.3 degrees 2θ±0.2 degree 2θ, at relative humidity 0%, and further characterized by an X-Ray powder diffraction pattern comprising a peak, in terms of 2-theta, at 5.8 degrees 2θ±0.2 degree 2θ, 9.5 degrees 2θ±0.2 degree 2θ, 12.1 degrees 2θ±0.2 degree 2θ, 21.3 degrees 2θ±0.2 degree 2θ, 23.3 degrees 2θ±0.2 degree 2θ, and 24.8 degrees 2θ±0.2 degree 2θ, at about relative humidity 92%.

5. The solid form of RAD1901-2HCl according to claim 1, having a dynamic vapor sorption (DVS) isotherm plot collected from 0 to 90% relative humidity, as shown in FIG. 6A.

6. The solid form of RAD1901-2HCl according to claim 1, having a dynamic vapor sorption (DVS) kinetic plot collected from 0 to 90% relative humidity, as shown in FIG. 6B.

7. A pharmaceutical composition comprising the solid form of RAD1901-2HCl according to claim 1, and one or more pharmaceutically acceptable excipients.

8. A method of treating breast cancer or ovarian cancer, the method comprising administering to a subject in need thereof the solid form of RAD1901-2HCl according to claim 1, or a pharmaceutical composition according to claim 7.

9. The method according to claim 8, wherein said breast cancer or ovarian cancer is ER+.

10. The method according to claim 9, wherein the breast cancer or ovarian cancer is a resistant ER-driven cancer that progressed after endocrinological treatment, wherein the endocrinological treatment comprises administration of a drug selected from a Selective Estrogen Receptor Degrader (SERD), an aromatase inhibitor, a selective estrogen receptor modulator (SERM), a Human Epidermal Growth Factor Receptor 2 (Her2) inhibitor, a chemo therapeutic agent, a cdk4/6 inhibitor, an m-TOR inhibitor, an angiogenesis inhibitor, or rituximab.

11. The method according to claim 10, wherein
the SERD is selected from fulvestrant, 17β-[2-[4-[(diethylamino)methyl]-2-methoxyphenoxy]ethyl]-7α-methylestra-1,3,5 (10)-trien-3-ol (TAS-108 or (SR16234), 11β-Fluoro-7α-(14,14,15,15-pentafluoro-6-methyl-10-thia-6-azapentadecyl) estra-1,3,5 (10)-triene-3,17β-diol (ZK191703), (11β,17β)-11-[4-[5-[(4,4,5,5,5-Pentafluoropentyl) sulfonyl]-pentyl]oxy]phenylestra-1,3,5, (10)-triene-3,17-diol (RU58668), Brilanestrant (GDC-0810 or (ARN-810), Etacstil (GW5638 or/DPC974), (S)-2-(4-(2-(3-(fluoromethyl)-azetidin-1-yl) ethoxy) phenyl)-3-(3-hydroxyphenyl)-4-methyl-2H-chromen-6-ol (SRN-927), and (E)-3-(3,5-difluoro-4-((1R,3R)-2-(2-fluoro-2-methylpropyl)-3-methyl-2,3,4,9-tetrahydro-1H-pyrido [3,4-b]indol-1-yl)phenyl) acrylic acid (AZD9496);
the aromatase inhibitor is selected from anastrozole, exemestane, and letrozole;
the selective estrogen receptor modulator is selected from tamoxifen, raloxifene, lasofoxifene, and toremifene;
the Her2 inhibitor is selected from trastuzumab, lapatinib, ado-trastuzumab emtansine, and pertuzumab;
the chemo therapeutic agent is selected from abraxane, adriamycin, carboplatin, cytoxan, daunorubicin, doxil, ellence, fluorouracil, gemzar, helaven, lxempra, methotrexate, mitomycin, micoxantrone, navelbine, taxol, taxotere, thiotepa, vincristine, and xeloda; and
the angiogenesis inhibitor is bevacizumab.

12. The method according to claim 8, wherein the subject is further administered a cdk4/6 inhibitor and/or an m-TOR inhibitor.

13. The method according to claim 12, wherein the cdk4/6 inhibitor and/or m-TOR inhibitor is selected from palbociclib, ribociclib, abemaciclib, or everolimus, or a combination thereof.

14. The method according to claim 8, wherein the breast cancer or ovarian cancer is a resistant ER-driven cancer that progress after endocrinological treatment, wherein the breast cancer has one or more mutant ER binding domains comprising one or more mutations selected from the group consisting of Y537X1 wherein X1 is S, N, or C, D538G, L536X2 wherein X2 is R or Q, P535H, V534E, S463P, V392I, and E380Q, or a combination thereof.

15. The method according to claim 8, wherein the method comprises treating breast cancer.

16. The method according to claim 8, wherein the method comprises treating ovarian cancer.

* * * * *